United States Patent
Lee et al.

(10) Patent No.: US 10,329,582 B2
(45) Date of Patent: *Jun. 25, 2019

(54) GENETIC MODIFICATION OF RATS

(71) Applicant: Regeneron Pharmaceuticals, Inc., Tarrytown, NY (US)

(72) Inventors: Jeffrey D. Lee, New York, NY (US); Wojtek Auerbach, Ridgewood, NJ (US); David Heslin, Closter, NJ (US); David Frendewey, New York, NY (US); Ka-Man Venus Lai, Tarrytown, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/242,025

(22) Filed: Aug. 19, 2016

(65) Prior Publication Data

US 2017/0037429 A1    Feb. 9, 2017

Related U.S. Application Data

(62) Division of application No. 14/185,703, filed on Feb. 20, 2014, now abandoned.

(60) Provisional application No. 61/767,093, filed on Feb. 20, 2013.

(51) Int. Cl.
| | |
|---|---|
| *A01K 67/02* | (2006.01) |
| *A61D 19/04* | (2006.01) |
| *C12N 15/85* | (2006.01) |
| *A01K 67/027* | (2006.01) |
| *C12N 15/877* | (2010.01) |
| *C12N 5/0735* | (2010.01) |

(52) U.S. Cl.
CPC .......... *C12N 15/8509* (2013.01); *A01K 67/02* (2013.01); *A01K 67/0271* (2013.01); *A01K 67/0275* (2013.01); *A61D 19/04* (2013.01); *C12N 5/0606* (2013.01); *C12N 15/8775* (2013.01); *A01K 2207/12* (2013.01); *A01K 2217/15* (2013.01); *A01K 2227/105* (2013.01); *C12N 2501/235* (2013.01); *C12N 2501/727* (2013.01); *C12N 2501/999* (2013.01); *C12N 2510/00* (2013.01)

(58) Field of Classification Search
CPC .......... C12N 15/8509; C12N 15/8775; C12N 2501/235; C12N 2501/727; C12N 2510/00; A01K 67/02; A01K 67/0271; A01K 67/0275; A01K 2207/12; A01K 222/105

See application file for complete search history.

(56) References Cited

U.S. PATENT DOCUMENTS

| | | |
|---|---|---|
| 6,136,566 A | 10/2000 | Sands et al. |
| 6,372,956 B1 | 4/2002 | Goldsmith et al. |
| 7,294,754 B2 | 11/2007 | Poueymirou et al. |
| 7,771,967 B2 | 8/2010 | Huang et al. |
| 8,338,179 B2 | 12/2012 | Enenkel et al. |
| 8,502,018 B2 | 8/2013 | Murphy et al. |
| 8,558,055 B2 | 10/2013 | Ostertag et al. |
| 8,628,957 B2 | 1/2014 | Teratani et al. |
| 8,697,359 B1 | 4/2014 | Zhang |
| 8,722,964 B2 | 5/2014 | Ostertag et al. |
| 9,228,208 B2 | 1/2016 | Frendewey et al. |
| 2004/0018626 A1 | 1/2004 | Murphy et al. |
| 2005/0144655 A1 | 6/2005 | Economides et al. |
| 2007/0186293 A1 | 8/2007 | Teratani et al. |
| 2008/0014638 A1 | 1/2008 | Smith et al. |
| 2008/0066197 A1 | 3/2008 | Ying et al. |
| 2009/0055943 A1 | 2/2009 | Economides et al. |
| 2010/0041137 A1 | 2/2010 | Smith et al. |
| 2010/0218264 A1 | 8/2010 | Cui et al. |
| 2011/0041197 A1 | 2/2011 | Frendewey et al. |

(Continued)

FOREIGN PATENT DOCUMENTS

| | | |
|---|---|---|
| EP | 1 726 640 A1 | 11/2005 |
| EP | 1360287 B1 | 9/2012 |

(Continued)

OTHER PUBLICATIONS

Valenzuela et al., Nature Biotehcnology 23(6): 652-659, 2003.*
Aitman et al., "Progress and prospects in rat genetics: a community view," Nature Genetics, vol. 40(5), pp. 516-522, May 2008.
Blair et al., "Culture parameters for stable expansion, genetic modification and germline transmission of rat pluripotent stem cells," Biol. Open, vol. 1(1): pp. 58-65, Nov. 1, 2011.
Buehr et al., "Capture of Authentic Embryonic Stem Cells from Rat Blastocysts," Cell, vol. 135, pp. 1287-1298, 2008.

(Continued)

*Primary Examiner* — Thaian N Ton
(74) *Attorney, Agent, or Firm* — Yongjin Choi; Alston & Bird, LLP

(57) ABSTRACT

Compositions and methods are provided for making rat pluripotent and totipotent cells, including rat embryonic stem (ES) cells. Compositions and methods for improving efficiency or frequency of germline transmission of genetic modifications in rats are provided. Such methods and compositions comprise an in vitro culture comprising a feeder cell layer and a population of rat ES cells or a rat ES cell line, wherein the in vitro culture conditions maintain pluripotency of the ES cell and comprises a media having mouse leukemia inhibitory factor (LIF) or an active variant or fragment thereof. Various methods of establishing such rat ES cell lines are further provided. Methods of selecting genetically modified rat ES cells are also provided, along with various methods to generate a transgenic rat from the genetically modified rat ES cells provided herein. Various kits and articles of manufacture are further provided.

37 Claims, 21 Drawing Sheets
(15 of 21 Drawing Sheet(s) Filed in Color)
Specification includes a Sequence Listing.

(56) References Cited

U.S. PATENT DOCUMENTS

| | | |
|---|---|---|
| 2012/0142092 A1 | 6/2012 | Teratani et al. |
| 2012/0272349 A1 | 10/2012 | Ochiya et al. |
| 2013/0309670 A1 | 11/2013 | Frendeway et al. |
| 2014/0068797 A1 | 3/2014 | Doudna et al. |
| 2014/0235933 A1 | 8/2014 | Lee et al. |
| 2014/0273234 A1 | 9/2014 | Zhang et al. |
| 2014/0309487 A1 | 10/2014 | Lee et al. |
| 2014/0310828 A1 | 10/2014 | Lee et al. |
| 2014/0342456 A1 | 11/2014 | Mali et al. |
| 2015/0079680 A1 | 3/2015 | Bradley et al. |
| 2015/0159174 A1 | 6/2015 | Frendewey et al. |
| 2015/0159175 A1 | 6/2015 | Frendewey et al. |
| 2015/0240263 A1 | 8/2015 | Holmes et al. |
| 2015/0376650 A1 | 12/2015 | Auerbach et al. |
| 2015/0376651 A1 | 12/2015 | Frendewey et al. |
| 2016/0046960 A1 | 2/2016 | Frendewey et al. |
| 2016/0060657 A1 | 3/2016 | Frendewey et al. |
| 2016/0108360 A1 | 4/2016 | Lee et al. |
| 2016/0145646 A1 | 5/2016 | Frendewey et al. |

FOREIGN PATENT DOCUMENTS

| | | | |
|---|---|---|---|
| EP | 2508595 | A1 | 10/2012 |
| GB | 2 436 737 | A | 10/2007 |
| WO | WO 97/30151 | A1 | 8/1997 |
| WO | WO 1997/030151 | A1 | 8/1997 |
| WO | WO 2002/036789 | A2 | 5/2002 |
| WO | WO 2002/066630 | A1 | 8/2002 |
| WO | WO 2006/028723 | A1 | 3/2006 |
| WO | WO 2006/044962 | A1 | 4/2006 |
| WO | WO 2007/113505 | A2 | 10/2007 |
| WO | WO 2007/117410 | A2 | 10/2007 |
| WO | WO 2008/015418 | A2 | 2/2008 |
| WO | WO 2010/077955 | A1 | 7/2010 |
| WO | WO 2011/020005 | A1 | 2/2011 |
| WO | WO 2011/146121 | A1 | 11/2011 |
| WO | WO 2012/129198 | A1 | 9/2012 |
| WO | WO 2013/163394 | A1 | 10/2013 |
| WO | WO 2014/130706 | A1 | 8/2014 |
| WO | WO 2014/172489 | A2 | 10/2014 |
| WO | WO 2015/040402 | A1 | 3/2015 |
| WO | WO 2015/088643 | A1 | 6/2015 |
| WO | WO 2015/089462 | A1 | 6/2015 |
| WO | WO 2015/127439 | A1 | 8/2015 |
| WO | WO 2015/188109 | A1 | 12/2015 |
| WO | WO 2015/200805 | A2 | 12/2015 |
| WO | WO 2016/081923 | A2 | 5/2016 |

OTHER PUBLICATIONS

Cartwright et al., "LIF/STAT3 controls ES cell self-renewal and pluripotency by a Myc-dependent mechanism," Development, vol. 132(5), pp. 885-896, 2005.
Casanova et al., "Cross-Species Genome Wide Expression Analysis during Pluripotent Cell Determination in Mouse and Rat Preimplantation Embryos," PLoS One, vol. 7(10), e47107, 2012.
Cong et al., "Multiplex Genome Engineering Using CRISPR/Cas Systems," Science, vol. 339(6121), pp. 819-823 plus Supplemental Materials, Jan. 3, 2013.
Doudna et al., "The new frontier of genome engineering with CRISPR-Cas9," Science, vol. 346(6213), pp. 1258096-1-1258096-9, Nov. 28, 2014.
EMD-Millipore, Certificate of Analysis for Recombinant Human Leukemia Inhibitory Factor, retrieved from internet on Apr. 25, 2015 at <http://www.emdmillipore.com/US/en/product/Leukemia-Inhibitory-Factor-Protein%2C-Recombinant-human,MM_NF-LIF1010#documen.
EMD-Millipore, "Product Information sheet for Rat ESGRO," retrieved from internet on Apr. 25, 2015 at < http://www.emdmillipore.com/US/en/product/Rat-ESGRO%C2%AE%2C-1-million-units1-mL,MM_NF-ESG2206#anchor_COA>.

EP Application No. 14754746.7, Extended European Search Report dated Jun. 13, 2016.
EP Application No. 14784879.0, Extended European Search Report dated Sep. 19, 2016.
Gibco Data Sheet for "Recombinant Mouse Leukemia Inhibitory Factor (LIF), PMC4054," pp. 1-2, 2011.
Graf et al., "The Role of the Leukemia Inhibitory Factor (LIF)—Pathway in Derivation and Maintenance of Murine Pluripotent Stem Cells," Genes, vol. 2, pp. 280-297, 2011.
Hirabayashi et al., "Establishment of Rat Embryonic Stem Cell Lines That Can Participate in Germline Chimerae at High Efficiency," Mol. Reprod. Dev., vol. 77, p. 94, 2010.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Iannaccone, P., et al., "Pluripotent Embryonic Stem Cells from the Rat Are Capable of Producing Chimeras," Developmental Biology, 1994, vol. 163, pp. 288-292.
Kawamata et al., "Two distinct knockout approaches highlight a critical role for p53 in rat development," Sci. Rep., vol. 2, p. 945, 2012.
Kawamata, et al., "Generation of genetically modified rats from embryonic stem cells," PNAS, vol. 107, No. 32, pp. 14223-14228 (Aug. 10, 2010).
Kawamata, M., et al., "Establishment of Embryonic Stem Cells from Rat Blastocysts," Methods Mol. Biol., 2010, vol. 597, pp. 169-177.
Kobayashi et al., "Identification of Rat Rosa26 Locus Enables Generation of Knock-In Rat Lines Ubiquitously Expressing tdTomato," Stem Cells and Development, vol. 21(16), pp. 2981-2986, May 7, 2012.
Krivokharchenko, A., et al., "In Vitro Formation of Tetraploid Rat Blastocysts After Fusion of Two-Cell Embryos," Molecular Reproduction and Development, 2002, vol. 61, pp. 460-465.
Li et al., "Derivation of Germline Competent Rat Embryonic Stem Cells from DA Rats," J. Genet. Genomics, vol. 39, pp. 603-606, 2012.
Li et al., "Germline Competent Embryonic Stem Cells Derived from Rat Blastocysts," Cell, vol. 135, pp. 1299-1310, 2008.
Li et al., "Genetic modification and screening in rat using haploid embryonic stem cells," Cell Stem Cell, vol. 14(3); pp. 404-414, 2013 (epub Dec. 19, 2013).
Li, D., et al., "Heritable gene targeting in the mouse and rat using a CRISPR-Cas system," Nature Biotechnology, 2013, vol. 31(8), pp. 681-683.
Mali et al., "RNA-Guided Human Genome Engineering via Cas9," Science, vol. 339(6121), pp. 823-826 plus Supplemental Materials, Jan. 3, 2013.
Mashimo et al., "Generation of knockout rats with X-linked severe combined immunodeficiency (X-SCID) using zinc finger nucleases," PLoS One, vol. 5(1), p. e8870, 2010.
Matsuda et al., "STAT3 activation is sufficient to maintain an undifferentiated state of mouse embryonic stem cells," The EMBO Journal, vol. 18(15), pp. 4261-4269, 1999.
Meek et al., "Efficient Gene Targeting by Homologous Recombination in Rat Embryonic Stem Cells," PLoS One, vol. 5(12), p. e14225, 2010.
Men et al., "Germline Transmission of a Novel Rat Embryonic Stem Cell Line Derived from Transgenic Rats," Stem Cells Dev., vol. 21(14), pp. 2606-2612, 2012.
Musser, "Rodent," Brittanica. Retrieved from the Internet May 31, 2016: http://www.brittanica.com/animal/rodent.
PCT International Preliminary Report on Patentability for application PCT/US2014/017452 dated Aug. 25, 2015.
PCT International Preliminary Report on Patentability for application PCT/US2014/034412 dated Oct. 30, 2015
PCT International Preliminary Report on Patentability for application PCT/US2014/060788 dated Jun. 23, 2016.
PCT/US2014/017452 International Search Report and Written Opinion of the Searching Authority dated May 14, 2014.
PCT/US2014/034412 International Search Report and Written Opinion of the Searching Authority dated Oct. 9, 2014.

(56) References Cited

OTHER PUBLICATIONS

Piatkevich et al., "Guide to Red Fluorescent Proteins and Biosensors for Flow Cytometry," Methods Cell Biol., vol. 102, pp. 431-461, 2011.
Rathjen et al., "Differentiation Inhibiting Activity Is Produced in Matrix-Associated and Diffusible Forms That Are Generated by Alternate Promoter Usage," Cell, vol. 62, pp. 1105-1114, 1990.
Ruhnke, M., et al., "Long-Term Culture and Differentiation of Rat Embryonic Stem Cell-Like Cells into Neuronal, Glial, Endothelial, and Hepatic Lineages," Stem Cells, 2003, vol. 21, pp. 428-436.
Shen, H, et al., "The heterogeneity and dynamic equilibrium of rat embryonic stem cells," Cell Research (2011), vol. 21, pp. 1143-1147.
Sigma-Aldrich, "Product Information sheet for Leukemia Inhibitory Factor human," retrieved from internet on Apr. 25, 2015 at <http://www.sigmaaldrich.com/content/dam/sigma-aldrich/docs/Sigma/Datasheet/4/l5283dat.pdf>.
Stemgent Product Specification Sheet, PD0325901, pp. 1-2 (2012).
Tong et al., "Production of p53 gene knockout rats by homologous recombination in embryonic stem cells," Nature, vol. 467(7312), pp. 211-213, 2010.
Tong et al., "Generating gene knockout rats by homologous recombination in embryonic stem cells," Nature Protocols, vol. 6(6), pp. 827-844, 2011 (epub May 26, 2011).
U.S. Appl. No. 14/185,703 Non-Final Office Action dated Dec. 3, 2015.
U.S. Appl. No. 14/185,703, Requirement for Restriction/Election dated Sep. 4, 2015.
U.S. Appl. No. 14/254,715 Final Office Action dated Nov. 30, 2015.
U.S. Appl. No. 14/254,715, Final Office Action dated Sep. 19, 2016.
U.S. Appl. No. 14/254,715, Non-Final Office Action dated Apr. 21, 2016.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Advisory Action dated Aug. 15, 2016.
U.S. Appl. No. 14/314,866, Final Office Action dated Apr. 26, 2016.
U.S. Appl. No. 14/314,866, Non-Final Office Action dated Sep. 19, 2016.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314,866, Final Office Action dated Jun. 4, 2015.
U.S. Appl. No. 14/515,503, Non-Final Office Action dated May 20, 2016.
U.S. Appl. No. 14/515,503, Notice of Allowance dated Sep. 23, 2016.
U.S. Appl. No. 14/515,503, Requirement for Restriction/Election dated Mar. 4, 2016.
U.S. Appl. No. 14/928,134, Advisory Action dated Jul. 15, 2016.
U.S. Appl. No. 14/928,134, Final Office Action dated Apr. 14, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 14/185,703, Final Office Action dated Apr. 20, 2016.
U.S. Appl. No. 14/254,715, Requirement for Restriction/Election dated Jun. 4, 2015.
U.S. Appl. No. 14/928,180, Non-Final Office Action dated Jan. 5, 2016.
Ueda et al., "Establishment of Rat Embryonic Stem Cells and Making of Chimera Rats," PLoS One, vol. 3(7), p. e2800, 2008.
U.S. Appl. No. 14/928,134 Non-Final Office Action dated Feb. 1, 2016.
Varlakhanova et al., "Myc Maintains Embryonic Stem Cell Pluripotency and Self-Renewal," Differentiation, vol. 80(1), pp. 9-19, 2010.
Yamamoto et al., "Derivation of rat embryonic stem cells and generation of protease-activated receptor-2 knockout rats," Transgenic Res., vol. 21, pp. 743-755, 2012.
Yang, S., et al., "Derivation and Genetic Modification of Embryonic Stem Cells from Disease-Model Inbred Rat Strains," Stem Cells and Development., 2013, vol. 22(20), Abstract only.
Yang, S., et al., Retraction of "Derivation and Genetic Modification of Embryonic Stem Cells from Disease-Model Inbred Rat Strains," Stem Cells and Development, 2013, vol. 22(20), 2813.
Zhao et al., "Derivation of embryonic stem cells from Brown Norway rats blastocysts," J. Genet. Genomics, vol. 37, pp. 467-473, 2010.
Frendewey, "VelociGene: Large-scale Modification of Rodent Genomes," Wellcome Trust Advanced Course: Genetic Engineering of Mammalian Stem Cells, Mar. 13, 2014.
Frendeway, "VelociGene: Large-scale Modification of Rodent Genomes," Wellcome Trust Advanced Course: Genetic Engineering of Mammalian Stem Cells, Feb. 20, 2015.
U.S. Appl. No. 15/410,252 Non-Final Office Action dated May 18, 2018.
Vechkanov et al., "Fundamentals of Cell Engineering: A Study Guide", Rostov-on-Don, pp. 15 and 46-47, (2012).
Verkhovskaya et al, "The action of alkoxy-substituted glycerin on the morphofunctional properties of a passaged cell culture," Cryobiology 1:30-33; (1990).
Cohen, et al., "A transgenic Alzheimer Rat with Plaques, Tau Pathology, Behavioral Impairment, Oligomeric Aβ, and Fank Neuronal Loss," The Journal of Neuroscience, 33(15), 6256-6245, (Apr. 10, 2013).

* cited by examiner

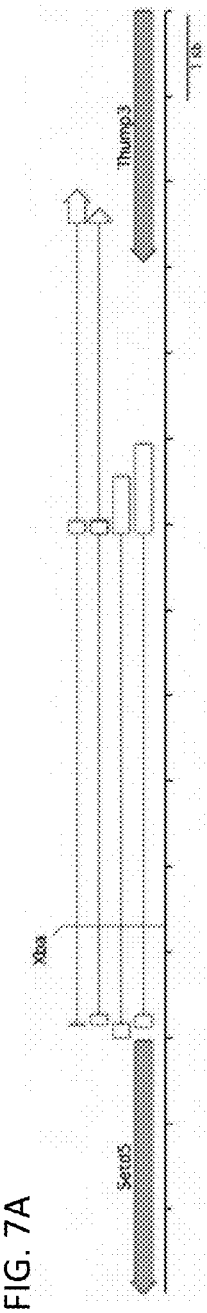
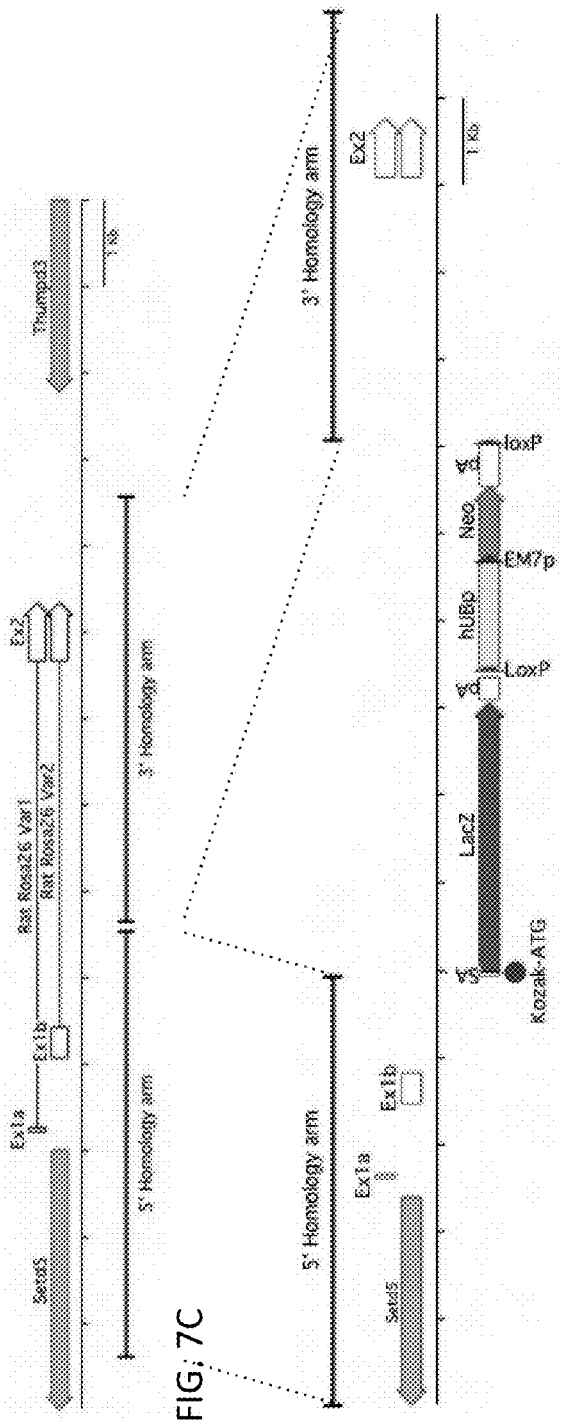
FIG. 7A
FIG. 7B
FIG. 7C

Cell Results: 42,XY

Label - Slide/Cell met-1 - S01-01

X, Y:

GENETIC MODIFICATION OF RATS

CROSS-REFERENCE TO RELATED APPLICATIONS

This application is a divisional application of U.S. patent application Ser. No. 14/185,703, filed Feb. 20, 2014, which claims priority to U.S. Provisional Application No. 61/767,093, filed Feb. 20, 2013, each of which is herein incorporated by reference in its entirety for all purposes.

FIELD

Non-human pluripotent, totipotent, and embryonic stem (ES) cells, in particular rat pluripotent, totipotent, and/or rat ES cells, and methods of making them. Methods for making rat pluripotent, totipotent, and ES cells are provided. Methods for targeting rat pluripotent, totipotent, and/or ES cells are provided. Methods for achieving germline transmission of a genetic modification in a rat cell are provided. Media for deriving, growing, and maintaining rat pluripotent, totipotent, and ES cells are provided.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 483214SEQLIST.txt, a creation date of Aug. 19, 2016, and a size of 2.09 kb. The sequence listing filed via EFS-Web is part of the specification and is hereby incorporated in its entirety by reference herein.

BACKGROUND

The rat has been a valuable model for many applications, including, but not limited to, applications in drug discovery. The usefulness of the rat has been mitigated somewhat by difficulty in obtaining genetically modified rats, in particular, in developing methods for genetically modifying rats, and generating useful rat cells that can be used in genetic modification protocols, including but not limited to protocols that result in germline transmission of a genetic modification in a rat genome.

There is a need in the art for rat cells (e.g., embryonic stem cells) that can be genetically modified such that the genetic modification can be transmitted through the germline. There is a need in the art for improved frequency of germline transmission of genetic modifications in rats.

There is a need in the art for donor rat pluripotent, totipotent, and/or ES cells from various strains of rat that are capable of generating F0, or wholly donor cell-derived, F0 rats. There is a need in the art for donor rat pluripotent, totipotent, and/or ES cells that are capable of generating rats that comprise a germline genetic modification.

SUMMARY

Compositions and methods are provided for making rat pluripotent and/or totipotent cells, including rat embryonic stem (ES) cells. Compositions and methods for improving efficiency or frequency of germline transmission of genetic modifications in rats are provided. In various aspects, the methods and compositions comprise an in vitro culture comprising a feeder cell layer and a population of rat ES cells or a rat ES cell line, wherein the in vitro culture conditions allow maintenance of pluripotency of the rat ES cell. Various methods of establishing rat ES cell lines are further provided. Method of selecting genetically modified rat ES cells are also provided, along with various methods to generate a transgenic rat from the genetically modified rat ES cells are provided herein. Various kits and articles of manufacture are further provided.

Non-limiting embodiments are as follows:

1. An isolated rat ES cell of a strain selected from ACI or DA, wherein the isolated rat ES cell is and capable of transmitting its genome through the germline.

2. The isolated rat ES cell of embodiment 1, wherein the cell is derived from an ACI rat.

3. The isolated rat ES cell of embodiment 1 or 2, wherein the cell is derived from a Dark Agouti (DA) rat.2.

4. The isolated rat ES cell of embodiment 1, 2, or 3, wherein the cell is euploid and capable of transmitting a targeted genetic modification through the germline.

5. The isolated rat ES cell of embodiment 4, wherein the rat ES cell comprises a germline transmission efficiency of the targeted genetic modification of at least 3%.

6. The isolated rat ES cell of embodiment 4, wherein the rat ES cell has a germline transmission efficiency of the targeted genetic modification of at least 60%.

7. The isolated rat ES cell of any one of embodiments 1-6, wherein the rat ES cell exhibits a targeting efficiency of homologous recombination of at least 2%.

8. The isolated rat ES cell of any one of embodiments 1-8, wherein the rat ES cell is capable of transmitting a targeted genetic modification into progeny following a successive round of electroporation.

9. The isolated rat ES cells of any one of embodiments 1-8, wherein the rat ES cell comprises one or more, two or more, or three or more targeted genetic modification.

10. The isolated rat ES cell of any one of embodiments 4-9, wherein the targeted genetic modification comprises an insertion, a deletion, a knockout, a knockin, a point mutation, or a combination thereof.

11. The isolated rat ES cell of embodiment 9, wherein the targeted genetic modification comprises at least one insertion of a heterologous polynucleotide into a genome of the cell.

12. The isolated rat ES cell of embodiment 11, wherein the heterologous polynucleotide comprises a selection marker.

13. The isolated rat ES cell of embodiment 12, wherein (a) the selection marker comprises a non-attenuated selection marker gene operably linked to a promoter; or (b) the rat ES cell comprises at least 2 copies of the polynucleotide encoding the selection marker.

14. The isolated rat ES cell of embodiment 12, wherein the selection marker has an increased activity compared to a wild type selection marker.

15. The isolated rat ES cell of any one of embodiments 1-14, wherein the rat ES cell forms a sphere-like colony when plated on a feeder cell layer in culture comprising a LIF polypeptide, a GSK3 inhibitor, and a MEK inhibitor.

16. The isolated rat ES cell of any one of embodiments 1-15, wherein the rat ES cell, when cultured in vitro, loosely adhere to the feeder cell layer.

17. The isolated rat ES cell of any one of embodiments 1-16, wherein the cell does not require paracrine LIF signaling for maintenance of pluripotency.

18. The isolated rat ES cell of any one of embodiments 1-17, wherein the cell is a male (XY) rat ES cell.

19. The isolated rat ES cell of any one of embodiments 1-19, wherein the cell is a female (XX) rat ES cell.

20. The isolated rat ES cell of any one of embodiments 1-19, wherein the rat ES cell can be passaged up to at least 11 times in a medium comprising a GSK3 inhibitor and a MEK inhibitor without decreasing its targeting efficiency or germline transmission efficiency of a targeted genetic modification.

21. The isolated rat ES cell of any one of embodiments 1-20, wherein the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

22. The isolated rat ES cell of any one of embodiments 1-21, wherein the rat ES cells do not express one or more pluripotency markers selected from c-Myc, Ecat1, Rexo1, or a combination thereof.

23. The isolated rat ES cell of any one of embodiments 1-22, wherein the rat ES cells do not express one or more mesodermal markers selected from Brachyury, Bmpr2, or a combination thereof.

24. The isolated rat ES cell of any one of embodiments 1-23, wherein the rat ES cells do not express one or more endodermal markers selected from Gata6, Sox17, Sox7, or combination thereof;

25. The isolated rat ES cell of any one of embodiments 1-24, wherein the rat ES cells do not express one or more neural markers selected from Nestin, Pax6, or combination thereof.

26. The isolated rat ES cell of any one of embodiments 1-25, wherein the cell expresses a pluripotency marker comprising Oct-4, Sox2, alkaline phosphatase, or a combination thereof.

27. The isolated rat ES cell of any one of embodiments 1-26, wherein the rat ES cell is characterized by the expression of one or more of a rat ESC-specific gene selected from one or more of Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), Left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof.

28. An isolated population of rat ES cells, wherein at least 70% of the rat ES cells are euploid and form sphere-like colonies when plated on a feeder cell layer in vitro.

29. The isolated population of rat ES cells of embodiment 28, wherein the rat ES cells are derived from an ACI rat.

30. The isolated population of rat ES cells of embodiment 28, wherein the rat ES cells are derived from a Dark Agouti (DA) rat.

31. The isolated population of rat ES cells of any one of embodiments 28-30, wherein the rat ES cells are capable of transmitting their genome through the germline.

32. The isolated population of rat ES cells of any one of embodiments 28-31, wherein the rat ES cells have a germline transmission efficiency of the targeted genetic modification of at least 3%.

33. The isolated population of rat ES cells of any one of embodiments 28-31, wherein the rat ES cells have a germline transmission efficiency of the targeted genetic modification of at least 60%.

34. The isolated population of rat ES cells of any one of embodiments 28-31, wherein the rat ES cells exhibit a targeting efficiency of homologous recombination of at least 2%.

35. The isolated population of rat ES cells of any one of embodiments 28-34, wherein the rat ES cells are capable of transmitting a targeted genetic modification into progeny following a successive round of electroporation.

36. The isolated population of any one embodiments 28-35, wherein the rat ES cells comprise one or more, two or more, or three or more targeted genetic modification and can transmit the targeted genetic modification through the germline.

37. The isolated population of rat ES cells of embodiment 36, wherein the targeted genetic modification is at the rat Rosa26 locus.

38. The isolated population of rat ES cells of embodiment 36, wherein the targeted genetic modification comprises an insertion, a deletion, a knockout, a knockin, a point mutation, or a combination thereof.

39. The isolated population of rat ES cells of embodiment 36, wherein the targeted genetic modification comprises at least one insertion of a heterologous polynucleotide into a genome of the cell.

40. The isolated population of rat ES cells of embodiment 39, wherein the heterologous polynucleotide comprises a selection marker.

41. The isolated population of rat ES cells of embodiment 40, wherein
(a) the selection marker comprises a non-attenuated selection marker gene operably linked to a promoter; or
(b) the rat ES cell comprises at least 2 copies of the polynucleotide encoding the selection marker.

42. The isolated population of rat ES cells of embodiment 40, wherein the selection marker has an increased activity compared to a wild type selection marker 43. The isolated population of rat ES cells of any one of embodiments 28-42, wherein the cells form a sphere-like colony when plated on a feeder cell layer in culture comprising a LIF polypeptide, a GSK3 inhibitor, and a MEK inhibitor.

44. The isolated population rat ES cells of any one of embodiments 28-43, wherein the cells, when cultured in vitro, loosely adhere to the feeder cell layer.

45. The isolated population of rat ES cells of any one of embodiments 28-44, wherein the cells do not require paracrine LIF signaling for maintenance of pluripotency.

46. The isolated population of rat ES cells of any one of embodiments 28-44, wherein the rat ES cells are a male (XY) rat ES cells.

47. The isolated population of rat ES cells of any one of embodiments 28-44, wherein the rat ES cells are female (XX) rat ES cells.

48. The isolated population of rat ES cells of any one of embodiments 28-47, wherein the rat ES cells can be passaged up to at least 11 times in a medium comprising a GSK3 inhibitor and a MEK inhibitor without decreasing its targeting efficiency or germline transmission efficiency of a targeted genetic modification.

49. The isolated population of rat ES cells of any one of embodiments 28-48, wherein the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

50. The isolated population of rat ES cells of any one of embodiments 28-49, wherein the rat ES cells do not express one or more pluripotency markers selected from c-Myc, Ecat1, Rexo1, or a combination thereof.

51. The isolated population of rat ES cells of any one of embodiments 28-50, wherein the rat ES cells do not express one or more mesodermal markers selected from Brachyury, Bmpr2, or a combination thereof.

52. The isolated population of rat ES cells of any one of embodiments 28-51, wherein the rat ES cells do not express one or more endodermal markers selected from Gata6, Sox17, Sox7, or combination thereof;

53. The isolated population of rat ES cells of any one of embodiments 28-52, wherein the rat ES cells do not express one or more neural markers selected from Nestin, Pax6, or combination thereof.

54. The isolated population of rat ES cells of any one of embodiment 28-53, wherein the rat ES cells expresses a pluripotency marker comprising Oct-4, Sox2, alkaline phosphatase, or a combination thereof.

55. The isolated population of rat ES cells of any one of embodiments 28-54, wherein the rat ES cells are characterized by the expression of one or more of a rat ESC-specific gene selected from one or more of Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof.

56. The isolated population of rat ES cells of any one of embodiments 28-55, wherein the population comprises at least $10^4$ cells.

57. The isolated population of rat ES cells of any one of embodiments 28-56, wherein the rat ES cells have one or more characteristic comprising:
a. at least 90% of the rat ES cells are euploid;
b. at least 70% of the rat ES cells express at least one pluripotency marker; wherein the at least one pluripotency marker comprises Oct-4, Sox2, alkaline phosphatase, or a combination thereof;
c. a cell from the rat ES cell population, when combined with a rat host embryo transmits the genome of the rat ES cell line into an offspring;
d. the rat ES cells when cultured in vitro loosely adhere to a feeder cell layer;
e. the rat ES cells form sphere-like colonies when plated on a feeder cell layer in vitro; (f) the rat ES cells maintain pluripotency when cultured in vitro in a media comprising an GSK3 inhibitor, a MEK inhibitor, LIF and a feeder cell layer that is not genetically modified to express LIF;
f. the rat ES cell exhibits a targeting efficiency of homologous recombination of at least 2%;
g. the rat ES cells maintain pluripotency in vitro without requiring paracrine LIF signaling;
h. at least 70% of the rat ES cells are euploid and form sphere-like colonies when plated on a feeder cell layer in vitro;
i. the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof;
j. the rat ES cells do not express one or more differentiation markers selected from c-Myc, Ecat1, Rexo1;
k. the rat ES cells do not express one or more mesodermal markers selected from Brachyury, Bmpr2, or a combination thereof;
l. the rat ES cells do not express one or more endodermal markers selected from Gata6, Sox17, Sox7, or combination thereof; and/or
m. the rat ES cells do not express one or more neural markers selected from Nestin, Pax6, or combination thereof.

58. The isolated population of rat ES cells of any one of embodiments 28-57, wherein (a) the rat ES cells is derived from a rat blastocyst; (b) the rat ES cell is derived from a rat morula stage embryo; and/or, (c) the rat ES cell line is derived from a superovulated rat.

59. An in vitro culture comprising a feeder cell layer, the population of rat embryonic stem (ES) cells, and a medium comprising a Leukemia Inhibitory Factor (LIF), GSK3 inhibitor, and a MEK inhibitor, wherein at least 70% of the rat ES cells are euploid and the rat ES cell forms a sphere-like colony.

60. The in vitro culture of embodiment 59 or 60, wherein the rat ES cell, loosely adhere to the feeder cell layer.

61. The in vitro culture of embodiment 59, 60, or 61, wherein the rat ES cells are capable of transmitting their genome through the germline.

62. The in vitro culture of embodiment 59, 60 or 61, wherein the rat ES cells are derived from an ACI rat.

63. The in vitro culture of embodiment 59, 60 or 61, wherein the rat ES cells are derived from a Dark Agouti (DA) rat.2.

64. The in vitro culture of any one of embodiments 59-63, wherein the rat ES cells are capable of transmitting a targeted genetic modification through the germline.

65. The in vitro culture of embodiment 64, wherein the rat ES cells comprise a germline transmission efficiency of the targeted genetic modification of at least 3%.

66. The in vitro culture of embodiment 64, wherein the rat ES cells have a germline transmission efficiency of the targeted genetic modification of at least 60%.

67. The in vitro culture of any one of embodiments 59-66, wherein the rat ES cells exhibit a targeting efficiency of homologous recombination of at least 2%.

68. The in vitro culture of any one of embodiments 59-67, wherein the rat ES cell is capable of transmitting a targeted genetic modification into progeny following a successive round of electroporation.

69. The in vitro culture of any one of embodiments 59-68, wherein the rat ES cell comprises one or more, two or more, or three or more targeted genetic modification.

70. The in vitro culture of embodiment 69, wherein the targeted genetic modification comprises an insertion, a deletion, a knockout, a knockin, a point mutation, or a combination thereof.

71. The in vitro culture of embodiment 69, wherein the targeted genetic modification comprises at least one insertion of a heterologous polynucleotide into a genome of the cell.

72. The in vitro culture of embodiment 71, wherein the heterologous polynucleotide comprises a selection marker.

73. The in vitro culture of embodiment 72, wherein (a) the selection marker comprises a non-attenuated selection marker gene operably linked to a promoter; or (b) the rat ES cell comprises at least 2 copies of the polynucleotide encoding the selection marker.

74. The in vitro culture of embodiment 72, wherein the selection marker has an increased activity compared to a wild type selection marker.

75. The in vitro culture of any one of embodiments 59-74, wherein the cell does not require paracrine LIF signaling for maintenance of pluripotency.

76. The in vitro culture of embodiment of any one of embodiments 59-75, wherein the cell is a male (XY) rat ES cell.

77. The in vitro culture of embodiment of any one of embodiments 59-75, wherein the cell is a female (XX) rat ES cell.

78. The in vitro culture of embodiment of any one of embodiments 59-77, wherein the rat ES cell can be passaged up to at least 11 times in a medium comprising a GSK3 inhibitor and a MEK inhibitor without decreasing its targeting efficiency or germline transmission efficiency of a targeted genetic modification.

79. The in vitro culture of any one of embodiments 59-78, wherein the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

80. The in vitro culture of any one of embodiments 59-79, wherein the rat ES cells do not express one or more pluripotency markers selected from c-Myc, Ecat1, Rexo1, or a combination thereof.

81. The in vitro culture of any one of embodiments 59-80, wherein the rat ES cells do not express one or more mesodermal markers selected from Brachyury, Bmpr2, or a combination thereof.

82. The in vitro culture of any one of embodiments 59-81, wherein the rat ES cells do not express one or more endodermal markers selected from Gata6, Sox17, Sox7, or a combination thereof;

83. The in vitro culture of any one of embodiments 59-82, wherein the rat ES cells do not express one or more neural markers selected from Nestin, Pax6, or combination thereof.

84. The in vitro culture of any one of embodiments 59-83, wherein the cell expresses a pluripotency marker comprising Oct-4, Sox2, alkaline phosphatase, or a combination thereof.

85. The in vitro culture of any one of embodiments 59-84, wherein the rat ES cells are characterized by the expression of one or more of a rat ESC-specific gene selected from one or more of Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (Drosophila) (Sall3), SATB homeobox 1 (Satb1), miR-632, or a combination thereof.

86. The in vitro culture of any one of embodiments 59-84, wherein the concentration of LIF is 50 U/ml to 150 U/ml.

87. The in vitro culture of any one of embodiments 59-85, wherein the concentration of LIF is 100 U/ml.

88. The in vitro culture of any one of embodiments 59-87, wherein the LIF is from mouse or comprises at least 92% sequence identity to SEQ ID NO: 1.

89. The in vitro culture of any one of embodiments 59-88, wherein the rat ES cell is capable of maintaining a pluripotency without requiring a paracrine LIF signaling.

90. The in vitro culture of any one of embodiments 59-89, wherein the feeder cell layer is not genetically modified to express LIF.

91. The in vitro culture of any one of embodiments 59-90, wherein the feeder cell layer comprises a monolayer of mitotically inactivated mouse embryonic fibroblasts (MEFs)

92. The in vitro culture of any one of embodiments 59-91, wherein the MEK inhibitor comprises PD0325901.

93. The in vitro culture of any one of embodiment 59-92, wherein the GSK-3 inhibitor comprises CHIR99021.

94. The in vitro culture of any one of embodiments 59-93, wherein the population of rat ES cells is derived from a rat blastocyst-stage embryo or a rat morula-stage embryo.

95. The in vitro culture of embodiment 94, wherein the blastocyst-stage or the morula-stage rat embryo further comprises an outgrowth of an amorphous undifferentiated mass of rat ES cells.

96. The in vitro culture of embodiment 94, wherein the population of rat ES cells comprises an isolated outgrowth of an amorphous undifferentiated mass of rat ES cells.

97. A method for generating a rat embryonic stem (ES) cell line comprising: (a) culturing in vitro a first feeder cell layer and a morula or a blastocyst-stage rat embryo, wherein the zona pellucida of the morula or blastocyst-stage rat embryo has been removed, and wherein the culture conditions maintain pluripotency of a rat ES cell and comprise a medium having mouse leukemia inhibitory factor (LIF) or a sequence having at least 91% sequence identity to SEQ ID NO:1 and having LIF activity, and a GSK3 inhibitor, and a MEK inhibitor; and, (b) transferring an outgrowth of an amorphous undifferentiated mass of rat ES cells to an in vitro culture well comprising a second feeder cell layer and culturing the outgrowth under conditions comprising the medium having the mouse LIF or an active variant of the mouse LIF, and thereby maintaining pluripotency of the rat ES cells; and, establishing a rat ES cell line therefrom.

98. The method of embodiment 97, wherein the rat ES cell line is passaged at least 5 times.

99. The method of embodiment 97 or 98, wherein the rat ES cell line is passaged at least 10 times.

100. The method of embodiment 97, 98, or 99, wherein the medium comprises about 50 U/ml to about 150 U/ml of mouse LIF.

101. The method of any one of embodiments 97-100, wherein the medium comprises about 100 U/ml of mouse LIF.

102. The method of any one of embodiments 97-101, wherein the feeder cell layer is not genetically modified to express LIF.

103. The method of any one of embodiments 97-102, wherein the feeder cell layer comprises a monolayer of mitotically inactivated mouse embryonic fibroblasts (MEFs).

104. The method of any one of embodiments 97-103, wherein the MEK inhibitor comprises PD0325901.

105. The method of any one of embodiments 97-104, wherein the GSK-3 inhibitor comprises CHIR99021.

106. The method of any one of embodiment 97-105, wherein (a) the rat ES cell line is derived from an ACI rat or derived from a Dark Agouti (DA) rat; (b) the rat ES cell line is derived from a morula-stage or a blastocyst-stage rat embryo; and/or, (c) the rat ES cell line is derived from a morula-stage or a blastocyst-stage embryo from a superovulated rat.

107. The method of any one of embodiments 97-106, wherein the medium further comprises at least one of an FGF receptor inhibitor, a ROCK inhibitor, or an ALK inhibitor.

108. The method of embodiment 107, wherein the FGF receptor inhibitor comprises PD184352, the ROCK inhibitor comprises Y-27632, or the ALK inhibitor comprises A-83-01.

109. The method any one of embodiments 97-108, wherein at least one rat ES cell has a germline transmission efficiency of the targeted genetic modification is at least 3%.

110. The method of embodiment any one of embodiments 97-109, wherein the germline transmission efficiency of the targeted genetic modification is at least 60%.

111. A method of selecting a rat embryonic stem (ES) cells having stably incorporated into its genome a heterologous polynucleotide comprising: (a) providing an in vitro population of rat ES cells; (b) introducing into at least one rat ES cell a heterologous polynucleotide comprising a selection marker operably linked to a promoter active the rat ES cell; and, (c) culturing in vitro the rat ES cell population in an alternating first and second culture media, wherein the first culture medium comprises an effective amount of a selection agent for a first time period and the second culture medium does not comprise the selection agent, wherein the in vitro culture conditions are sufficient to maintain pluripotency; thereby selecting the rat ES cell having stably integrated into its genome the heterologous polynucleotide.

112. The method of embodiment 111, wherein the first and second culture media are alternated every 24 hours.

113. The method of embodiment 111 or 112, wherein the selection marker imparts resistance to an antibiotic.

114. The method of any one of embodiments 111-113, wherein the antibiotic comprises G418.

115. The method of any one of embodiment 111-114, wherein the selection marker comprises neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), or a combination thereof.

116. The method of any one of embodiments 111-115, wherein (a) the selection marker has an increased activity compared to the wild type selection marker; and/or (b) multiple copies of the selection marker are stably incorporated into the genome of the rat ES cell.

117. The method of embodiment 116, wherein the selection marker is a non-attenuated selection marker.

118. A method for genetically modifying an isolated rat embryonic stem (ES) cell comprising introducing into the genome of an isolated rat ES cell of any one of embodiment 1-58 a heterologous polynucleotide to form a genetically modified rat ES cell.

119. A method of making a genetically modified rat comprising:
(a) introducing into the genome of the isolated rat embryonic stem (ES) cell of any one of embodiments 1-58, a heterologous polynucleotide to form a rat ES cell having a genetic modification;
(b) introducing at least one of the rat ES cells comprising the targeted genetic modification into a rat host embryo to produce an F0 embryo;
(c) implanting the F0 embryo into a surrogate mother;
(d) gestating the F0 embryo in the surrogate mother to term; and, (e) identifying an F0 rat having the targeted genetic modification.

120. The method of embodiment 119, further comprising breeding a male F0 rat with a wild type female rat to produce an F1 progeny that is heterozygous for the targeted genetic modification.

121. The method of embodiment 120, further comprising breeding a male F0 rat with a wild type female rat to produce an F1 progeny that is heterozygous for the targeted genetic modification.

122. The method of embodiment 119, further comprising breeding a male rat of the F1 progeny with a female rat of the F1 progeny to obtain an F2 progeny that is homozygous for the genetic modification.

123. The method of any one of embodiments 119-122, wherein at least 3% of the F0 rats having the genetic modification transmit the genetic modification to the F1 progeny.

124. The method of any one of embodiments 119-123, wherein at least 10% of the F0 rats having the genetic modification transmit the genetic modification to the F1 progeny.

125. The method of any one of embodiments 119-124, wherein at least 60% of the F0 rats having the genetic modification transmit the genetic modification to the F1 progeny.

126. The method of any one of embodiments 119-125, wherein the genetically modified rat ES cell is from the same rat strain as the rat host embryo.

127. The method of any one of embodiments 119-127, wherein the genetically modified rat ES cell is from a different rat strain as the rat host embryo.

128. The isolated population of rat ES cells of any of the preceding claims, the in vitro culture of any of the preceding claims, or the method of any of the preceding claims, wherein the rat ES cells in the population comprise:
  (a) at least 90% of the rat ES cells are euploid;
  (b) at least 70% of the rat ES cells express at least one pluripotency marker; wherein the at least one pluripotency marker comprises Oct-4, Sox2, alkaline phosphatase, or a combination thereof;
  (c) a cell from the rat ES cell population, when combined with a rat host embryo transmits the genome of the rat ES cell line into an offspring;
  (d) the rat ES cells when cultured in vitro loosely adhere to a feeder cell layer;
  (e) the rat ES cells form sphere-like colonies when plated on a feeder cell layer in vitro;
  (f) the rat ES cells maintain pluripotency when cultured in vitro in a media comprising an GSK3 inhibitor, a MEK inhibitor, LIF and a feeder cell layer that is not genetically modified to express LIF;

(g) the rat ES cell exhibits a targeting efficiency of homologous recombination of at least 2%;

(h) the rat ES cells maintain pluripotency in vitro without requiring paracrine LIF signaling;

(i) at least 70% of the rat ES cells are euploid and form sphere-like colonies when plated on a feeder cell layer in vitro;

(j) the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof;

(k) the rat ES cells do not express one or more differentiation markers selected from c-Myc, Ecat1, Rexo1.

(l) the rat ES cells do not express one or more mesodermal markers selected from Brachyury, Bmpr2, or a combination thereof;

(m) the rat ES cells do not express one or more endodermal markers selected from Gata6, Sox17, Sox7, or combination thereof; and/or (n) the rat ES cells do not express one or more neural markers selected from Nestin, Pax6, or combination thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A depicts Oct-4 (green); FIG. 2B depicts Sox-2 (red); FIG. 2C depicts DAPI (blue); FIG. 2D depicts an overlay of pluripotency markers expressed by rESCs.

FIG. 7A depicts targeting of the rat Rosa 26 locus, which lies between the Setd5 and Thumpd3 genes as in mouse, with the same spacing. FIG. 7A shows the structure of the mouse Rosa 26 locus. mRosa26 transcripts consist of 2 or 3 exons. FIG. 7B depicts the structure of the rRosa26 locus; the rat locus contains a second exon 1 (Ex1b) in addition to the homologous exon to mouse exon1 (Ex1a); no third exon has been identified in rat. FIG. 7C depicts a targeted rRosa26 allele; homology arms of 5 kb each were cloned by PCR using genomic DNA from DA rESC; the targeted allele contains a SA-lacZ-hUB-neo cassette replacing a 117 bp deletion in the rRosa26 intron.

DETAILED DESCRIPTION

Figure 1:
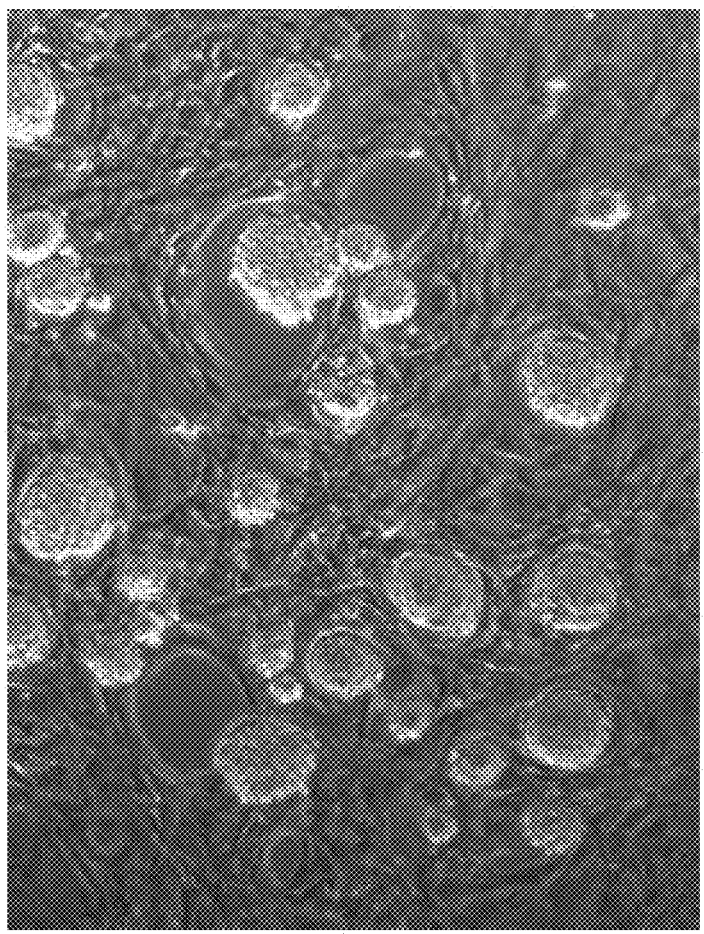
FIG. 1 depicts rESCs, which grow as compact spherical colonies that routinely detach and float in the dish.

The present methods and compositions now will be described more fully hereinafter with reference to the accompanying drawings, in which some, but not all embodiments of the methods and compositions are shown. Indeed, these methods and compositions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the methods and compositions set forth herein will come to mind to one skilled in the art to which this methods and compositions pertains having the benefit of the teachings presented in the foregoing descriptions and the associated drawings. Therefore, it is to be understood that the methods and compositions are not to be limited to the specific embodiments disclosed and that modifications and other embodiments are included within the scope of the appended claims. Although specific terms are employed herein, they are used in a generic and descriptive sense only and not for purposes of limitation.

I. Overview

The rat has long been the preferred rodent model organism for several fields of biomedical research such as cardiovascular disease, metabolism, toxicology, neurobiology and behavior. Hundreds of strains of rat have been developed; some are excellent models for complex human diseases such as hypertension, diabetes and cancer. However, progress in understanding the genetics of these models has been severely hampered by the difficulty of modifying the rat genome in a controlled manner. Through the use of site-specific endonucleases it is possible to produce mutations in a gene of interest, but this method remains imprecise and expensive. Targeting and germline transmission of rat ES cells remains a difficult task to achieve.

Isolation of rat ES cells (rESC) from two inbred strains of rat is described herein. rESC from the DA and ACI strains were derived. These cells express pluripotency markers and exhibit a normal 42X,Y karyotype. High percentage chimeras have been produced, by microinjection into SD host embryos at the blastocyst stage, and transmission of the rESC genome has been demonstrated through the germline for both strains. Using plasmid targeting vectors, we have produced targeted mutations in the rat equivalent of the ROSA26 locus, and we have achieved germline transmission of the targeted allele in both strains. These heterozygous animals express lacZ in all tissues at all stages examined.

In various aspects, ES cells were derived from the ACI strain in order to obtain a favorable number of male progeny from ACI donor ES cells. In one embodiment, the amount of male progeny is about 50%.

In various aspects, ES cells were derived from the DA strain in order to obtain primarily female progeny.

II. Rat Embryonic Stem (ES) Cells

Various compositions and methods are provided herein which comprise embryonic stem (ES) cells from rat. Stem cells are a cell population possessing the capability to self-renew indefinitely and are pluripotent. An "embryonic stem cell" or an "ES cell" comprises a stem cell obtained from an embryo or a fetus. The various rat ES cells provided herein can have one or more of any of the following properties:

(a) have germ-line competency, meaning when the rat ES cell is implanted into a rat host embryo, the genome of the rat ES cell line is transmitted into an offspring;

(b) have germ-line competency following at least one targeted genetic modification, meaning when the rat ES cell having the targeted genetic modification is implanted into a rat host embryo, the targeted genetic modification within the genome of the rat ES cell line is transmitted into an offspring;

(c) have pluripotency in vitro;

(d) have totipotency in vitro;

(e) when cultured in vitro loosely adhere to a feeder cell layer;

(f) when cultured in vitro form sphere-like colonies when plated on a feeder cell layer in vitro;

(g) maintain pluripotency when cultured in vitro under conditions comprising a feeder cell layer that is not genetically modified to express leukemia inhibitory factor (LIF), wherein the culture media comprises a sufficient concentration of LIF;

(h) maintain pluripotency when cultured in vitro under conditions comprising a feeder cell layer, wherein the culture media comprises mouse LIF or an active variant or fragment thereof;

(i) comprise a molecular signature that is characterized by
i) the expression of one or more of rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

ii) the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

iii) at least a 20-fold increase in the expression of one or more of the rat ES cell-specific genes as set forth in Table 14 when compared to a F1H4 mouse ES cell;

iv) at least a 20-fold increase in the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes as set forth in Table 14 when compared to a F1H4 mouse ES cell;

v) the expression of one or more of rat ES cell-specific genes as set forth in Table 13;

vi) the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13;

vii) at least a 20-fold increase in the expression of one or more of the rat ES cell-specific genes as set forth in Table 13 when compared to a F1H4 mouse ES cell;

viii) at least a 20-fold increase in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13 when compared to a F1H4 mouse ES cell;

ix) at least a 20-fold decrease in the expression of one or more of the rat ES cell-specific genes as set forth in Table 12 when compared to a F1H4 mouse ES cell; and/or x) at least a 20-fold decrease in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 12 when compared to a F1H4 mouse ES cell;

xi) any combination of expression of the rat ES cell-specific genes of parts (i)-(x);

xii) a relative expression level of pluripotency markers as shown in Table 15 for at least 2, 3, 4, 5, 6, 7, 8, 9, 10, 11, 12, 13, 14, 15, 16, 17 or 18 of the listed pluripotency markers. See, pluripotency ranking column of Table 15 for relative expression levels;

xiii) a relative expression level of the mesodermal markers as shown in Table 15 for at least 2, 3, or 4 of the listed mesodermal markers. See, mesodermal ranking column in Table 15 for relative expression levels;

xiv) a relative expression level of endodermal markers as shown in Table 15 for at least 2, 3, 4, 5, or 6 of the listed endodermal markers. See, endodermal ranking column in Table 15 for relative expression levels;

xv) a relative expression level of neural markers as shown in Table 15 for at least 2 and 3 of the listed neural markers. See, neural ranking column in table 15 for relative expression levels;

xvi) a relative expression level of trophectoderm markers as shown in Table 15 for the listed trophectoderm markers. See, trophectoderm ranking column in table 15 for relative expression levels;

xvii) any relative expression level of one or more (2, 3, 4, 5, 6, 7, 8, 9, 10, 11, 12, 13, 14, 15, 16, 17, 18, 19, 20, 21, 22, 23, 24, 25, 26, 27, 28, 29 or 30) of the pluripotency markers, mesodermal markers, endodermal markers, neural markers and/or trophectoderm markers set forth in Table 15;

xviii) the relative expression level of each of the markers set forth in table 15;

xix) any combination of the signatures set forth in xii-xiix; and/or xx) any combination of the signature set forth in i-xiix;

(j) have the ability to produce a F0 rat;

(k) are capable of being subcultured and maintaining the undifferentiated state;

(l) have the same number of chromosomes as a normal rat cell;

(m) maintain pluripotency in vitro without requiring paracrine LIF signaling; and/or (n) have self renewal, meaning they divide indefinitely while maintaining pluripotency.

One or more of the characteristics outlined in (a)-(n) can be present in an isolated rat ES cell, a rat ES cell population or a rat ES cell line provided herein, wherein the rat ES cells have not undergone a targeted genetic modification. In other embodiments, one or more of the characteristics outlined in (a)-(n) can be present in an isolated rat ES cell, a rat ES cell population or a rat ES cell line provided herein that has one or more targeted genetic modifications. A targeted genetic modification comprises an alteration in the genome of the rat ES cell and includes, for example, an insertion, a deletion, a knockout, a knockin, a mutation, or a combination thereof. In other instances, the targeted genetic modification comprises at least one insertion of a heterologous polynucleotide into the genome of the rat ES cell. A further description of such targeted genetic modifications are discussed elsewhere herein.

In specific embodiments, the various rat ES cells and cell lines provided herein are germ-line competent, meaning when the rat ES cell is implanted into a rat host embryo, the genome of the rat ES cell is transmitted into an offspring. Such transmission into the offspring (i.e., the F1 population) can occur when the rat ES cell has not undergone a targeted genetic modification. In addition, a rat ES cell having a targeted genetic modification are also germ-line competent, meaning when the rat ES cell having the targeted genetic modification is implanted into a rat host embryo, the targeted genetic modification of the rat ES cell is transmitted to the offspring (i.e., the F1 population.) Thus, in various aspects, the rat ES cells and methods described herein are employed to obtain a high frequency, or high efficiency, of germline transmission of a rat cell genome from both rat ES cells that have not undergone a targeted genetic modification and also from rat ES cells that have undergone a targeted genetic modification. In various embodiments, the frequency of germline transmission is greater than 1:600, greater than 1:500, greater than 1:400, greater than 1:300, greater than 1:200, and greater than 1:100. In various embodiments, the frequency of germline transmission is greater than 1%, greater than 2%, greater than 3%, greater than 4%, greater than 5%, greater than 6%, greater than 7%, greater than 8%, greater than 9%, greater than 10%, up to about 16%, greater than 25%, greater than 50%, greater than 60%, greater than 65%, greater than 70%, greater than 75% or greater. In various embodiments, the frequency of germline transmission ranges from 9% to 16%. In various aspects, percent of donor rESC-derived progeny in the F1 generation is 1% or more, 2% or more, 3% or more, 10% or more, 20% or more, 30% or more, 40% or more, 50% or more, 60% or more, from 3% to about 10% or more; from 3% or more to about 63%, from about 10% to about 30%, from about 10% to about 50%, from about 30% to about 70%, from about 30% to about 60%, from about 20% to about 40%, from about 20% to 65%, or from about 40% to 70%. Thus, a rat ES cell provided herein that has not undergone a targeted genetic modification or, alternatively, a rat ES cell that has a targeted genetic modification have the ability to transmit their genome into the F1 population.

A rat ES cell that has not undergone a targeted genetic modification or a rat ES cell that has a targeted genetic modification can be pluripotent and/or totipotent. "Pluripotent" or "pluripotency" refers to a stem cell that has the potential to differentiate into any of the three germ layers: endoderm, mesoderm, or ectoderm. Cell potency is a general term which describes a cell's ability to differentiate into other cell types. See, for example, Hans et al. (2007). "The Potential of Stem Cells: An Inventory". *Human biotechnology as Social Challenge*. Ashgate Publishing, Ltd. p. 28, herein incorporate by reference. The term "totipotency" or "totipotent" is the ability of a single cell to divide and produce all of the differentiated cells in an organism. See, for example, Western P (2009). *Int. J. Dev. Biol.* 53 (2-3): 393-409, herein incorporated by reference. In specific embodiments, the various ES cells disclosed herein can be either pluripotent and/or totipotent.

Figure 2:
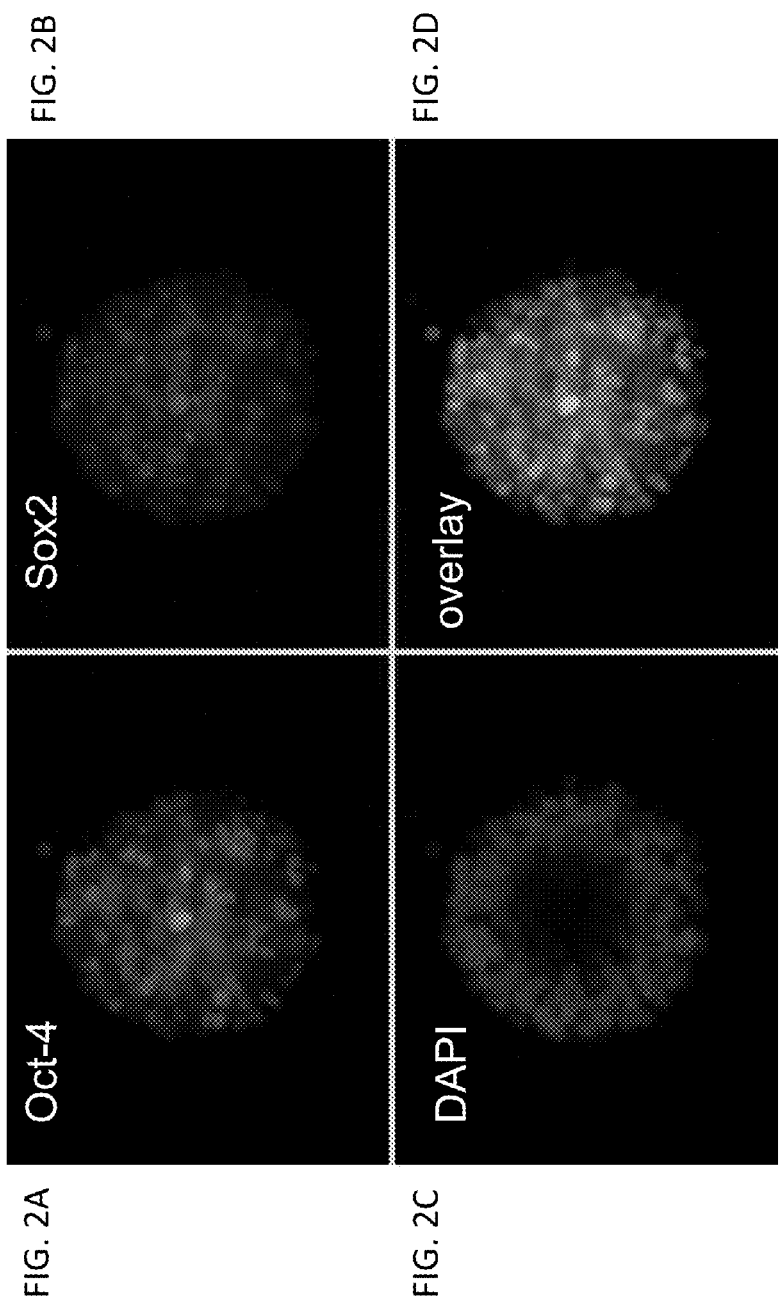
FIG. 2A through D depicts various pluripotency markers expressed by rESCs.
Figure 3:
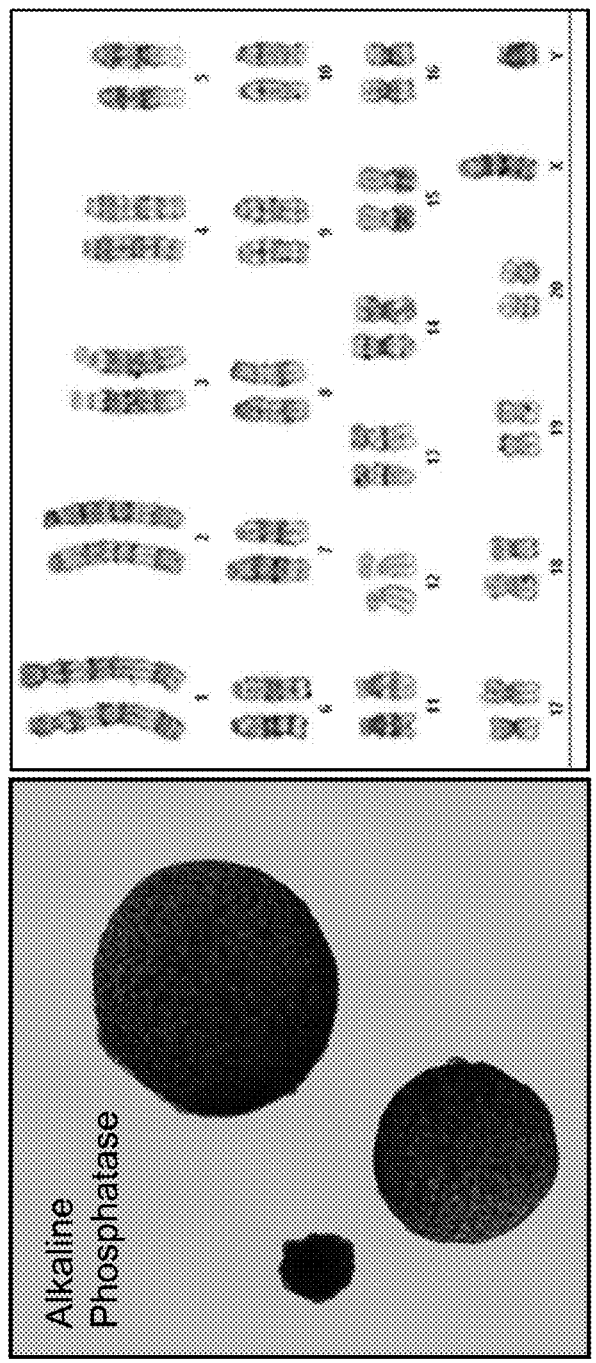
FIG. 3 depicts that the rESCs express light levels of alkaline phosphatase (a pluripotency marker) (left), and the karyotype for line DA.2B is 42X,Y (right). Karyotyping was done because rESCs often become tetraploid; lines were thus pre-screened by counting metaphase chromosome spreads, and lines with mostly normal counts were then formally karyotyped.

Various methods can be used to determine if a rat ES cell is pluripotent. For example, the ES cell can be assayed for the expression of various pluripotent markers including, but not limited to, Oct-4, Sox2, alkaline phosphatase, or a combination thereof. See, for example, Okamoto, K. et al., *Cell*, 60: 461-472 (1990), Scholer, H. R. et al., *EMBO J.* 9: 2185-2195 (1990)) and Nanog (Mitsui, K. et al., *Cell*, 113: 631-642 (2003), Chambers, I. et al., *Cell*, 113: 643-655 (2003) for various methods of assaying for the presence or the level of such markers. See, also FIGS. 2 and 3 provided herein. Other pluripotency markers include, for example, the presence of at least 1, 2, 3, 4, or 5 pluripotency marker comprising Nanog, Klf4, Dppa2, Fgf4, Rex1, Eras, Err-beta and/or Sall3. Other pluripotency markers include, for example, the absence of at least 1, 2, 3, 4, 5, 6, 7, 8, 9 or 10 pluripotency marker comprising T/Brachyury, Flk1, Nodal, Bmp4, Bmp2, Gata6, Sox17, Hhex1, Sox7, and/or Pax6.

In specific embodiments, the expression and/or the level of expression of these markers can be determined using RT-PCR. Various kits are available to determine the level and/or presence of alkaline phosphatase, including, for example, an ALP tissue staining kit (Sigma) and Vector Red Alkaline Phosphatase Substrate Kit I (Funakoshi) and the like. Additional assays include in situ hybridization, immunohistochemistry, immunofluorescence. In specific embodiments, the rat ES cell is characterized by expression of at least one pluripotency marker, including for example expression of Oct-4, Sox2, alkaline phosphatase, or a combination thereof, and preferably all three of these markers.

The various rat ES cell provided herein (i.e. rat ES cells that have not undergone a targeted genetic modification and/or rat ES cells that have a targeted genetic modification) are capable of maintaining pluripotency and/or totipotency while being maintained in in vitro culturing conditions. Thus, the various rat ES cells provide herein can, in some embodiments, be subcultured while still maintaining the undifferentiated state. Various methods of culturing the rat ES cells are discussed in further detail elsewhere herein.

The rat embryonic stem cells provided herein have been isolated from the rat embryo employing various isolation, purification, and culture expansion techniques which are discussed in detail elsewhere herein. The term "cell" as used herein refers to individual cells, cell lines, or cultures derived from such cells. An "isolated" rat ES cell or rat embryo has been removed from its natural environment. The term "isolated" can mean free from 70%, 80%, 90%, 95%, 96%, 97%, 98% or 99% of the constituents with which a component is found in its natural state. As used herein, a rat ES "cell line" comprises a population of isolated rat cells that were developed from a single rat ES cell and therefore the population of cells within a given cell line have a uniform genetic makeup other than for mutations or karyotypic changes occurring during propagation or during targeted genetic modifications. For example, as indicated elsewhere, the disclosed rat ES cells are characterized by a high level of euploidy. Nevertheless, in some cell lines the level of euploidy is less than 100% due to karyotypic changes in propagation of the line from a single cell. Moreover, a given population of rat ES cells can comprise at least 10 exp 3, 10 exp4, $10\times10^4$, $10\times10^5$, $10\times10^6$, $10\times10^7$, $10\times10^8$, $10\times10^9$, or $10\times10^{10}$ cells or greater. Some cell populations have sufficient cells to permit selection of a desired modified cell but not an excessively greater number so as to reduce the possibility of mutations or karyotypic changes developing in the cell line. For example, some cell populations have 10 exp3 to 10 exp6 cells.

As discussed elsewhere herein, various methods are provided for the targeted genetic modification of a rat ES cell line. When such methods are carried out, at least one cell within a rat ES cell line contains the targeted genetic modification. Through various culturing and/or selection techniques rat ES cell lines having one or more desired targeted genetic modifications are produced.

In specific embodiments, a rat ES cell, a population of rat ES cell or a rat ES cell line (that have not undergone a targeted genetic modification and/or have a targeted genetic modification) are euploid, and thus have a chromosome number that is an exact multiple of the haploid number. In further embodiment, a rat ES cell, a population of rat ES cells or a rat ES cell line (that have not undergone a targeted genetic modification and/or have a targeted genetic modification) are diploid, and thus have two haploid sets of homologous chromosomes. When referring to a rat ES cell population or a population of cells from a given population of rat ES cells or a rat ES cell line (that have not undergone a targeted genetic modification and/or have a targeted genetic modification), at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population or euploid and/or diploid. In other instances, when referring to a rat ES cell population or a population of cells from a given rat ES cell line (that have not undergone a targeted genetic modification and/or have a targeted genetic modification), at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population are euploid and/or diploid.

In still further embodiments, a rat ES cell, a population of rat ES cells or a rat ES cell line (that have not undergone a targeted genetic modification and/or have a targeted genetic modification) have 42 chromosomes. When referring to a rat ES cell population or a population of cells from a given rat ES cell line (that have not undergone a targeted genetic modification and/or have a targeted genetic modification) at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have 42 chromosomes. In other instances, when referring to a rat ES cell population or a population of cells from a given rat ES cell line (that have not undergone a targeted genetic modification and/or have a targeted genetic modification) at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have 42 chromosomes.

In further embodiments, a rat ES cell, a population of rat ES cells or a rat ES cell line (that have not undergone a targeted genetic modification and/or have a targeted genetic modification) provided herein form sphere-like colonies when plated on a feeder cell layer in vitro. The "sphere-like" morphology refers to the shape of rat ES cell colonies in culture, rather than the shape of individual ES cells. The rat ES cell colonies are spherical-like. Colonies which are loosely attached to the feeder cells appear circular (have a circular-like morphology). Free-floating colonies are spherical-like. The rat ES cell colonies are spherical-like and very compact, meaning: the boundaries between cells are very hard to see. The edge of the colony appears bright and sharp.

Individual nuclei are difficult to distinguish because the cells are very small (so that the nucleus takes up most of the volume of the cell). Mouse ES Cells form elongated colonies and attach strongly to feeder cells. mESC morphology can vary with strain; e.g. B6 colonies are rounder and more domed than F1H4 colonies but are still more elongated than rESC. Human ES cell colonies are flatter and more spread out than mESC colonies. The instant rat ES colonies are not flat and do not resemble human ES cell colonies.

In still further embodiments, a rat ES cell, a population of rat ES cells or a rat ES cell line (that have not undergone a targeted genetic modification and/or have a targeted genetic modification) have a circular morphology. A morphology scale for a circle is provided below, where a score of a 10 represents a perfect circle and a score of a 1 represents an ellipse.

Morphology Scale of a Circle:
- 10=A circle with a structure having a longitudinal axis and a vertical axis that run through the center of the structure and are of equal length.
- 9=A structure having a longitudinal axis and vertical axis that run through the center of the structure, wherein one of the axis is between 0.9999 to 0.9357 the length of the other axis.
- 8=A structure having a longitudinal axis and vertical axis that run through the center of the structure, wherein one of the axis is between 0.9357 to 0.875 the length of the other axis.
- 7=A structure having a longitudinal axis and vertical axis that run through the center of the structure, wherein one of the axis is between 0.875 to about 0.8125 the length of the other axis.
- 6=A structure having a longitudinal axis and vertical axis that run through the center of the structure, wherein one of the axis is between 0.8125 to 0.750 the length of the other axis.
- 5=A structure having a longitudinal axis and vertical axis that run through the center of the structure, wherein one of the axis is between 0.750 to 0.6875 the length of the other axis.
- 4=A structure having a longitudinal axis and vertical axis that run through the center of the structure, wherein one of the axis is between 0.6875 to 0.625 the length of the other axis.
- 3=A structure having a longitudinal axis and vertical axis that run through the center of the structure, wherein one of the axis is between 0.625 to 0.5625 the length of the other axis.
- 2=A structure having a longitudinal axis and vertical axis that run through the center of the circle, wherein one of the axis is between 0.5625 to 0.523 the length of the other axis.
- 1=An ellipse is defined as having a longitudinal axis and vertical axis that run through the center of the structure, wherein one of the axis is between 0.523 to 0.500 the length of the other axis.

In one non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have a circular morphology score of a 10, 9 or 8. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have a circular morphology score of a 10, 9, or 8.

In another non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have a circular morphology score of a 7, 6, 5, 4 or 3. In other non-limiting embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have a circular morphology score of a 7, 6, 5, 4, or 3.

In still further embodiments, sphere-like colonies form when the rat ES cells (that have not undergone a targeted genetic modification and/or have a targeted genetic modification) are plated on a feeder cell layer in vitro. A morphology scale for a sphere is provided below, where a score of a 10 represents a perfect sphere and a score of a 1 represents a three dimensional elliptical structure.

Morphology Scale of a Sphere-Like Structure:
- 10=A sphere is a structure having an X-axis and a Y-axis and a Z-axis each of which runs through the center of the structure and are of equal length.
- 9=A structure having an X axis and a Y-axis and a Z-axis that run through the center of the structure, wherein one of the axis is between 0.9999 to 0.9357 the length of at least one of the other axes.
- 8=A structure having an X axis and a Y-axis and a Z-axis that run through the center of the structure, wherein one of the axis is between 0.9357 to 0.875 the length of at least one or both of the other axes.
- 7=A structure having an X axis and a Y-axis and a Z-axis that run through the center of the structure, wherein one of the axis is between 0.875 to 0.8125 the length of at least one or both of the other axes.
- 6=A structure having an X axis and a Y-axis and a Z-axis that run through the center of the structure, wherein one of the axis is between 0.8125 to 0.750 the length of at least one or both of the other axes.
- 5=A structure having an X axis and a Y-axis and a Z-axis that run through the center of the structure, wherein one of the axis is 0.750 to 0.6875 the length of at least one or both of the other axes.
- 4=A structure having an X axis and a Y-axis and a Z-axis that run through the center of the structure, wherein one of the axis is 0.6875 to 0.625 the length of at least one or both of the other axes.

3=A structure having an X axis and a Y-axis and a Z-axis that run through the center of the structure, wherein one of the axis is between 0.625 to 0.5625 the length of at least one or both of the other axes.

2=A structure having an X axis and a Y-axis and a Z-axis that run through the center of the structure, wherein one of the axis is between 0.5625 to 0.523 the length of at least one or both of the other axes.

1=A structure having an X axis and a Y-axis and a Z-axis that run through the center of the structure, wherein one of the axis is between 0.523 to 0.500 the length of at least one or both of the other axes.

In one non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the colonies that form when the cells are plated on a feeder cell layer in vitro have a sphere-like morphology of a 10, 9 or 8. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the colonies that form when the cells are plated on a feeder cell layer in vitro have a sphere-like morphology of a 10, 9 or 8.

In another non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the colonies that form when the cells are plated on a feeder cell layer in vitro have a sphere-like morphology of a 7, 6, 5, 4, or 3. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the colonies that form when the cells are plated on a feeder cell layer in vitro have a sphere-like morphology of a 7, 6, 5, 4, or 3.

A given rat ES cell, a population of rat ES cells or a rat ES cell line provided herein can be a male (XY) rat ES cell, a male (XY) population of rat ES cells, or a male (XY) rat ES cell line. In other embodiments, a population of rat ES cells or a rat ES cell line provided herein can be a female (XX) rat ES cell, a female (XX) population of rat ES cells, or a female (XX) rat ES cell line. Any such rat ES cell, population of rat ES cells or rat ES cell line can comprise the euploidy and/or diploidy as described above.

The various rat ES cell provided herein can be from any rat strain, including but not limited to, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. The various rat ES cells can also be obtained from a strain derived from a mix of two or more strains recited above. In one embodiment, the rat ES cell is derived from a strain selected from a DA strain and an ACI strain. In a specific embodiment, the rat ES cell is derived from an ACI strain. The ACI rat strain is are characterized as having black agouti, with white belly and feet and an $RT1^{av1}$ haplotype. Such strains are available from a variety of sources including Harlan Laboratories. In other embodiments, the various rat ES cells are from a Dark Agouti (DA) rat strain which is characterized as having an agouti coat and an $RT1^{av1}$ haplotype. Such rats are available from a variety of source including Charles River and Harlan Laboratories. In a further embodiment, the various rat ES cells provided herein are from an inbred rat strain.

In specific embodiments the rat ES cell line is from an ACI rat and comprises the ACI.G1 rat ES cell as described herein. In another embodiment, the rat ES cell line is from a DA rat and comprises the DA.2B rat ES cell line or the DA.2C rat ES cell line as described herein. A given rat ES cell provided herein can be obtained from a rat embryo at any stage of rat embryo development. Representative stages of rat embryo development are outline below in Table 1. The rat embryos employed to derive the rat ES cells can be a morula-stage embryo, a blastocyst-stage embryo, or a rat embryo at a developmental stage between a morula-stage embryo and a blastocyst-stage embryo. Thus, in specific embodiments, the rat embryo employed is at or between the Witschi stages of 5 and 7. In other embodiments, the rat embryo employed is at the Witschi stage 5, 6, or 7.

In one embodiment, the rat ES cell is obtained from a rat blastocyst. In other embodiments, the rat ES cell is obtained from a blastocyst from a superovulated rat. In other embodiments, the rat ES cells are obtained from an 8-cell stage embryo which is then cultured in vitro until it develops into a morula-stage, blastocyst stage, an embryo between the Witschi stages 5 and 7, or into an embryo at the Witschi stage 5, 6, or 7. At which time the embryos are then plated. Morula-stage embryos comprise a compact ball of cells with no internal cavity. Blastocyst-stage embryos have a visible internal cavity (the blastocoel) and contain an inner cell mass (ICM). The ICM cells form ES cells.

TABLE 1

Stages of Rat Embryo Development

| Standard Stages (Witschi) | Age (days) | Identification of Stages |
|---|---|---|
| | | Cleavage and Blastula |
| 1 | 1 | 1 cell (in oviduct) |
| 2 | 2 | 2 cells (in oviduct) |
| 3 | 3 | 4 cells (in oviduct) |
| 4 | 3.25 | 8-12 cells (in oviduct) |
| 5 | 3.5 | Morula (in uterus) |
| 6 | 4 | Early blastocyst (in uterus) |
| 7 | 5 | Free blastocyst (in uterus) |
| | | Gastrula |
| 8 | 6 | Implanting blastocyst, with trophoblastic cone and inner cell mass; outgrowth of endoderm (hypoblast) |
| 9 | 6.75 | Diplotrophoblast; inner cell mass (pendant), covered with endoderm |
| 10 | 7.25 | Near complete implantation; pendant begins differentiation into embryonic and extra-embryonic parts |

TABLE 1-continued

Stages of Rat Embryo Development

| Standard Stages (Witschi) | Age (days) | Identification of Stages |
|---|---|---|
| 11 | 7.75 | Completion of implantation; primary amniotic cyst; ectoplacental cone |

Further provided are various rat ES cells (that have not undergone a targeted genetic modification and/or have a targeted genetic modification) which are characterized by The rat ES cell is characterized by:

i) the expression of one or more of rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (Drosophila) (Sall3), SATB homeobox 1 (Satb1), miR-632, or a combination thereof;

ii) the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (Drosophila) (Sall3), SATB homeobox 1 (Satb1), miR-632, or a combination thereof;

iii) at least a 20-fold increase in the expression of one or more of the rat ES cell-specific genes as set forth in Table 14 when compared to a F1H4 mouse ES cell;

iv) at least a 20-fold increase in the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes as set forth in Table 14 when compared to a F1H4 mouse ES cell;

v) the expression of one or more of rat ES cell-specific genes as set forth in Table 13;

vi) the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13;

vii) at least a 20-fold increase in the expression of one or more of the rat ES cell-specific genes as set forth in Table 13 when compared to a F1H4 mouse ES cell;

viii) at least a 20-fold increase in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13 when compared to a F1H4 mouse ES cell;

ix) at least a 20-fold decrease in the expression of one or more of the rat ES cell-specific genes as set forth in Table 12 when compared to a F1H4 mouse ES cell; and/or x) at least a 20-fold decrease in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 12 when compared to a F1H4 mouse ES cell;

xi) any combination of expression of the rat ES cell-specific genes of parts (i)-(x);

xii) a relative expression level of pluripotency markers as shown in Table 15 for at least 2, 3, 4, 5, 6, 7, 8, 9, 10, 11, 12, 13, 14, 15, 16, 17 or 18 of the listed pluripotency markers. See, pluripotency ranking column of Table 15 for relative expression levels;

xiii) a relative expression level of the mesodermal markers as shown in Table 15 for at least 2, 3, or 4 of the listed mesodermal markers. See, mesodermal ranking column in Table 15 for relative expression levels;

xiv) a relative expression level of endodermal markers as shown in Table 15 for at least 2, 3, 4, 5, or 6 of the listed endodermal markers. See, endodermal ranking column in Table 15 for relative expression levels;

xv) a relative expression level of neural markers as shown in Table 15 for at least 2 and 3 of the listed neural markers. See, neural ranking column in table 15 for relative expression levels;

xvi) a relative expression level of trophectoderm markers as shown in Table 15 for the listed trophectoderm markers. See, trophectoderm ranking column in table 15 for relative expression levels;

xvii) any relative expression level of one or more (2, 3, 4, 5, 6, 7, 8, 9, 10, 11, 12, 13, 14, 15, 16, 17, 18, 19, 20, 21, 22, 23, 24, 25, 26, 27, 28, 29 or 30) of the pluripotency markers, mesodermal markers, endodermal markers, neural markers and/or trophectoderm markers set forth in Table 15;

xviii) the relative expression level of each of the markers set forth in table 15;

xix) any combination of the signatures set forth in xii-xiix; and/or xx) any combination of the signature set forth in i-xiix.

In one embodiment, when transplanted into a pre-morula stage rat embryo, the rat ES cell (that have not undergone a targeted genetic modification and/or have a targeted genetic modification) can contribute to at least 90% of the cells in an F0 generation, contribute to at least 95% of the cells in an F0 generation, contribute to at least 96% of the cells in an F0 generation, contribute to at least 97% of the cells in an F0 generation, contribute to at least 98% of the cells in an F0 generation, or contribute to at least 99% of the cells in an F0 generation.

III. Derivation and Propagation of Rat Embryonic Stem (ES) Cells

Various methods are provided for obtaining the rat ES cells disclosed herein. In specific embodiments, such methods comprise (a) providing an in vitro culture comprising a feeder cell layer and a population of isolated rat embryonic stem (ES) cells; (b) culturing in vitro under conditions which are sufficient to maintain pluripotency and/or totipotency of the isolated rat ES cell. Such methods thereby allow for the propagation of a rat ES cell population and/or a rat ES cell line.

In one embodiment, a method for culturing a rat embryonic stem cell line is provided. Such methods comprises culturing in vitro a feeder cell layer and a rat ES cell line, wherein the culture conditions maintain pluripotency of the rat ES cells and comprise a media having mouse leukemia inhibitory factor (LIF) or an active variant or fragment thereof. The various methods further comprise passaging and culturing in vitro the cells of the rat ES cell line, wherein each subsequent in vitro culturing comprises culturing the rat ES cells on the feeder cell layer under conditions that maintain pluripotency of the rat ES cells and comprises a media having mouse LIF or an active variant or fragment thereof.

i. Culture Conditions

The culture media employed in the various methods and compositions will maintain the rat ES cells. The terms "maintaining" and "maintenance" refer to the stable preservation of at least one or more of the characteristics or phenotypes of the rat ES cells outline herein. Such phenotypes can include maintaining pluripotency and/or totipotency, cell morphology, gene expression profiles and the other functional characteristics of the rat stem cells described herein. The term "maintain" can also encompass the propagation of stem cells, or an increase in the number of stem cells being cultured. The term further contemplates culture conditions that permit the stem cells to remain pluripotent, while the stem cells may or may not continue to divide and increase in number.

The term "feeder cell" or "feeder cell layer" refers to a culture of cells that grow in vitro and secrete at least one factor into the culture medium that is used to support the growth of another cell of interest in the culture. The feeder cells employed herein aid in maintaining the pluripotency of the rat ES cells, and in specific embodiments, one or more of the other characteristics or phenotypes described herein. Various feeder cells can be used including, for example, mouse embryonic fibroblasts, including mouse embryonic fibroblasts obtained between the 12$^{th}$ and 16$^{th}$ day of pregnancy. In specific embodiments, feeder cell layer comprises a monolayer of mitotically inactivated mouse embryonic fibroblasts (MEFs).

The in vitro cultures of the rat ES cells further comprise an effective amount of Leukemia Inhibitory Factor (LIF) or an active variant or fragment thereof. Leukemia inhibitory factor (LIF) belongs to the IL-6 receptor family. LIF binds to a heterodimeric membrane receptor made up of a LIF-specific subunit, gp190 or LIFR, and the subunit gp130, which is shared with the other members of the IL-6 family. LIF inhibits the differentiation of embryonic stem cells in mice and contribute to stem cell self-renewal. Human and mouse LIF share 79% sequence homology and exhibit cross-species activity. Rat LIF (rtLIF) is a 22.1 kDa protein containing 202 amino acid residues that exhibits 91% amino acid sequence identity with murine LIF (Takahama et al. 1998). There are six possible asparagine-linked glycosylation (N-glycosylation) sites which are conserved among the LIF polypeptide from the various species and an additional site of Asn150 which is specific for rat LIF. The tertiary structure of the mouse LIF and its function is described in further detail in Aikawa et al. (1998) Biosci. Biotechnol. Biochem. 62 1318-1325 and Senturk et al. (2005) Immunology of Pregnancy, editor Gil Mor., U.S. Pat. No. 5,750,654 and D P Gearing (1987) EMBO Journal 1987 Dec. 20, each of which is herein incorporated by reference in their entirety. A partial mouse LIF sequence is reported on the SwissProt website under the accession number P09056.

Mouse LIF activity is assessed by its ability to induce differentiation of M1 myeloid leukemia cells. The specific activity is $1 \times 10^6$ units/ml (Cat. No. 03-0011 from Stemgent) and $1 \times 10^7$ units/ml (Cat. No. 03-0011-100 from Stemgent), where 50 units is defined as the amount of mouse LIF required to induce differentiation in 50% of the M1 colonies in 1 ml of medium. See, also, Williams, R. L. et al. (1988) Nature 336: 684-687; Metcalf, D. et al. (1988) Leukemia 2: 216-221; Niwa, H. et al. (2009) Nature 460: 118-122; Xu, J. et al. (2010) Cell Biol Int. 34: 791-797; Fukunaga, N. et al. (2010) Cell Reprogram. 12: 369-376; and, Metcalf D. (2003) Stem Cells 21: 5-14, each of which is herein incorporated by reference in their entirety. An "effective amount of LIF" comprises a concentration of LIF that allows the rat ES cells of an in vitro culture to remain in an undifferentiated pluripotent state. Various markers that can be used to assay for the cells remaining in a pluripotent state are discussed elsewhere herein.

The LIF polypeptide employed in the various methods and compositions provided herein can be from any organism, including from a mammal, a rodent, a human, a rat or a mouse. In one embodiment, the LIF polypeptide is from a mouse. In still further embodiments, the mouse LIF polypeptide comprises the amino acid sequence set forth in SwissProt Accession number: P09056, which is herein incorporated by reference in its entirety and is also set forth in SEQ ID NO: 1.

In other embodiments, an active variant or fragment of the mouse LIF polypeptide as set forth in SEQ ID NO: 1 or in SwissProt Accession number: P09056 can be used. Such active variants and fragments (including active variants having at least 75%, 80%, 85% 90%, 91%, 92%, 93%, 94%, 95%, 96%, 97%, 98%, or 99% sequence identity to SEQ ID NO: 1) are discussed in further detail elsewhere herein.

LIF polypeptide or the active variant or fragment thereof can be provided to the in vitro culture in a variety of ways. In one embodiment, the effective amount of the LIF polypeptide or the active variant or fragment thereof is added to the culture media. In other embodiments, the feeder cells have been genetically modified to overexpress the LIF polypeptide or the active variant or fragment thereof. Such feeder cells include feeder cells prepared from gamma-irradiated or mitomycin-C treated DIA-M mouse fibroblasts that express matrix-associated LIF. Method of generating and using such genetically modified feeder cells can be found, for example, in See, Buehr et al. (2003) Biol Reprod 68:222-229, Rathjen et al. (1990) Cell 62 1105-1115, and Buehr et al. (2008) Cell 135:1287-1298, each of which is herein incorporated by reference. The heterologous LIF expressed in the feeder cells can be from the same organism as the feeder cells or from an organism that is different from that of the feeder cell. In addition, the heterologous LIF expressed in the feeder cells can be from the same or from a different organism than the ES cells the feeder layer is supporting.

In still other embodiments, the feeder cells employed in the various methods disclosed herein are not genetically modified to express a heterologous LIF polypeptide or an active variant or fragment thereof. Thus, in particular embodiments, the monolayer of mitotically inactivated mouse embryonic fibroblast employed in the methods has not been genetically modified to express a heterologous LIF polypeptide.

In other embodiments, the LIF polypeptide or the active variant or fragment thereof is added to the culture media. When LIF is added to the culture media, the LIF can be from any organism, including from a mammal, a rodent, a human, a rat or a mouse. In one embodiment, the LIF present in the culture media is from a mouse. In still further embodiments, the mouse LIF polypeptide comprises the amino acid sequence set forth in SEQ ID NO: 1. In other embodiments, an active variant or fragment of the mouse LIF polypeptide as set forth in SEQ ID NO:1 can be used. Such active variants and fragments (including active variants having at least 75%, 80%, 85% 90%, 91%, 92%, 93%, 94%, 95%, 96%, 97%, 98%, or 99% sequence identity to SEQ ID NO: 1) are discussed in further detail elsewhere herein.

In specific embodiments, the rat ES cells and rat ES cell lines provided herein maintain pluripotency in vitro without requiring paracrine LIF signaling.

In specific embodiments, LIF or an active variant or fragment thereof is present in the culture media at any concentration that maintains the rat ES cells. LIF polypeptide or active variant or fragment thereof is present in the culture media at about 25 U/ml to about 50 U/ml, at about 50 U/ml to about 100 U/ml, at about 100 U/ml to about 125 U/ml, at about 125 U/ml to about 150 U/ml, at about 150 U/ml to about 175 U/ml, at about 175 U/ml to about 200 U/ml, at about 200 U/ml to about 225 U/ml, at about 225 U/ml to about 250 U/ml, at about 250 U/ml to about 300 U/ml, to about 300 U/ml to about 325 U/ml, at about 325 U/ml to about 350 U/ml, at about 350 U/ml to about 400 U/ml, at about 400 U/ml to about 425 U/ml, at about 425 U/ml to about 450 U/ml, at about 450 U/ml to about 475 U/ml, at about 475 U/ml to about 500 U/ml, at about 75 U/ml to about 500 U/ml or greater. In other embodiments, LIF polypeptide or active variant or fragment thereof is present in the culture media at about 25 U/ml to about 50 U/ml, at about 25 U/ml to about 100 U/ml, at about 75 U/ml to about 125 U/ml, at about 50 U/ml to about 150 U/ml, at about 90 U/ml to about 125 U/ml, at about 90 U/ml to about 110 U/ml, at about 80 U/ml to about 150 U/ml, at about 80 U/ml to about 125 U/ml. In a specific embodiment, LIF polypeptide or active variant or fragment thereof is present in the culture media at about 100 U/ml.

When mouse LIF is employed, the mouse LIF polypeptide or active variant or fragment thereof is present in the culture media at any concentration that maintains the rat ES cells. Mouse LIF polypeptide or active variant or fragment thereof is present at about 25 U/ml to about 50 U/ml, at about 50 U/ml to about 100 U/ml, at about 100 U/ml to about 125 U/ml, at about 125 U/ml to about 150 U/ml, at about 150 U/ml to about 175 U/ml, at about 175 U/ml to about 200 U/ml, at about 200 U/ml to about 225 U/ml, at about 225 U/ml to about 250 U/ml, at about 250 U/ml to about 300 U/ml, to about 300 U/ml to about 325 U/ml, at about 325 U/ml to about 350 U/ml, at about 350 U/ml to about 400 U/ml, at about 400 U/ml to about 425 U/ml, at about 425 U/ml to about 450 U/ml, at about 450 U/ml to about 475 U/ml, at about 475 U/ml to about 500 U/ml, at about 75 U/ml to about 500 U/ml or greater. In other embodiments, mouse LIF polypeptide or active variant or fragment thereof is present at about 25 U/ml to about 50 U/ml, at about 25 U/ml to about 100 U/ml, at about 75 U/ml to about 125 U/ml, at about 50 U/ml to about 150 U/ml, at about 90 U/ml to about 125 U/ml, at about 90 U/ml to about 110 U/ml, at about 80 U/ml to about 150 U/ml, at about 80 U/ml to about 125 U/ml. In a specific embodiment, mouse LIF polypeptide or active variant or fragment thereof is present in the culture media at about 100 U/ml.

The culture media employed maintains rat ES cells. As such, in specific embodiments, the culture media employed in the various method and compositions will maintain the pluripotency of all or most of (i.e., over 50%) of the rat ES cells in a cell line for a period of a at least 5, 10 or 15 passages. In one embodiment, the culture media comprises one or more compounds that assist in maintaining pluripotency. In one embodiment, the culture media comprises a MEK pathway inhibitor and a glycogen synthase kinase-3 (GSK-3) inhibitor. The media can further comprise additional components that aid in maintaining the ES cells, including for example, FGF receptor inhibitors, ROCK inhibitors, and/or ALK (TGFb receptor) inhibitors. A non-limiting example of an FGF receptor inhibitors includes PD184352. A non-limiting example of a ROCK inhibitor includes Y-27632, and non-limiting example of an ALK (TGFb receptor) inhibitor includes A-83-01. In specific embodiments, 2i media (table 2) is used with 10 uM ROCKi when thawing cryopreserved rESC or when re-plating rESC after dissociation with trypsin.

In other embodiments, the media comprises a combination of inhibitors consisting of a MEK pathway inhibitor and a glycogen synthase kinase-3 (GSK-3) inhibitor.

In one non-limiting embodiment, the culture media comprises a GSK-3 inhibitor comprising CHIR99021 and/or comprises a MEK inhibitor comprising PD0325901. In other embodiments, the media comprises a combination of inhibitors consisting of CHIR99021 and PD0325901. Either of these compounds can be obtained, for example, from Stemgent. In specific embodiments, CHIR99021 is present in the culture media at a concentration of about 0.5µ to about 3 µM, about 0.5µ to about 3.5 µM, about 0.5 µM to about 4 µM, about 0.5 µM to about 1 µM, about 1 µM to about 1.5 µM, about 1.5 µM to about 2 µM, about 2 µM to about 2.5 µM, about 2.5 to about 3 µM, 3 µM to about 3.5 µM. In further embodiments, CHIR99021 is present in the culture media at a concentration of about 3 µM. In other embodiments, PD0325901 is present in the culture media at a concentration of about 0.4 µM to about 1 uM, about 0.4 µM to about 1.5 uM, about 0.4 µM to about 2 µM, about 0.4 µM to about 0.8 µM, 0.8 µM to about 1.2 µM, about 1.2 to about 1.5 µM. In further embodiments, PD0325901 is present in the culture media at a concentration of about 1 µM. In specific embodiments, CHIR99021 is present in the culture media at a concentration of about 3 µM and PD0325901 is present at a concentration of about 1 µM.

In one non-limiting embodiment, the culture media employed in the various methods and compositions disclosed herein is set forth in Table 2. Within the context of this application, the media described in Table 2 is referred to as 2i media.

TABLE 2

Non-limiting rat ES culture media.

| Reagent | Concentration |
| --- | --- |
| DMEM/F12 basal media | 1x (50%) |
| Neurobasal media | 1x (50%) |
| Penicillin/streptomycin | 1% |
| L-Glutamine | 4 mM |
| 2-Mercaptoethanol | 0.1 mM |
| N2 supplement | 1x |
| B27 supplement | 1x |

TABLE 2-continued

Non-limiting rat ES culture media.

| Reagent | Concentration |
| --- | --- |
| LIF | 100 U/ml |
| PD0325901 (MEK inhibitor). | 1 µM |
| CHIR99021 (GSK inhibitor). | 3 µM |

Additional media that can be employed include those disclosed in Li et al. (2008) *Cell* 135:1299-1310, Yamamoto et al. (2012) *Transgenic Rats* 21:743-755, Ueda et al. (2008) *PLoS ONE* 3(6):e2800, Meek et al. (2010) *PLoS ONE* 4 (12): e14225; Tong et al. (2010) *Nature* 467:211-213; US Patent Publication 2012/0142092, Buehr et al. (2008) *Cell* 135:1287-1298, Li et al. (135) *Cell* 1299-1310, each of which is herein incorporated by reference in their entirety. When employing such media, the concentration and the source of LIF can be modified as outlined herein. In specific embodiments, the various culture media are used in combination with mouse LIF or an active variant or fragment thereof, and in even further embodiments, the various culture media comprise a mouse LIF or an active variant or fragment thereof at a concentration of about 50 U/ml to about 100 U/ml, about 50 U/ml to about 150 U/ml, or about 100 U/ml.

The temperature of the cultures of rat ES cells, both for the production of the ES cell line and for the culturing and maintaining of the ES line it typically carried out at about 35° C. to about 37.5° C. In specific embodiment, the temperature is 37.0° C. The culture is typically carried out at 7.5% $CO_2$.

ii. Establishing a Rat ES Cell Line

Methods for generating a rat embryonic stem (ES) cell line are provided. Such methods comprises (a) culturing in vitro a first feeder cell layer and a morula-stage embryo, a blastocyst-stage embryo, or a rat embryo at a developmental stage between a morula-stage embryo and a blastocyst-stage embryo, wherein the zona pellucida of the rat embryo has been removed and wherein the culture conditions maintain pluripotency of the rat ES cell and comprises a media having mouse leukemia inhibitory factor (LIF) or an active variant or fragment thereof; and, (b) transferring an outgrowth of an amorphous undifferentiated mass of rat ES cells to an in vitro culture well comprising a second feeder cell layer and culturing the outgrowth under conditions that maintain pluripotency of the rat ES cells and comprises a media having mouse LIF or an active variant or fragment thereof, and thereby establishing a rat ES cell line. The various methods further comprise passaging and culturing in vitro the cells of the rat ES cell line, wherein each subsequent in vitro culturing comprises culturing the rat ES cells on the feeder cell layer under conditions that maintain pluripotency of the rat ES cells and comprises a media having mouse LIF or an active variant or fragment thereof. Rat ES cell lines made by such methods are also provided.

Non-limiting examples of methods to establish a rat ES cell line having the various characteristics discussed herein are set forth in Example 3. Briefly, a rat embryo (i.e., a morula-stage embryo, a blastocyst-stage embryo, or a rat embryo at a developmental stage between a morula-stage embryo and a blastocyst-stage embryo) is flushed from the uteruses of a female rat. In specific embodiments, a blastocyst or an 8 cell embryo is obtained. The zona pellucida is removed and the rat embryos are cultured on feeder cells (as discussed elsewhere herein) which, in specific embodiments, comprise a monolayer of mitotically inactivated mouse embryonic fibroblasts (MEFs). The cells of the morula-stage embryo, the blastocyst-stage embryo, or the rat embryo at a developmental stage between a morula-stage embryo and a blastocyst-stage embryo are cultured in vitro under conditions that maintain the ES rat cells and thereby are sufficient to maintain pluripotency and/or totipotency of the ES cells. Various media can be employed at this stage, including any of the various media discussed above which have LIF, including mouse LIF or an active variant or fragment thereof, in the media.

The cultures are monitored for the presence of an outgrowth (an amorphous undifferentiated mass of cells). Once the outgrowth reaches an appropriate size, a given outgrowth is transferred to new feeder plate and cultured. Transfer is accompanied by enzymatic dissociation using trypsin in order to produce multiple colonies. This transfer is commonly referred to as "passage 1". The speed at which each line expands varies. The media is changed as needed in order to maintain the pluripotency or totipotency of the rat ES cells. The culture is monitored for the presence of colonies having embryonic stem cell morphology. Such morphology includes one or more of the following characteristics: (a) round, circular mounds that rise above the monolayer of feeder cells; (b) cells that are packed tightly together such that cell boarders are difficult to see; (c) smaller cell size; (d) small amount of cytoplasm and enlarged nucleus, (e) form sphere-like colonies when plated on feeder cells in vitro. Once such colonies appear, the culturing can continue until reaching approximately 50% confluency. The colonies are then transferred to a new feeder plate. Transfer is accompanied by enzymatic dissociation using trypsin in order to expand the number of colonies. This is referred to as "passage 2". The cells are continued to be cultured with feeder cells until they reach approximately 50% confluent, at which point the cells can undergo further passages to maintain the cell lines or the lines can be frozen. See, also Tong et al. (2010) *Nature* 467 (9):211-215; Li et al. (2008) *Cell* 135:1299-1310, and Buehr et al. (2008) *Cell* 135:1287-1298, each of which is herein incorporated by reference. Thus, in specific embodiments, the various rat ES cells, cell lines and cell populations disclosed herein are capable of being subcultured and maintaining the undifferentiated state.

In one non-limiting embodiment, the derivation of the rat ES cells occurs as follows. At day 0, female rats are euthanized and the oviducts and uterine horns are dissected out and place into a tissue culture dish containing warm N2B27 media. Media is flushed through the uterine horns and oviducts to eject blastocysts into the media. The blastocysts are collected and transfer to embryo culture dish containing KSOM+2i (1 µMPD0325901, 3 µM CHIR99021). KSOM can be purchased from Millipore, catalog number is MR-106-D. The 2i media referred to herein comprises the media set forth in Table 2. The cells are culture overnight at 37° at 7.5% $CO_2$.

In other non-limiting embodiments, the rat ES cells are derived from 8-cell embryos or frozen 8-cell embryos. The embryos are cultured in M2 medium for 10 minutes at room temperature and are then transfer to KSOM+2i and culture overnight.

A non-limiting example for derivation of the rat ES cells is as follows: on Day 1, transferring cavitated embryos to 2i medium (Table 2) and culture overnight. The culturing is continued un-cavitated in KSOM+2i. On day 2, all remaining embryos are transferred to 2i medium, whether or not they have cavitated. Culture continues overnight in 2i medium. On day 3, embryos are incubated with acid tyrodes to remove the zona pellucida and washed 3 times in 2i medium to remove the acid tyrodes. Each embryo is deposited into a separate well feeder plate, in which each well contains a monolayer of mitotically inactivated mouse embryonic fibroblasts (MEFs). The cells are cultured overnight in 2i medium. On day 4 and 5, the cells plated embryos are monitored for the presence of an outgrowth, an amorphous undifferentiated mass of cells. Outgrowths are ready for transfer when they are approximately twice the size of the plated embryo. Each day, spent media is removed and replaced with fresh 2i media. The outgrowths are transferred to new feeder wells, and again spent media is removed and the wells are washed with PBS. The PBS is removed and trypsin is added and incubated for about 10 minutes. The trypsin reaction is stopped by the addition of 30 µl 2i media and 10% FBS. The cells are gently dissociated and the entire content is transferred to a well in a feeder plate. This is referred to as Passage 1 (P1). The cells are cultured overnight in 2i medium. On day 5-8, depending on how fast each line expands, the 2i media is changed each day and culture is monitored for the presence of colonies with an ESC morphology. Such ESC morphology is discussed in detail elsewhere herein. Culturing continues until colonies expand to about 50% confluency. The colonies are then trypsinized and passaged as before into feeder wells. This is referred to as passage 2. Feeding and monitoring each line is continued until they are approximately 50% confluent. The cells are trypsinized as usual. The trypsin is stopped with 2i media+ 10% FBS. The cells are pelleted by centrifugation, and the cells in 400 µl Freezing Medium (70% 2i, 20% FBS, 10% DMSO). The cells can then be frozen. This is referred to passage 3.

iii. Maintaining and Passaging a Rat ES Cell Line

Further provided are methods for maintaining or culturing a rat embryonic stem cell line. The method comprises culturing in vitro a feeder cell layer and a rat ES cell line, wherein the culture conditions maintain pluripotency of a rat embryonic stem (ES) cell and comprise a media having mouse leukemia inhibitory factor (LIF) or an active variant or fragment thereof. Such methods employ the culture media and feeder cell layer as outlined above. In one embodiment, the rat ES cell line can be passaged at least 5, 6, 7, 8, 9, 10, 11, 12, 13, 14, 15, 16, 17, 18, 19, 20, 21, 22, 23, 24, 25, 30, 40, 50 or more times. In specific embodiments, the rat ES cells can be passaged up to at least 11 times in a medium comprising a GSK3 inhibitor and a MEK inhibitor without decreasing its targeting efficiency or germline transmission efficiency of a targeted genetic modification.

The rat ES cell lines are fed and monitored. In specific embodiments, passage occurs when the culture is approximately 30%, 40%, 50%, or 60% confluent. In other embodiments, passage occurs when the culture is 50% confluent. Depending on how fast each line expands, the passages can occur every 24, 25, 26, 27, 28, 29, 30, 40, 45, 50, 55, 60, 65, 70, 75, 80, 90, 95 or 100 hours. In other embodiments, the time between passages ranges between 24 hours and 96 hours, between about 30 and 50 hours, between about 25 and 75 hours, between about 50 and 96 hours, between about 25 and 75 hours, between about 35 and 85 hours, or between about 40 and 70 hours. In one embodiment, the rat ES cell, cell line or cell population as disclosed herein has a doubling time ranging from about 24 hours to about 36 hours. In one embodiment, the rat ES cell has a doubling time of 25 hours.

The various rat ES cell lines when derived and maintained as outlined herein can have one or more any the following properties:

(a) have germ-line competency, meaning when the rat ES cell is implanted into a rat host embryo, the genome of the rat ES cell line is transmitted into an offspring;

(b) have germ-line competency following targeted genetic modification, meaning when the rat ES cell is implanted into a rat host embryo, the targeted genetic modification within the genome of the rat ES cell line, is transmitted into an offspring;

(c) have pluripotency in vitro;

(d) have totipotency in vitro;

(e) when cultured in vitro loosely adhere to a feeder cell layer;

(f) when cultured in vitro form sphere-like colonies when plated on a feeder cell layer in vitro;

(g) maintain pluripotency when cultured in vitro under conditions comprising a feeder cell layer that is not genetically modified to express leukemia inhibitory factor (LIF), wherein the culture media comprises a sufficient concentration of LIF;

(h) maintain pluripotency when cultured in vitro under conditions comprising a feeder cell layer, wherein the culture media comprises mouse LIF or an active variant or fragment thereof;

(i) comprise a molecular signature characterized by i) the expression of one or more of rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

ii) the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

iii) at least a 20-fold increase in the expression of one or more of the rat ES cell-specific genes as set forth in Table 14 when compared to a F1H4 mouse ES cell;

iv) at least a 20-fold increase in the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes as set forth in Table 14 when compared to a F1H4 mouse ES cell;

v) the expression of one or more of rat ES cell-specific genes as set forth in Table 13;

vi) the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13;

vii) at least a 20-fold increase in the expression of one or more of the rat ES cell-specific genes as set forth in Table 13 when compared to a F1H4 mouse ES cell;

viii) at least a 20-fold increase in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13 when compared to a F1H4 mouse ES cell;

ix) at least a 20-fold decrease in the expression of one or more of the rat ES cell-specific genes as set forth in Table 12 when compared to a F1H4 mouse ES cell; and/or x) at least a 20-fold decrease in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 12 when compared to a F1H4 mouse ES cell;

xi) any combination of expression of the rat ES cell-specific genes of parts (i)-(x);

xii) a relative expression level of pluripotency markers as shown in Table 15 for at least 2, 3, 4, 5, 6, 7, 8, 9, 10, 11, 12, 13, 14, 15, 16, 17 or 18 of the listed pluripotency markers. See, pluripotency ranking column of Table 15 for relative expression levels;

xiii) a relative expression level of the mesodermal markers as shown in Table 15 for at least 2, 3, or 4 of the listed mesodermal markers. See, mesodermal ranking column in Table 15 for relative expression levels;

xiv) a relative expression level of endodermal markers as shown in Table 15 for at least 2, 3, 4, 5, or 6 of the listed endodermal markers. See, endodermal ranking column in Table 15 for relative expression levels;

xv) a relative expression level of neural markers as shown in Table 15 for at least 2 and 3 of the listed neural markers. See, neural ranking column in table 15 for relative expression levels;

xvi) a relative expression level of trophectoderm markers as shown in Table 15 for the listed trophectoderm markers. See, trophectoderm ranking column in table 15 for relative expression levels;

xvii) any relative expression level of one or more (2, 3, 4, 5, 6, 7, 8, 9, 10, 11, 12, 13, 14, 15, 16, 17, 18, 19, 20, 21, 22, 23, 24, 25, 26, 27, 28, 29 or 30) of the pluripotency markers, mesodermal markers, endodermal markers, neural markers and/or trophectoderm markers set forth in Table 15;

xviii) the relative expression level of each of the markers set forth in table 15;

xix) any combination of the signatures set forth in xii-xiix; and/or xx) any combination of the signature set forth in i-xiix;

(j) have the ability to produce a F0 rat;

(k) capable of being subcultured and maintaining the undifferentiated state;

(l) have the same number of chromosomes a normal rat cell; and/or (m) maintain pluripotency in vitro without requiring paracrine LIF signaling.

(n) have self renewal, meaning they divide indefinitely while maintaining pluripotency.

Such properties of a given rat ES cell line can be present at any one of the passage, including at passages 5, 6, 7, 8, 9, 10, 11, 12, 13, 14, 15, 16, 17, 18, 19, 20, 21, 22, 23, 24, 25, 30, 40, 50 or later.

Thus, in one non-limiting embodiment, an in vitro culture comprising a feeder cell layer and a population of rat ES cells is provided, wherein the in vitro culture conditions maintain pluripotency of the rat ES cells and comprises a media having mouse leukemia inhibitory factor (LIF) or an active variant or fragment thereof. In specific embodiments, the rat ES cells cultured under such conditions maintains pluripotency of at least 50% of cell population over a period of at least 10 passages, maintains pluripotency of at least 60% of cell population over a period of at least 10 passages, maintains pluripotency of at least 70% of cell population over a period of at least 10 passages, maintains pluripotency of at least 75% of cell population over a period of at least 10 passages, maintains pluripotency of at least 80% of cell population over a period of at least 10 passages, maintains pluripotency of at least 85% of cell population over a period of at least 10 passages, maintains pluripotency of at least 90% of cell population over a period of at least 10 passages, or maintains pluripotency of at least 95% of cell population over a period of at least 10 passages.

Further provided herein are in vitro cultures comprising the various rat ES cells, cell populations and cell lines disclosure herein, as well as, culturing kits for these various ES cells. For example, as discussed above, in specific embodiments, the various rat ES cells provided herein have a one or more of the following characteristics: (1) when cultured in vitro loosely adhere to a feeder cell layer; (2) when cultured in vitro they form sphere-like colonies when plated on a feeder cell layer in vitro; (3) they maintain pluripotency when cultured in vitro under conditions comprising a feeder cell layer that is not genetically modified to express leukemia inhibitory factor (LIF), wherein the culture media comprises a sufficient concentration of LIF; and/or (4) they capable of being subcultured and maintaining the undifferentiated state. Moreover, the rat ES cell populations of any of these in vitro cultures can comprise, for example, a population of cells in which at least 70%, 75%, 85%, 90%, 91%, 92%, 93%, 94%, 95%, 96%, 97%, 98%, 99% or 100% of the cells within the population are euploid, are diploid and/or have 42 chromosomes.

One method of culturing a rat embryonic stem cells in vitro comprises (a) providing an in vitro culture comprising a feeder cell layer and a population of isolated rat embryonic stem (ES) cells; and (b) culturing the in vitro culture under conditions which are sufficient to maintain pluripotency or totipotency of the isolated rat embryonic stem (ES) cell, and wherein the rat ES cells form colonies that loosely adhere to the feeder cell layer. "Loose adherence" or "adhere loosely" means that, if the culture dish is undisturbed for a period of time (minimum 8 hours), some colonies will adhere to the feeders such that they can maintain adherence if the dish is gently moved. In smaller wells (where the media moves less), loose adherence can happen faster. In either case, these colonies can be dislodged by either a) swirling the media in the dish or by gently pipetting media across the surface of the feeders. The morphology of these loosely adherent colonies is still spherical. In such instances the rat ES cells form sphere-like colonies when plated on a feeder cell layer in vitro. Such sphere-like colonies are shown for example in FIG. 1.

iv. Kits and In Vitro Cultures

The rat ES cells and rat ES cell lines provided herein can be contained within a kit or an article of manufacture. In specific embodiments, the kit or article of manufacture comprises any of the rat ES cell lines or populations disclosed herein. The kit can further comprise any culture media that maintains the rat ES cell, including media that maintains the pluripotency of the rat ES cells. Such media can comprise culture media having mouse LIF or an active variant or fragment thereof, as discussed in greater detail elsewhere herein. The media within the kit can further comprise a MEK inhibitor and a GSK-3 inhibitor, or alternatively, the media within the kit can further comprise a combination of inhibitors consisting of a MEK inhibitor and a GSK-3 inhibitor. In specific embodiments, the media in the kit comprises a MEK inhibitor comprising PD0325901 and/or a GSK-3 inhibitor comprising CHIR99021. Any of the various media discussed herein, can be contained within the kit.

Further provided is a kit or article of manufacture that comprises any of the rat ES cell lines or populations disclosed herein, any of the various media disclosed herein, and a population of feeder cells. In one embodiment, the feeder cells in the kit or article of manufacture are not genetically modified to express LIF and/or the feeder cells comprises mitotically inactivated mouse embryonic fibroblasts (MEFs). Any of the other feeder cells disclosed herein can be employed in the kit or article of manufacture.

IV. Genetic Modification of Rat Embryonic Stem (ES) Cells

The various rat ES cells and cell lines disclosed herein can be modified to contain at least one targeted genetic modification. Thus, various methods are provided for genetically modifying an isolated rat embryonic stem (ES) cell as disclosed herein. The method comprises introducing into the genome of an isolated rat ES cell disclosed herein a targeted genetic modification to form a genetically modified rat ES cell. The targeted genetic modification can comprise any modification to the genome of rat ES including, for example, an insertion, a deletion, a knockout, a knockin, a mutation, or a combination thereof. In one embodiment, the targeted genetic modification comprises insertion of a heterologous polynucleotide into the genome of the rat ES cell. As used herein, "heterologous" in reference to a sequence is a sequence that originates from a foreign species, or, if from the same species, is substantially modified from its native form in composition and/or genomic locus by deliberate human intervention.

In one aspect, an isolated rat ES cell or rat ES cell line is provided that is capable of sustaining pluripotency following one or more genetic modifications in vitro and that is capable of transmitting a genetically modified genome to a germline of an F1 generation. Thus, the rat ES cell maintains its pluripotency to develop into a plurality of cell types following the one or more serial genetic modifications in vitro (e.g., two, three, four, five, or six or more serial genetic modifications). In other embodiments, multiple targeted genetic modifications are made in a given rat ES cell, including, for example, 2, 3, 4, 5, 6, 7, 8, 9, 10, 11, 12, 13 14, 15 or more. As such, multiple heterologous polynucleotides can also be integrated into the genome, including for example, 2, 3, 4, 5, 6, 7, 8, 9, 10, 11, 12, 13 14, 15 or more.

In one embodiment, following any one of the one to 15 serial genetic modifications, the genetically modified rat ES cells upon exposure to differentiation medium are capable of differentiation into a plurality of cell types. In one embodiment, following any one of the one to 15 serial genetic modifications, the genetically modified rat ES cells are capable of being maintained in an undifferentiated state in culture. In one embodiment, the genetically modified and cultured rat ES cells in the undifferentiated state, when employed as donor cells in a rat host embryo, populate the embryo and form a blastocyst comprising the one to fifteen genetic modifications. In one embodiment, the blastocyst, when implanted into a surrogate mother under conditions suitable for gestation, develops into an F0 rat progeny that comprises the one to 15 genetic modifications.

Various methods for making targeted genetic modifications within a genome of a rat ES cell can be used. For example, in one instance, the targeted genetic modification employs a system that will generate a targeted genetic modification via a homologous recombination event. In other instances, the rat ES cells can be modified using nuclease agents that generate a single or double strand break at a targeted genomic location. The single or double-strand break is then repaired by the non-homologous end joining pathway (NHEJ). Such systems find use, for example, in generating targeted loss of function genetic modifications. See, for example, Tesson et al. (2011) Nature Biotechnology 29:695-696, herein incorporated by reference. Such agents include, Transcription Activator-Like Effector Nuclease (TALEN) (WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res.* (2010) doi:10.1093/nar/gkq704; and Miller et al. (2011) *Nature Biotechnology* 29:143-148; US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference); a zinc-finger nuclease (ZFN) (US20060246567; US20080182332; US20020081614; US20030021776; WO/2002/057308A2; US20130123484; US20100291048; and, WO/2011/017293A2, each of which is herein incorporated by reference); a meganuclease (see, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346); and a CRISPR/Cas system (Mali P et al. (2013) *Science* 2013 Feb. 15; 339(6121):823-6; Jinek M et al. *Science* 2012 Aug. 17; 337(6096):816-21; Hwang W Y et al. *Nat Biotechnol* 2013 March; 31(3):227-9; Jiang W et al. *Nat Biotechnol* 2013 March; 31(3):233-9; and, Cong L et al. *Science* 2013 Feb. 15; 339(6121):819-23, each of which is herein incorporated by reference).

In other embodiments, the targeted genomic modification can be made by employing a homologous recombination targeting vector. In such instances, the targeting vector comprises the insert polynucleotide and further comprises an upstream and a downstream homology arm which flank the insert polynucleotide. The homology arms which flank the insert polynucleotide correspond to genomic regions within the targeted genomic locus. For ease of reference, the corresponding genomic regions within the targeted genomic locus are referred to herein as "target sites". Thus, in one example, a targeting vector can comprise a first insert polynucleotide flanked by a first and a second homology arm corresponding to a first and a second target site located at the targeted genomic locus. The targeting vector thereby aids in the integration of the insert polynucleotide into the targeted genomic locus through a homologous recombination event that occurs between the homology arms and the corresponding target sites within the genome of the cell.

As used herein, a homology arm and a target site "correspond" or are "corresponding" to one another when the two regions share a sufficient level of sequence identity to one another to act as substrates for a homologous recombination reaction. By "homology" is meant DNA sequences that are either identical or share sequence identity to a corresponding sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100% sequence identity, such that the sequences undergo homologous recombination. Moreover, a corresponding region of homology between the homology arm and the corresponding target site can be of any length that is sufficient to promote homologous recombination at the cleaved recognition site.

In specific embodiments, the isolated rat ES cell, cell line or cell population exhibits a homologous recombination efficiency of at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, at least 50%, at least 55%, at least 60%, at least 65%, at least 70%, at least 75%, or at least 80%. In one embodiment, the homologous recombination efficiency employing the rat ES cell is greater than 4%.

In specific embodiments, a selection marker is employed when generating a targeted genetic modification in a rat ES cell. The polynucleotide encoding the selection marker can be present on the targeting vector which is designed to introduce the targeted genetic modification into the genome, or it can be found on a separate plasmid or vector. The polynucleotide encoding the selection marker can be contained within in expression cassette. The various components of such expression cassettes are discussed in further detail elsewhere herein. Various selection markers can be used in the methods and compositions disclosed herein. Such selection markers can, for example, impart resistance to an antibiotic such as G418, hygromycin, blastocidin, puromycin or neomycin. Such selection markers include neomycin phosphotransferase (neo$^r$), hygromycin B phosphotransferase (hyg$^r$), puromycin N-acetyltransferase and blasticidin S deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hahypoxanthine-guanine phosphoribosyltransferase (HG-PRT) or herpes simplex virus thymidine kinase (HSV-TK). See, for example, Santerre et al. (1984) *Gene* 30:147-56; Joyner (1999) *The Practical Approach Series*, 293; Santerre et al. (1984) *Gene* 30:147-56; Bernard et al. (1985) *Exp Cell Res* 158:237-43; Giordano and McAllister (1990) *Gene,* 88:285-8; Izumi et al. (1991) *Exp Cell Res* 197:229-33), each of which is herein incorporated by reference in their entirety. In specific embodiments, the neoR selectable marker is the neomycin phosphotransferase (neo) gene of Beck et al. (1982) *Gene,* 19:327-36, which is herein incorporated by reference. The neoR selection maker is that used in U.S. Pat. No. 7,205,148 or 6,596,541, each of which are herein incorporated by reference.

In specific embodiments, the selection marker employed is a non-attenuated selection marker. A "non-attenuated selection marker" comprises a selection marker that retains the activity of the native polypeptide or the selection marker has an increased activity when compared to the native form of the polypeptide. An increased in activity of a selection marker can comprise any statistically significant increase in activity including, for example, an increase of at least 5%, 10%, 20%, 30%, 40%, 50%, 60%, 70% 80% or higher. Thus, a non-attenuated selection marker when expressed in a host cell will allow for a higher percentage of the host cells to survive in the presence of a higher concentration of the selection agent than when employing an attenuated selection marker. Non-attenuated selection markers include, for example, a neomycin non-attenuate selection marker. See, for example, Beck et al. (1982) *Gene,* 19:327-36 or in U.S. Pat. No. 7,205,148 or 6,596,541, each of which are herein incorporated by reference.

In other instances, the increased activity of a selection marker when compared to an attenuated selection marker and/or the wild type (native) selection marker can result from increasing the copy number of either the non-attenuated, attenuated or native selection marker within the genome of the rat ES cell. As such, a given rat ES cell can comprise within its genome at least 1, 2, 3, 4, 5, 6, 7, 8, 9, 10 or more copies of a given selection marker (i.e., a non-attenuated selection marker, an attenuated selection marker or a native (wildtype) selection marker).

The various selection markers employed are encoded by a polynucleotide operably linked to a promoter active in the rat ES cell. In specific embodiments, the increase in the activity of the selection marker can result from an increase in expression of the selection marker. Thus, a promoter can be employed to elevate the expression levels of a given selection marker. Promoters of interest include, but are not limited to, the CMV promoter, the PGK promoter and the CAG promoter. In one embodiment, the human Ubiquitin (hUb) promoter is used to express the selection marker. See, Valenzuela et al. (2003) *Nature Biotechnology* 21:652-659, herein incorporate by reference in its entirety.

In one embodiment, the rat ES cell maintains its pluripotency to develop into a plurality of cell types following a single round of electroporation with an exogenous nucleic acid. In another embodiment, the rat ES cell maintains its pluripotency to develop into a plurality of cell types following a second round of electroporation with an exogenous nucleic acid, following a third round of electroporation with an exogenous nucleic acid, following a fourth round of electroporation with an exogenous nucleic acid, following a fifth round of electroporation with an exogenous nucleic acid, following a sixth round of electroporation with an exogenous nucleic acid, following a seventh round of electroporation with an exogenous nucleic acid, following an eighth round of electroporation with an exogenous nucleic acid, following a ninth round of electroporation with an exogenous nucleic acid, following a tenth round of electroporation with an exogenous nucleic acid, following an eleventh round of electroporation with an exogenous nucleic acid, following a twelfth round of electroporation with an exogenous nucleic acid, following a thirteenth round of electroporation with an exogenous nucleic acid, following a fourteenth round of electroporation with an exogenous nucleic acid and/or following a fifteenth round of electroporation with an exogenous nucleic acid. In other embodiments, the rat ES cell is capable of transmitting a targeted genetic modification into progeny following a successive round of electroporation (i.e., at least 1, 2, 3, 4, 5, 6, 7, 8, 9, 10 or more rounds of electroporation).

i. Introducing Sequences into a Rat Embryonic Stem Cell

The methods provided herein comprise introducing into a cell with one or more polynucleotides or polypeptide constructs comprising the various components needed to make the targeted genomic modification. "Introducing" means presenting to the cell the sequence (polypeptide or polynucleotide) in such a manner that the sequence gains access to the interior of the cell. The methods provided herein do not depend on a particular method for introducing any component of the targeted genomic integration system into the cell, only that the polynucleotide gains access to the interior of a least one cell. Methods for introducing polynucleotides into various cell types are known in the art and include, but are not limited to, stable transfection methods, transient transfection methods, and virus-mediated methods. Such method include, but are not limited to, electroporation, intracytoplasmic injection, viral infection (including adenovirus, lentivirus, and retrovirus vectors), transfection, lipid-mediated transfection and/or Nucleofaction™. See, for example, Stadtfeld et al. (2009) *Nature Methods* 6(5):329-330; Yusa et al. (2009) *Nat. Methods* 6:363-369; Woltjen et al. (2009) Nature 458, 766-770. Such methods include, but are not limited to, direct delivery of DNA such as by ex vivo transfection (Wilson et al., Science, 244:1344-1346, 1989, Nabel and Baltimore, Nature 326:711-713, 1987), optionally with Fugene6 (Roche) or Lipofectamine (Invitrogen), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, J. Cell Biol., 101:1094-1099, 1985; U.S. Pat. No. 5,789,215, incorporated herein by reference); by electroporation (U.S. Pat. No. 5,384,253, incorporated herein by reference; Tur-Kaspa et al., Mol. Cell Biol., 6:716-718, 1986; Potter et al., Proc. Nat'l Acad. Sci. USA, 81:7161-7165, 1984); by calcium phosphate precipitation (Graham and Van Der Eb, Virology, 52:456-467, 1973; Chen and Okayama, Mol. Cell Biol., 7(8):2745-2752, 1987; Rippe et al., Mol. Cell Biol., 10:689-695, 1990); by using DEAE-dextran followed by polyethylene glycol (Gopal, Mol. Cell Biol., 5:1188-1190, 1985); by direct sonic loading (Fechheimer et al., Proc. Nat'l Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol., 149:157-176, 1987; Wong et al., Gene, 10:87-94, 1980; Kaneda et al., Science, 243:375-378, 1989; Kato et al., Biol. Chem., 266:3361-3364, 1991) and receptor-mediated transfection (Wu and Wu, Biochemistry, 27:887-892, 1988; Wu and Wu, J. Biol. Chem., 262:4429-4432, 1987); and any combination of such methods, each of which is incorporated herein by reference.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components employed to generate the targeted genomic modification.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). *Virology* 52 (2): 456-67, Bacchetti et al. (1977) *Proc Natl Acad Sci USA* 74 (4): 1590-4 and, Kriegler, M (1991). *Transfer and Expression: A Laboratory Manual*. New York: W.H. Freeman and Company. pp. 96-97); dendrimers; or cationic polymers such as DEAE-dextran or polyethylenimine. Non chemical methods include electroporation; Sono-poration; and optical transfection. Particle-based transfection include the use of a gene gun, magnet assisted transfection (Bertram, J. (2006) *Current Pharmaceutical Biotechnology* 7, 277-28). Viral methods can also be used for transfection.

A non-limiting example, of a method of introduction a heterologous polynucleotide into a rat ES cell follows. The rat ES cells, as described herein, are passaged for about 24 to about 48 prior to electroporation. About 24 hours prior to electroporation the media is changed to RVG2i+ROCKi (10 µM Y-27632). The rat ES cells are trypsinized and the rat ES cells are isolated. The rat ES cells are suspended to achieve a final cell concentration of about $2 \times 10^{\wedge}6$ to about $10 \times 10^{\wedge}6$ cells per 75 ul. About 75λ of rat ES cells are added to about 50×DNA comprising the heterologous polynucleotide and about 125λ EP buffer is added. In one non-limiting embodiment, the electroporation is carried out with the following parameters: 400V; 400V; Ω; 100 µF. The cells are then cultured in RVG2i and 10 µM ROCKi and can be transferred onto feeder cells.

ii. Selecting Rat Embryonic Stem Cells Having a Targeted Genomic Modification

Various method are provided for selecting and maintaining rat ES cells having stably incorporated into their genome a targeted genetic modification. In one non-limiting example, when introducing a heterologous polynucleotide into a rat ES cell, the method can comprise (a) providing an in vitro population of rat ES cells; (b) introducing into at least one rat ES cell a heterologous polynucleotide comprising a selection marker operably linked to a promoter active the rat ES cell; and, (c) culturing in vitro the rat ES cell population in an alternating first and second culture media wherein the first culture media comprises an effective amount of a selection agent for a first time period and the second culture media do not comprise the selection agent, wherein the in vitro culture conditions maintain pluripotency or totipotency; and thereby selecting the rat ES cell having stably integrated into its genome the heterologous polynucleotide. The various methods by which the rat ES cell having the targeted genetic modification can be selected in a given population can employ an in vitro culture system which allows the rat ES cells to maintain pluripotency. Thus, any of the in vitro culture media and feeder cells discussed herein can be employed.

In specific embodiments, the first and the second culture media are alternated about every 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 hours or more. In a specific embodiment, the first and second culture media are alternated every 24 hours.

Any appropriate selection marker can be used and the corresponding selection agent will be present at an effective concentration with the culture media. Such selection markers include any of the native, attenuated or non-attenuated selection marker discussed herein. In one embodiment, the selection marker employed imparts resistance to an antibiotic, including for example, G418. Non-limiting selection markers comprise neomycin phosphotransferase II (nptII) or hygromycin phosphotransferase (hpt).

The concentration of the selection agent is such as to allow for the selection of a rat ES cell having the selection marker while maintaining the pluripotency of the rat ES cells that are present within the culture. When employing, for example, G418, the concentration of the G418 in the selection media can range from about 50 ug/ml to about 125 ug/ml, about 60 ug/ml to about 125 ug/ml, about 70 ug/ml to about 125 ug/ml, about 80 ug/ml to about 125 ug/ml, about 90 ug/ml to about 125 ug/ml, about 100 ug/ml to about 125 ug/ml, about 110 ug/ml to about 125 ug/ml, about 80 ug/ml to about 100 ug/ml, about 65 ug/ml to about 85 ug/ml, about 70 ug/ml to about 80 ug/ml. In one embodiment, the concentration of G418 in the culture is 75 µg/ml.

The media employed in the selection allows the rat embryonic stem cells to retain pluripotency. Such media is described in detail elsewhere herein.

The selection protocol can be initiated at any time following the introduction of the polynucleotide encoding the selection marker into the genome of the rat ES cell. In specific embodiments, the selection protocol begins 10, 15, 20, 24, 30, 35, 40, 50, 60 or more hours after the introduction of the selection marker into the rat ES cell. In one embodiment, the selection protocol beings about 2 days following the introduction of the polynucleotide encoding the selection marker.

A non-limiting selection protocol employing G418 is as follows. Day 2, ($2^{nd}$ day after the introduction of the polynucleotide encoding the selection marker) the population of rat ES cells is incubated cells in 2i media and G418 at 75 µg/ml. At day 3, the population of rat ES cells are incubated cells in 2i media without G418. At day 4, the population of rat ES cells are incubated in 2i media and G418 at 75 µg/ml. At day 5, the population of rat ES cells are incubated cells in 2i media without G418. At day 6, the population of rat ES cells are incubated in 2i media and G418 at 75 µg/ml. At day 7, the population of rat ES cells is incubated in 2i media without G418. At day 8, the population of rat ES cells is incubated in 2i media without G418 and 75 µg/ml. At day 9, the population of rat ES cells is incubated cells in 2i media without G418. At day 10, the population of rat ES cells is incubated cells in 2i media and G418 at 75 µg/ml. At day 11, the population of rat ES cells is incubated cells in 2i media without G418. At day 12, colonies are picked for expansion and screening.

Following the selection of the rat ES cells having the selection marker, the colonies can be expanded. In specific embodiments, the period for expansion can be about 1, 2, 3, 4, 5, or more days in a culture condition that maintains the pluripotency of the cells. In one non-limiting embodiment, the selected colonies are expanded for 3 days. In a further embodiment, the media employed is a 2i media. Each clone can then be passed and further expanded.

The rat ES cells and cell lines having one or more of the targeted genetic modifications can have one or more any the following properties:

(a) have germ-line competency following targeted genetic modification, meaning when the rat ES cell is implanted into a rat host embryo, the targeted genetic modification within the genome of the rat ES cell line, is transmitted into an offspring;
(b) have pluripotency in vitro;
(c) have totipotency in vitro;
(d) when cultured in vitro loosely adhere to a feeder cell layer;
(e) when cultured in vitro form sphere-like colonies when plated on a feeder cell layer in vitro;
(f) maintain pluripotency when cultured in vitro under conditions comprising a feeder cell layer that is not genetically modified to express leukemia inhibitory factor (LIF), wherein the culture media comprises a sufficient concentration of LIF;
(g) maintain pluripotency when cultured in vitro under conditions comprising a feeder cell layer, wherein the culture media comprises mouse LIF or an active variant or fragment thereof;
(h) comprise a molecular signature characterized by
  i) the expression of one or more of rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;
  ii) the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes comprising Adherens Junctions Associate Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

iii) at least a 20-fold increase in the expression of one or more of the rat ES cell-specific genes as set forth in Table 14 when compared to a F1H4 mouse ES cell;
iv) at least a 20-fold increase in the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes as set forth in Table 14 when compared to a F1H4 mouse ES cell;
v) the expression of one or more of rat ES cell-specific genes as set forth in Table 13;
vi) the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13;
vii) at least a 20-fold increase in the expression of one or more of the rat ES cell-specific genes as set forth in Table 13 when compared to a F1H4 mouse ES cell;
viii) at least a 20-fold increase in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 13 when compared to a F1H4 mouse ES cell;
ix) at least a 20-fold decrease in the expression of one or more of the rat ES cell-specific genes as set forth in Table 12 when compared to a F1H4 mouse ES cell; and/or
x) at least a 20-fold decrease in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 12 when compared to a F1H4 mouse ES cell;
xi) any combination of expression of the rat ES cell-specific genes of parts (i)-(x);
xii) a relative expression level of pluripotency markers as shown in Table 15 for at least 2, 3, 4, 5, 6, 7, 8, 9, 10, 11, 12, 13, 14, 15, 16, 17 or 18 of the listed pluripotency markers. See, pluripotency ranking column of Table 15 for relative expression levels;
xiii) a relative expression level of the mesodermal markers as shown in Table 15 for at least 2, 3, or 4 of the listed mesodermal markers. See, mesodermal ranking column in Table 15 for relative expression levels;
xiv) a relative expression level of endodermal markers as shown in Table 15 for at least 2, 3, 4, 5, or 6 of the listed endodermal markers. See, endodermal ranking column in Table 15 for relative expression levels;
xv) a relative expression level of neural markers as shown in Table 15 for at least 2 and 3 of the listed neural markers. See, neural ranking column in table 15 for relative expression levels;
xvi) a relative expression level of trophectoderm markers as shown in Table 15 for the listed trophectoderm markers. See, trophectoderm ranking column in table 15 for relative expression levels;
xvii) any relative expression level of one or more (2, 3, 4, 5, 6, 7, 8, 9, 10, 11, 12, 13, 14, 15, 16, 17, 18, 19, 20, 21, 22, 23, 24, 25, 26, 27, 28, 29 or 30) of the pluripotency markers, mesodermal markers, endodermal markers, neural markers and/or trophectoderm markers set forth in Table 15;
xviii) the relative expression level of each of the markers set forth in table 15;
xix) any combination of the signatures set forth in xii-xiix; and/or
xx) any combination of the signature set forth in i-xix.

(i) have the ability to produce a F0 rat;
(j) capable of being subcultured and maintaining the undifferentiated state;
(k) having the same number of chromosomes a normal rat cell;
(l) maintain pluripotency in vitro without requiring paracrine LIF signaling; and/or
(m) have self renewal, meaning they divide indefinitely while maintaining pluripotency.

iii. Expression Cassettes

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select and propagate host cells and comprising any of the isolated nucleic acid fragments provided herein. Screening may be accomplished by Southern analysis of DNA, Northern analysis of mRNA expression, immunoblotting analysis of protein expression, or phenotypic analysis, among others.

In specific embodiments, one or more of the components described herein can be provided in an expression cassette for expression in a rat cell. The cassette can include 5' and 3' regulatory sequences operably linked to a polynucleotide provided herein. "Operably linked" means a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. The cassette may additionally contain at least one additional polynucleotide of interest to be co-introduced into the rat ES cell. Alternatively, the additional polynucleotide of interest can be provided on multiple expression cassettes.

Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

iv. Generating F0 Rat Embryos and F1 Progeny Having the Targeted Genetic Modification The various methods and compositions provided herein can be used to generate a genetically modified rat. Such methods generally comprise (a) introducing into the genome of an isolated rat ES cell disclosed herein a targeted genetic modification to form a rat ES cell having a genetic modification; (b) implanting at least one of the genetically modified rat ES cells having the genetic modification into a rat host embryo to produce a F0 embryo; (c) implanting the F0 embryo into a surrogate mother; (d) gestating the F0 embryo in the surrogate mother to term; and, (e) identifying a F0 rat having the genetic modification.

The genetically modified rat ES cells having the genetic modification can be implanted into a rat host embryo that is from the same rat strain or from a different rat strain. For example, a genetically modified DA rat ES cell can be implanted into a DA rat host embryo or it can be implanted into an SD host embryo, ACI host embryo or other heterologous rat host embryo. Similarly, a genetically modified ACI rat ES cell can be introduced into an ACI rat host embryo or it can be introduced into an SD host embryo, DA host embryo or other heterologous rat host embryo. Likewise, the surrogate mother can be from the same rat strain as the genetically modified rat cell and/or the rat host embryo or the surrogate mother can be from a different rat strain as the genetically modified rat cell and/or the rat host embryo. In one non-limiting embodiment, the genetically modified rat cell is from a DA strain, the host rat embryo is from an SD host embryo and the surrogate mother is from a DA strain. In another non-limiting embodiment, the genetically modified rat cell is from an ACI strain, the host rat embryo is from an SD strain, and the surrogate mother is from a DA strain.

In still further embodiments, the chimeric rat (F0) can be breed to produce an F1 progeny that is heterozygous for the targeted genetic modification. In addition, the male rat of the F1 progeny can be breed with a female rat of the F1 progeny to obtain an F2 progeny that is homozygous for the genetic modification.

The methods and compositions provided herein allow for at least 1%, 3%, 5%, 10%, 15%, 20%, 25%, 30%, 35%, 40%, 45%, 50%, 55%, 60%, 65%, 70%, 75% or greater of the F0 F0 rats having the genetic modification to transmit the genetic modification to the F1 progeny. In some embodiments, the rat ES cells having the targeted genetic modification are introduced into a pre-morula stage embryo from a corresponding organism, e.g., an 8-cell stage mouse embryo. See, e.g., U.S. Pat. Nos. 7,576,259, 7,659,442, 7,294,754, and US 2008-0078000 A1, all of which are incorporated by reference herein in their entireties. In other embodiments, the For, the donor rat ES cells may be implanted at 4 cell stage, 8 cell stage of the host embryo.

The rat embryos comprising the genetically modified rat ES cells is incubated until the blastocyst stage and then implanted into a surrogate mother to produce an F0. Rats bearing the genetically modified genomic locus can be identified via modification of allele (MOA) assay as described herein. The resulting F0 generation derived from the genetically modified rat ES cells is crossed to a wild-type rat to obtain F1 generation offspring. Following genotyping with specific primers and/or probes, F1 rats that are heterozygous for the genetically modified genomic locus are crossed to each other to produce a rat that is homozygous for the genetically modified genomic locus.

Further provided is a F0 rat embryo comprising an inner cell mass having at least one heterologous stem cell comprising any one of the rat ES cells provided herein. In other embodiments, progeny of a rat F0 embryo are provided wherein at least 50%, 60%, 70% or more of the F0 progeny are derived from a genetically modified rat ES cell of as disclosed herein.

In one aspect, a method for making a rat ES cell is provided, comprising deriving from a morula-stage rat embryo, a blastocyst-stage rat embryo, or a rat embryo at a developmental stage between a morula-stage embryo and a blastocyst-stage embryo a rat cell, and culturing the rat cell from the rat embryo under conditions sufficient to maintain pluripotency and/or totipotency. In on embodiment, the conditions sufficient to maintain pluripotency and/or totipotency include 2i media.

In one aspect, a method for making a genetically modified rat is provided, comprising a step of modifying a rat ES cell genome with a nucleic acid sequence of interest to form a modified rat ES cell, and employing the modified rat ES cell as a donor rat ES cell, combining the rat donor ES cell with a rat host embryo, culturing the donor ES cell and rat host embryo, and employing the cultured host embryo to make a genetically modified rat.

In one aspect, a method for making genetically modified rat F1 progeny is provided, comprising a step of modifying a rat ES cell genome with a nucleic acid sequence of interest to form a modified rat ES cell, and employing the modified rat ES cell as a donor rat ES cell, combining the rat donor ES cell with a rat host embryo, culturing the donor ES cell and rat host embryo, and employing the cultured host embryo to make a genetically modified rat, wherein the progeny are about 3%, about 10% or more, or about 63% or more derived from the genetically modified donor rat ES cell.

In one embodiment, the cultured host embryo is implanted into a surrogate rat mother, and the cultured host embryo is gestated in the surrogate mother.

In one aspect, a method of transmitting a genetic modification from a rat pluripotent cell to a rat progeny with high frequency is provided, comprising genetically modifying a pluripotent rat cell with a nucleic acid sequence of interest on a bacterial artificial chromosome to form a genetically modified rat pluripotent cell, and employing the genetically modified rat pluripotent cell with a rat host embryo in a rat surrogate mother to generate a progeny comprising the genetic modification and, optionally, breeding the progeny.

In one aspect, a method for making a rat ES cell is provided, wherein the method comprises culturing a frozen 8-cell stage embryo to a blastocyst stage, and deriving from the cultured blastocyst a rat cell, and culturing the rat cell under conditions sufficient to maintain pluripotency and/or totipotency.

V. Variants, Fragments and Sequence Identity

Active variants and fragments of the disclosed LIF polypeptide, particularly the mouse LIF polypeptide are provided herein. "Variants" refer to substantially similar sequences. As used herein, a "variant polypeptide" is intended to mean a polypeptide derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant polypeptides continue to possess the desired biological activity of the native polypeptide, that is, they inhibit the differentiation of rat and/or mouse embryonic stem cells and contribute to stem cell self-renewal. A variant of a polypeptide or disclosed herein (i.e. SEQ ID NOS: 1 or SwissProt Accession No. P09056) will typically have at least about 65%, 70%, 75%, 80%, 85%, 90%, 91%, 92%, 93%, 94%, 95%, 96%, 97%, 98%, 99% or more sequence identity with the reference sequence.

The term "fragment" refers to a portion of an amino acid comprising a specified number of contiguous amino acid. In particular embodiments, a fragment of a polypeptide disclosed herein may retain the biological activity of the full-length polypeptide and hence inhibit the differentiation of rat and/or mouse embryonic stem cells and contribute to stem cell self-renewal. Fragments of a polypeptide sequence disclosed herein (i.e. SEQ ID NOS: 1 or SwissProt Accession No. P09056) may comprise at least 10, 15, 25, 30, 50, 60, 70, 80, 90, 100, 110, 120, 130, 140, 150, 160, 170, 180, 190, 200, contiguous amino acids, or up to the total number of amino acids present in a full-length protein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" means any sequence comparison program that, for any two sequences in question, generates an alignment having identical nucleotide or amino acid residue matches and an identical percent sequence identity when compared to the corresponding alignment generated by GAP Version 10.

The following examples are offered by way of illustration and not by way of limitation.

EXAMPLES

Figure 4:
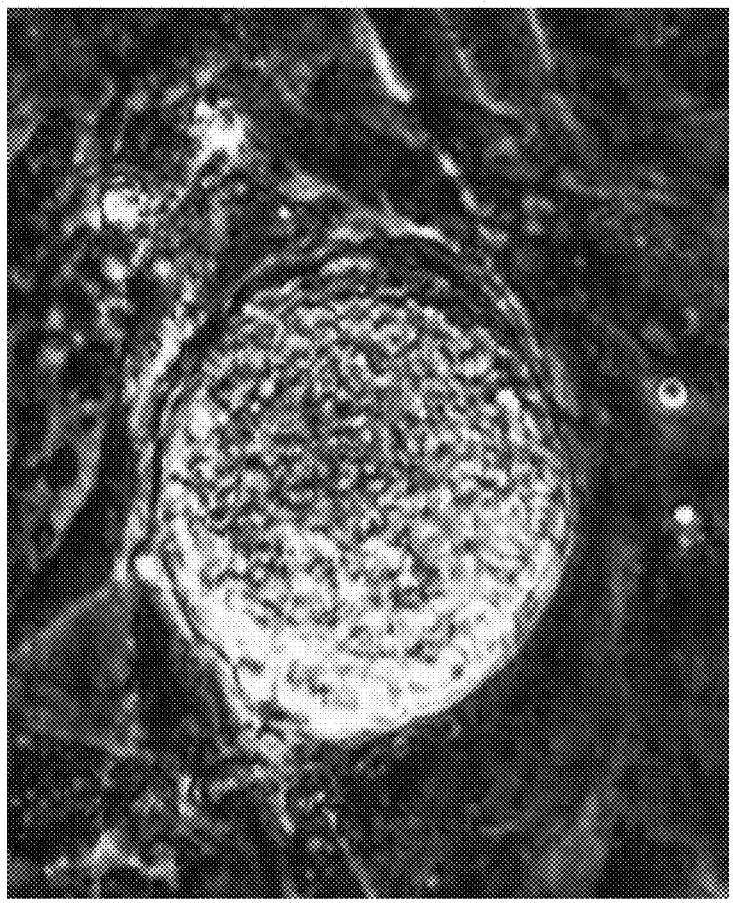
FIG. 4 depicts a closer view of a rESC of FIG. 1.

Example 1: Rat ES Cell Derivation rESC Characterization. As shown in FIG. 1, rESC grow as compact spherical colonies which routinely detach and float in the dish (close-up, FIG. 4). B, C, F, G: rESC express pluripotency markers including Oct-4 (FIG. 2A) and Sox2 (FIG. 2B), and express high levels of alkaline phosphatase (FIG. 3, left panel). Karyotype for line DA.2B is 42X,Y (FIG. 3, right panel). rESC often become tetraploid; thus, lines were pre-screened by counting metaphase chromosome spreads; lines with mostly normal counts were then formally karyotyped.

ACI blastocysts were collected from super-ovulated females obtained commercially; DA blasts were cultured from frozen 8-cell embryos obtained commercially. Zona pellucidae were removed with Acid Tyrodes and blasts were plated onto mitotically inactivated MEFs. Outgrowths were picked and expanded using standard methods. All blasts were plated, cultured and expanded using 2i media (Li et al. (2008) Germline competent embryonic stem cells derived from rat blastocysts, Cell 135:1299-1310; incorporated herein by reference).

TABLE 3

Rat ES Cell Derivation

|  | ACI | DA |
|---|---|---|
| Embryo source | Blastocysts (Superovulation) | Frozen 8-cell embryos cultured to blastocyst |
| Blastocysts plated: | 107 | 22 |
| Outgrowths: | 32 (30% of blasts) | 10 (45% of blasts) |
| Lines: | 16 (50% of outgrowths) | 9 (90% of outgrowths) |
| Karyotyped: | 3; all 42X,Y | 6: 3 42X,X<br>3 42X,Y |
| GLT validated: | 1 (ACI.G1) | 1 42X,X (DA.2C)<br>1 42X,Y (DA.2B) |

Example 2: Rat Production

Figure 5:
FIG. 5 depicts production of chimeras by blastocyst injection and transmission of the rESC genome through the germline; chimeras produced by blastocyst injection using parental ACI.G1 rESC; high percentage chimeras usually have albino snouts.
Figure 6:
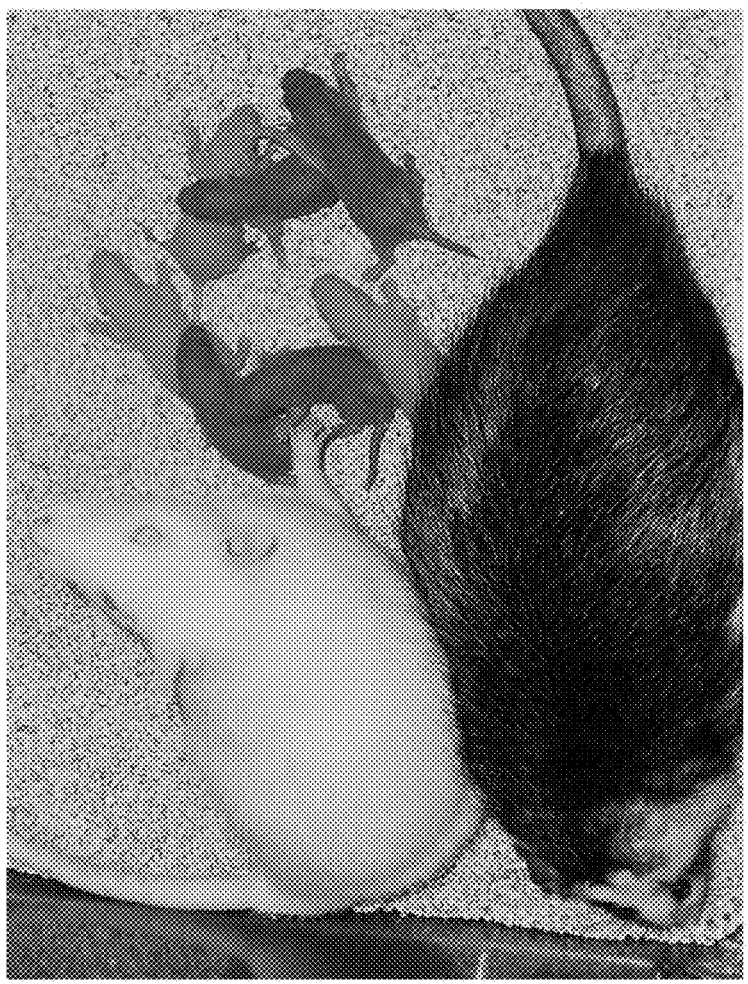
FIG. 6 depicts F1 agouti pups with albino littermates, sired by ACI/SD chimera labeled with an asterisk (*) in FIG. 5.
Figure 8A:
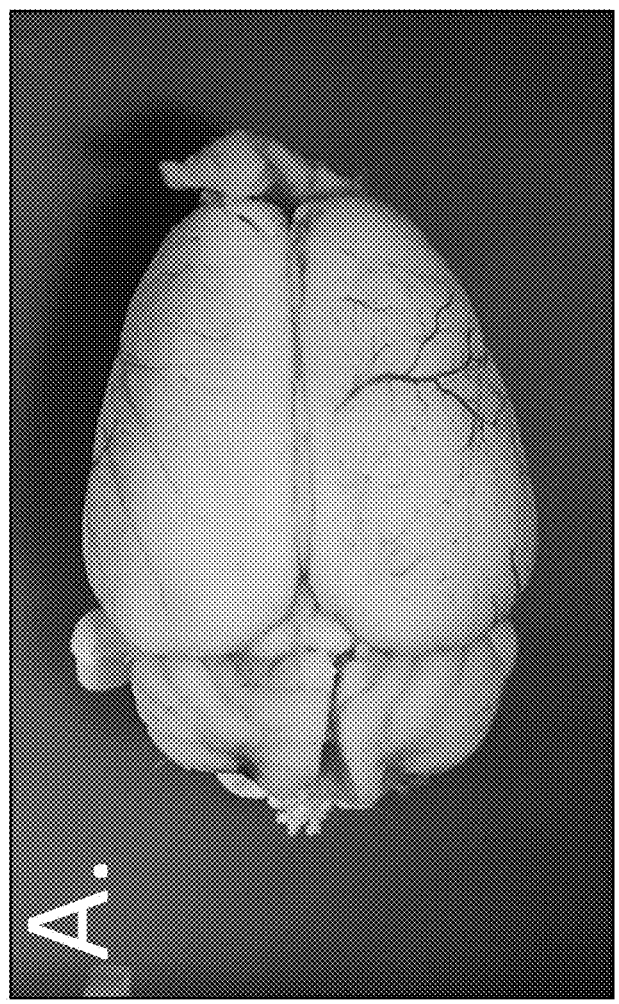
FIG. 8A depicts a control brain of a 14-week-old wild type rat, which was treated with X-gal. The control brain showed a low level of background staining for LacZ (dorsal view).
Figure 8B:
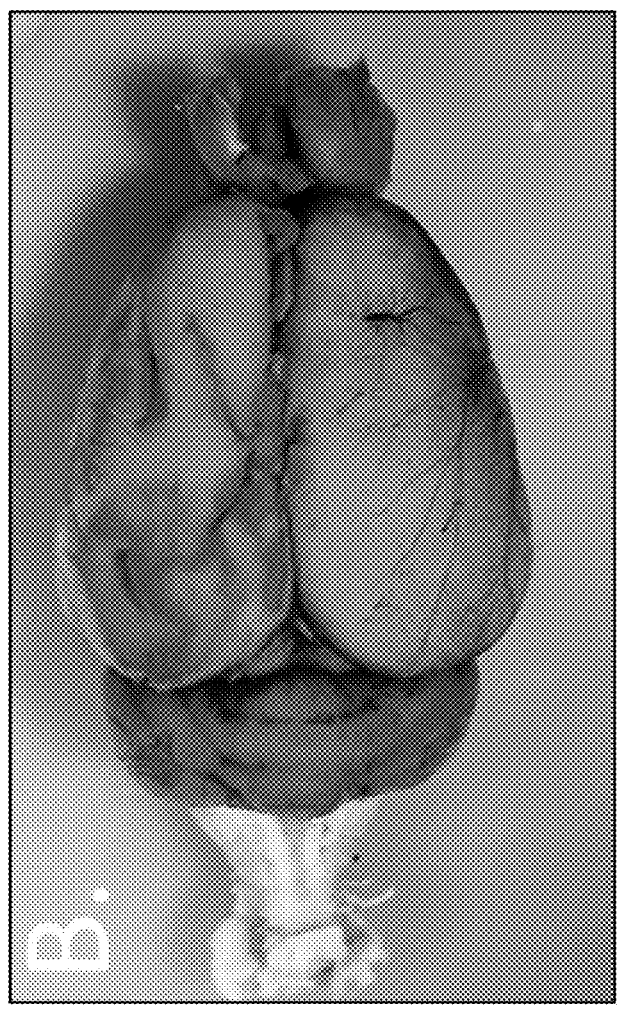
FIG. 8B depicts LacZ expression in the brain of an rRosa26 heterozygous rat (14-week old). The lacZ reporter was expressed ubiquitously throughout the brain of the rRosa26 heterozygote.
Figure 8C:
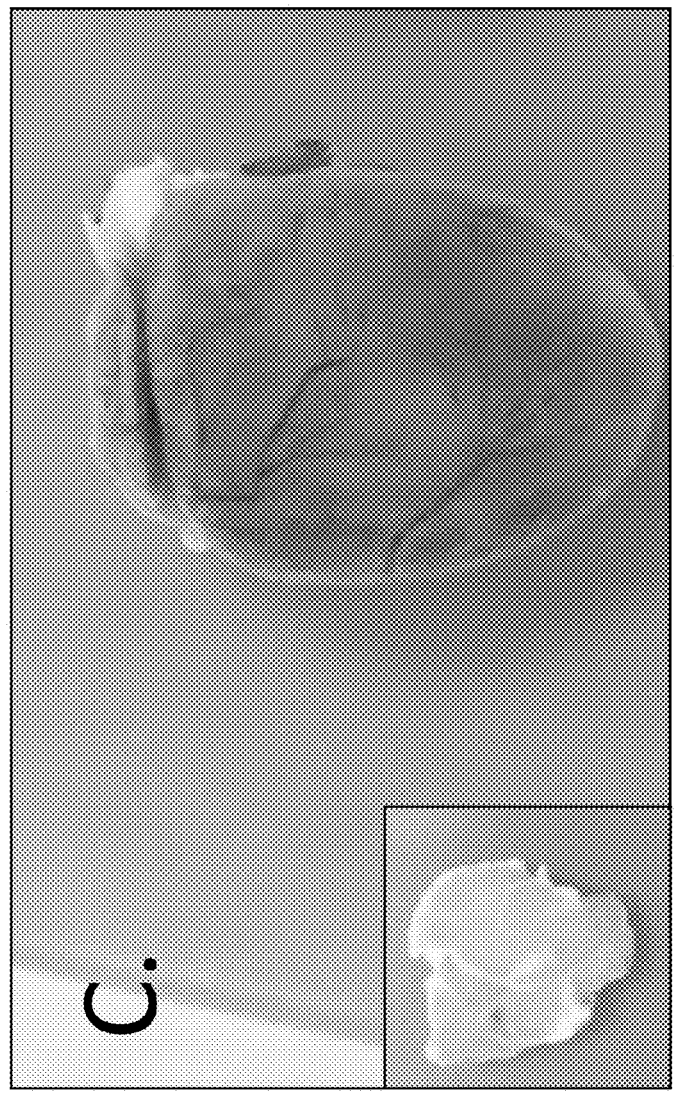
FIG. 8C depicts a control heart and thymus (inset) of a 14-week-old wild type rat, which were treated with X-gal. The control heart and thymus showed a low level of background staining for LacZ.
Figure 8D:
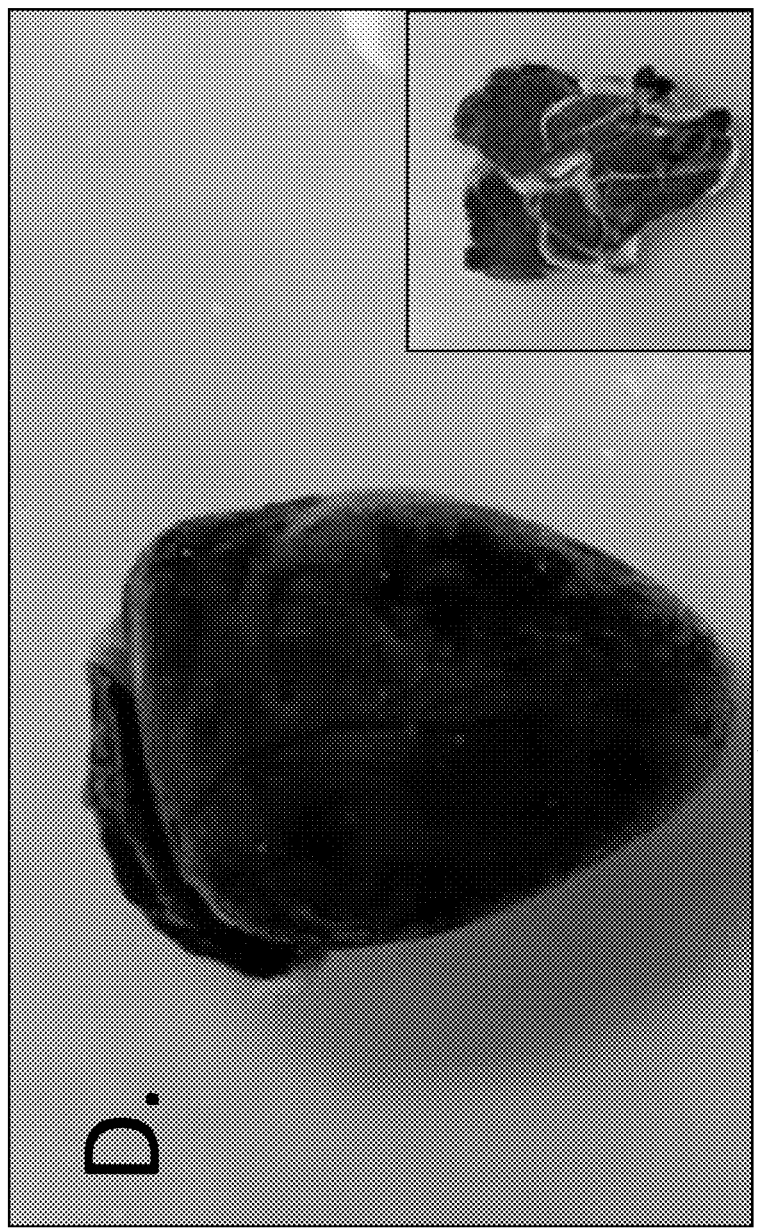
FIG. 8D depicts LacZ expression in the heart and thymus (inset) of a 14-week-old rRosa26 heterozygous rat. The lacZ reporter was expressed ubiquitously throughout the heart and thymus of the rROSA26 heterozygote.
Figure 8E:
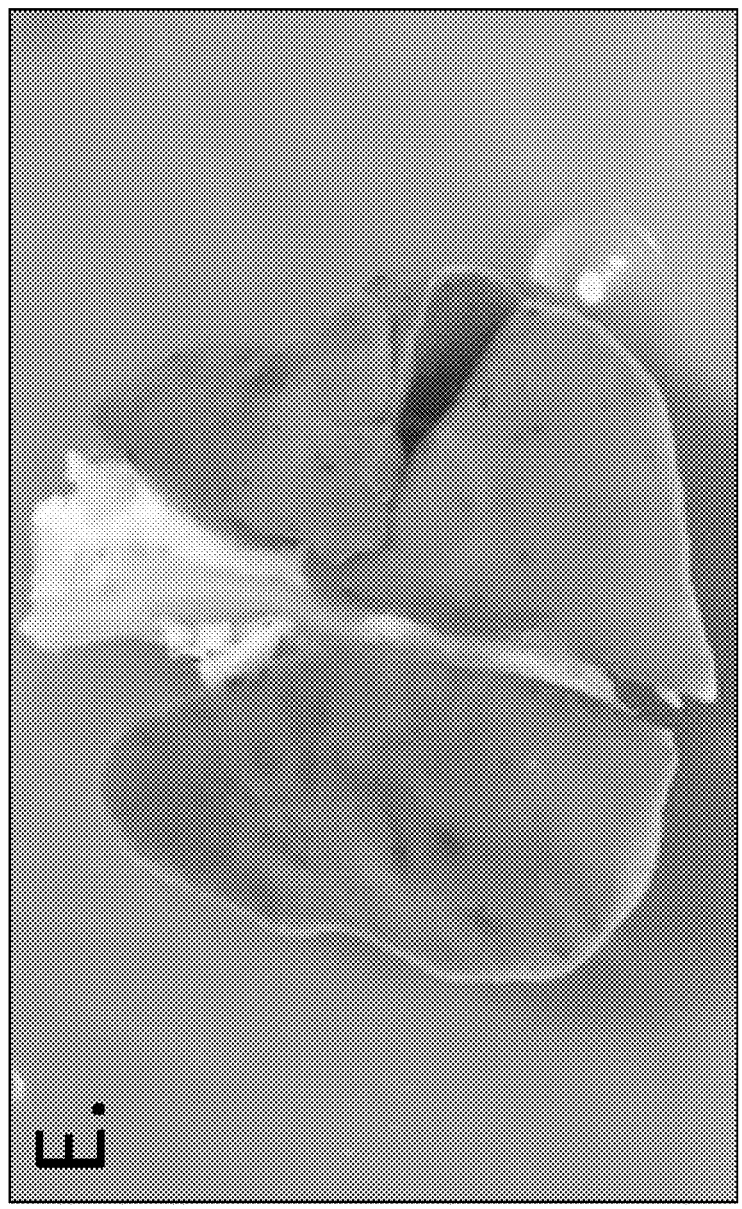
FIG. 8E depicts a control lung of a 14-week-old wild type rat, which were treated with X-gal. The control lung showed a low level of background staining for LacZ.
Figure 8F:
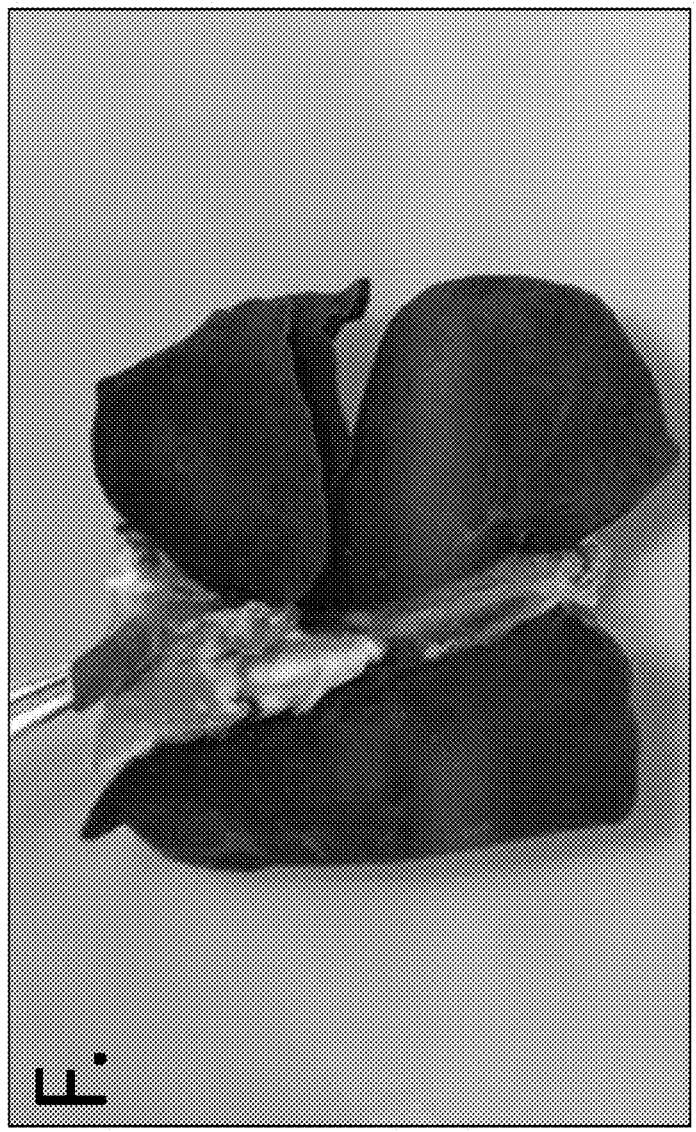
FIG. 8F depicts LacZ expression in the lung of a 14-week-old rRosa26 heterozygote rat. The lacZ reporter was expressed ubiquitously throughout the lung of the rRosa26 heterozygote.
Figure 8H:
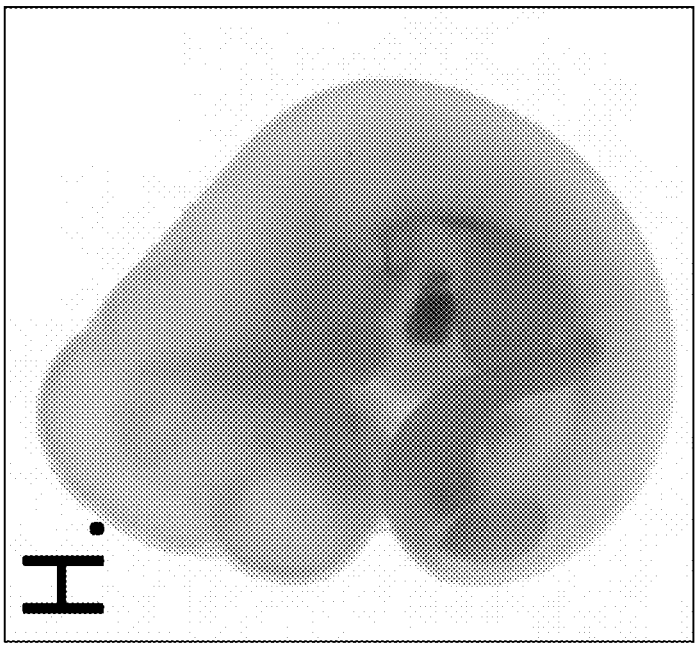
FIGS. 8G and H depict LacZ expression in e12.5 embryos. In contrast to the wild-type control embryo (FIG. 8H), which shows a low level of background LacZ staining, the rRosa26 heterozygous embryo exhibited ubiquitous expression of the LacZ reporter throughout the embryo.
FIGS. 8I and J depict LacZ expression in e14.5 embryos. In contrast to the wild-type control embryo (FIG. 8J), which shows a low level of background LacZ staining, the rRosa26 heterozygous rat embryo exhibited ubiquitous expression of the LacZ reporter throughout the embryo.
Figure 8G:
Figure 8J:
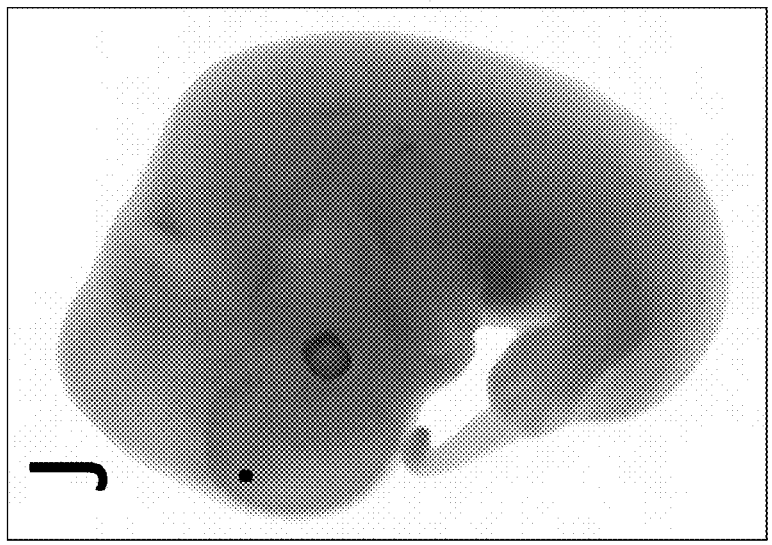
Figure 8I:
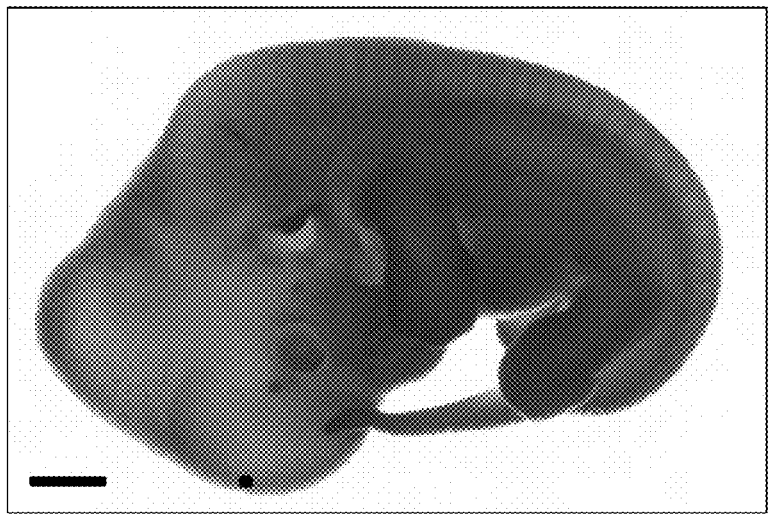

Chimeric rats were produced by blastocyst injection and transmission of the rESC genome through the germline. Chimeras produced by blastocyst microinjection using parental ACI.G1 rESC are shown in FIG. 5. F1 agouti pups with albino littermates, sired by the ACI/SD chimera labeled with an asterisk (*) in FIG. 5 are shown in FIG. 6.

Germline transmission of parental rESC. Three euploid rESC lines were evaluated for pluripotency by microinjection into albino SD blastocysts. Chimeras were identified by agouti coat color indicating rESC contribution. For each line, a majority of chimeras transmitted the rESC genome to F1 offspring (Table 4).

TABLE 4

Germline Transmission of Parental rESC

| Line | Chimeras bred | Germline transmitters | Total pups from GLT chimeras | rESC-derived pups | GLT efficiency (%) |
|---|---|---|---|---|---|
| ACI.G1 | 5 | 3 (60%) | 103 | 11 | 11 |
| DA.2B | 5 | 4 (80%) | 129 | 11 | 9 |
| DA.2C (XX) | 3 | 2 (66%) | 45 | 7 | 16 |

Example 3: rESC Targeting: The Rat Rosa 26 Locus

The rRosa26 locus lies between the Setd5 and Thumpd3 genes as in mouse, with the same spacing. The rRosa 26 locus (FIG. 7, Panel B) differs from the mRosa 26 locus (FIG. 7, Panel A). The mRosa26 transcripts consist of 2 or 3 exons. The rat locus contains a 2nd exon 1 (Ex 1b) in addition to the homologous exon to mouse exon1 (Ex1a). No 3rd exon has been identified in rat. Targeting of a rRosa26 allele is depicted in FIG. 7, Panel C, where homology arms of 5 kb each were cloned by PCR using genomic DNA from DA rESC. The targeted allele contains a SA-lacZ-hUb-neo cassette replacing a 117 bp deletion in the rRosa26 intron.

Targeting efficiency at the rRosa 26 locus was determined (Table 5). Linearized vector was electroporated into DA or ACI rESC, and transfected colonies were cultured in 2i media+G418, using standard techniques. Individual colonies were picked and screened using a Loss of Allele (LOA) assay (Valenzuela, D. et al. (2003) High-throughput engineering of the mouse genome coupled with high-resolution expression analysis, Nature Biotech. 21:652-660, incorporated herein by reference).

TABLE 5 rRosa26 Targeting Efficiency

| Cell line | Colonies picked | Reconfirmed positives | Targeting efficiency (%) |
|---|---|---|---|
| DA.2B | 192 | 4 | 2.1 |
| ACI.G1 | 96 | 4 | 4.2 |

Chimera production and germline transmission using targeted Rosa26 rESC. Reconfirmed targeted rRosa26 clones were microinjected into SD blastocysts, which were then transferred to pseudopregnant DS recipient females, using standard techniques. Chimeras were identified by coat color; male F0 chimeras were bred to SD females. Germline (agouti) F1 pups were genotyped for the presence of the targeted Rosa26 allele; nine of 22 agouti pups genotyped as heterozygous at the Rosa26 locus (Table 6).

TABLE 6

Germline Transmission Using Targeted Rosa26 rESC

| Cell line | R26 clones injected | Clones producing Chimeras | Germline Transmitting Clones | Total Pups | rESC-derived Pups | ESC-derived pups (%) |
|---|---|---|---|---|---|---|
| DA.2B | 4 | 3 | 2 | AH7: 64<br>AE3: 112 | AH7: 41<br>AE3: 6 | AH7: 63<br>AE3: 3 |
| ACI.G1 | 4 | 4 | 1 | DE9: 39 | DE9: 4 | 10 |

Example 3: Derivation of Rat Embryonic Stem Cells

Superovulation Protocol, Rats
Day 0: injected with pregnant mare serum: IP, 20 U (0.4 ml).
Day 1: no action
Day 2: (46 hr. later): injected with hCG, IP, 50 U (1 ml). set up single female matings.
Day 3: checked plugs. Females were plugged. This is day 0.5.
Day 6 (e3.5): Euthanized females and flushed embryos.
ES Cell Derivation Protocol (Superovulation)
Day 0:
1) Euthanized female rat with $CO_2$.
2) Swabbed ventral abdomen with 70% ethanol; using scissors, opened the ventral body wall to expose the viscera.
3) Dissected out the oviducts and uterine horns and placed them into a tissue culture dish containing warm N2B27 media. Washed out as much blood as possible and transferred to a new dish with N2B27.
4) Using a 1 ml syringe and a blunt 27 g needle, flushed media through the uterine horns and oviducts to eject blastocysts into the media.
5) Collected the blastocysts with a mouth pipet and transfer to embryo culture dish containing KSOM+2i (1 μMPD0325901, 3 μM CHIR99021). KSOM is a culture medium produced by Millipore. Catalog number is MR-106-D.
6) Cultured overnight at 37°; 7.5% $CO_2$.

ES Cell Derivation Protocol (Frozen Embryos)
Day 0:
1) Thawed frozen 8-cell embryos (commercially obtained) into M2 medium. Cultured 10 minutes at room temperature.
2) Transferred to KSOM+2i and culture overnight.

ES Cell Derivation Protocol (Same for Both)
Day 1:
1) Transferred cavitated embryos to 2i medium & culture overnight.
2) Continued culturing un-cavitated embryos in KSOM+2i Day 2:
1) Transferred all remaining embryos to 2i medium (whether or not they've cavitated).
2) Cultured overnight; continued culturing earlier embryos in 2i medium.

Day 3:
1) Transferred embryos for 30-60 seconds with Acid Tyrodes to remove the zona pellucida.
2) Washed embryos 3× in 2i medium to remove Acid Tyrodes.
3) Deposited each embryo into a separate well of a 96-well feeder plate (the well contains a monolayer of mitotically inactivated mouse embryonic fibroblasts (MEFs).
4) Cultured overnight in 2i medium.

Day 4-5:
1) Monitored plated embryos for the presence of an outgrowth (an amorphous undifferentiated mass of cells). Outgrowths are ready for transfer when they are approximately twice the size of the plated embryo.
2) Each day: remove spent media with a micropipet and replace with fresh 2i media.
3) Transferred outgrowths to new feeder wells:
   a. Removed spent media and gently wash well with PBS.
   b. Removed PBS and add 30 μl 0.05% trypsin; incubate for 10 minutes.
   c. Stopped trypsin reaction by adding 30 μl 2i+10% FBS.
   d. Gently dissociated the cells with a micropipettor and transferred entire contents of the well to a new well in a 24-well feeder plate. This was Passage 1 (P1).
   e. Cultured overnight in 2i medium.

Day 5-8: (timing depends on how fast each line expands)
1) Changed media each day (2i media) and monitored for the presence of colonies with an ESC morphology.
2) When colonies appear, continued culturing until colonies expand to ~50% confluency.
3) Trypsinzed and passaged colonies as before; plated on feeders, 1 well per line, in a 6-well dish. This was Passage 2 (P2).

Ongoing:
1) Continued feeding and monitoring each line until approximately 50% confluent.
2) Trypsinized cells as usual.
3) stopped trypsin with 2i+10% FBS; pelleted the cells by centrifugation (5', 1200 rpm in Beckman-Coulter tabletop centrifuge).
4) Aspirated the supernatant and gently resuspend the cells in 400 μl Freezing Medium (70% 2i, 20% FBS, 10% DMSO).
5) Distributed the cells into 2 vials and freeze at −80°. This was Passage 3 (P3).
6) For long-term storage, transferred the vials to liquid N2 storage.

The 2i media was prepared as follows in Table 7.

| Reagent | Vendor | Concentration |
| --- | --- | --- |
| DMEM/F12 basal media | Invitrogen/Life Technologies | 1x |
| Neurobasal media | Invitrogen/Life Technologies | 1x |
| Penicillin/streptomycin | Invitrogen/Life Technologies | 1% |
| L-Glutamine | Invitrogen/Life Technologies | 4 mM |
| 2-Mercaptoethanol | Invitrogen/Life Technologies | 0.1 mM |
| N2 supplement | Invitrogen/Life Technologies | 1x |
| B27 supplement | Invitrogen/Life Technologies | 1x |
| LIF | Millipore | 100 U/ml |
| PD0325901 (MEK inhibitor). | Stemgent | 1 uM |
| CHIR99021 (GSK inhibitor). | Stemgent | 3 uM |

Materials:
  Pregnant Mare's Serum Gonadotropin (PMSG)
  Human Pregnancy Urine Chorionic Gonadotropin (HCG)
  Female Rats (5-12 weeks old)
  Male rats (12 wks. to 8 mos. old), one per cage
  Syringes/needles
  Animal room with lights on 6:00-18:00
Procedure:
  Day 1: 8:00-10:00 AM
  Inject females with 20 IU PMSG (0.4 ml), IP
  Discard unused PMSG.
  Day 3: 8:00-10:00 AM (48 hours after PMSG injection)
  Inject females with 50 IU HCG (1 ml), IP
  Place one female per male in mating cage.
  Discard unused HCG.
  Day 4: 8:00-10:00 AM (24 hrs. after HCG injection)
  Check females for plugs.
Hormone Suppliers
  PMSG: Sigma #G-4877 (1000 IU). Resuspend in PBS to a final [ ] of 50 IU/ml. Store at −20° in 1 ml aliquots.

HCG: Sigma #CG-5 (5000 IU). Resuspend in PBS to a final [ ] of 50 IU/ml. Store at −20° in 1 ml aliquots.

Example 4: Karyotyping of Rat Embryonic Stem Cell Lines

The rat ES cell line generated herein were karyotyped, and the results are summarized in Tables 8-11.

TABLE 8

| ACI.G1 Karyotyping Results | Number of cells |
| --- | --- |
| Number of cells karyotyped | 7 |
| Number of cells analyzed | 20 |
| Number of 42, XY cells | 18 |
| Number of abnormal cells | 2 |

TABLE 8-continued

| ACI.G1 Karyotyping Results | Number of cells |
| --- | --- |
| 40, XY, −5, −9 | 1 |
| 41, XY, −14 | 1 |
| 42, XY | 18 |
| Other notes: | |

Figure 9A:
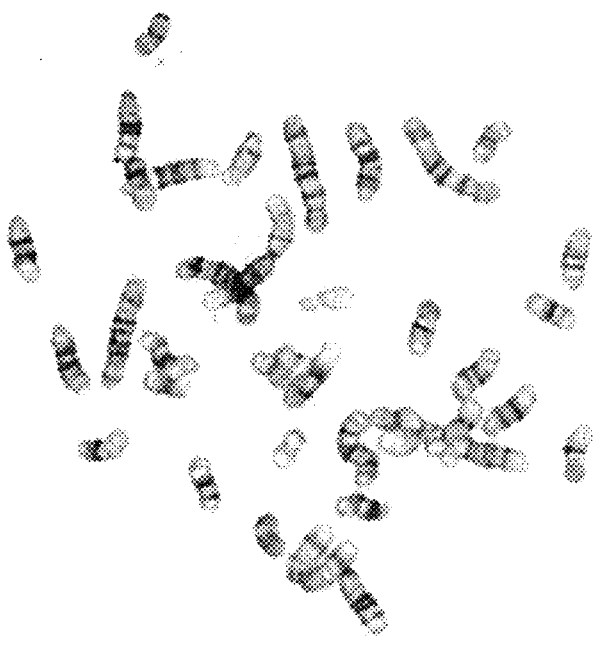
FIG. 9A-B provides a photograph showing the analysis of the chromosome number of the ACI.G1 rat ES cell line.
Figure 9B:
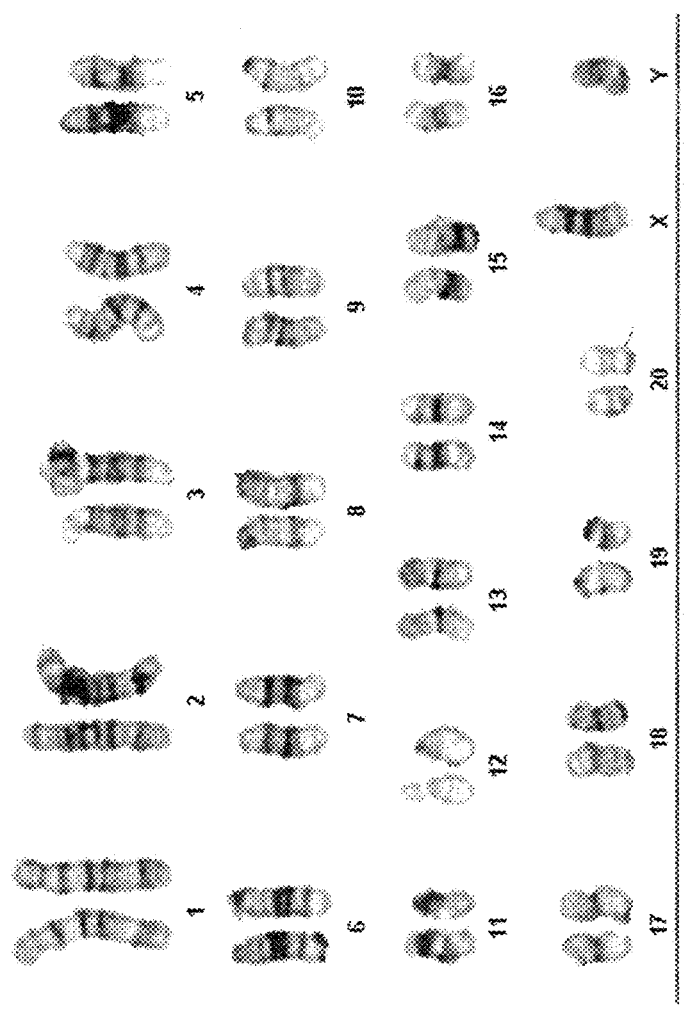

Two analyzed cells were missing different autosomes, which may be a sporadic occurrence due to technical artifact. 90% of analyzed cells had a normal male 42, XY karyotype. FIG. 9 provides a photograph showing the analysis of the chromosome number of the ACI.G1 rat ES cell line.

TABLE 9

| DA.2B Karyotyping Results | Number of cells |
| --- | --- |
| Number of cells karyotyped | 6 |
| Number of cells analyzed | 20 |
| Number of 42, XY cells | 20 |
| Number of abnormal cells | 0 |
| 42, XY | 20 |
| Other notes: | |

Figure 10A:
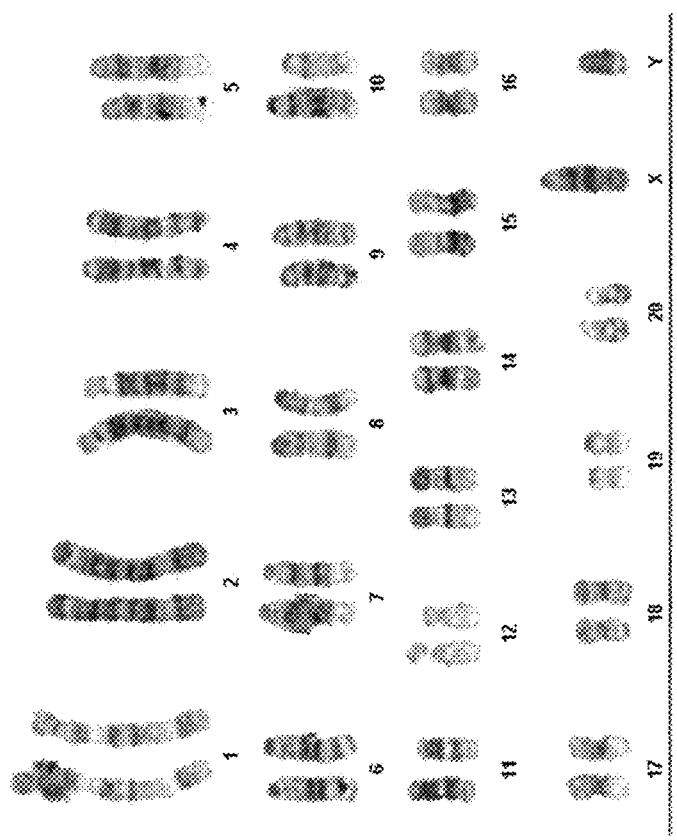
FIG. 10A-B provides a photograph showing the analysis of the chromosome number of the DA.2B rat ES cell line.
Figure 10B:

All analyzed cells had a normal diploid 42, XY karyotype. FIG. 10 provides a photograph showing the analysis of the chromosome number of the DA.2B rat ES cell line.

TABLE 10

| DA.C2 Karyotyping Results | Number of cells |
| --- | --- |
| Number of cells karyotyped | 5 |
| Number of cells analyzed | 20 |
| Number of 42, XY cells | 20 |
| Number of abnormal cells | 0 |
| 42, XX | |
| Other notes: | |

Figure 11A:
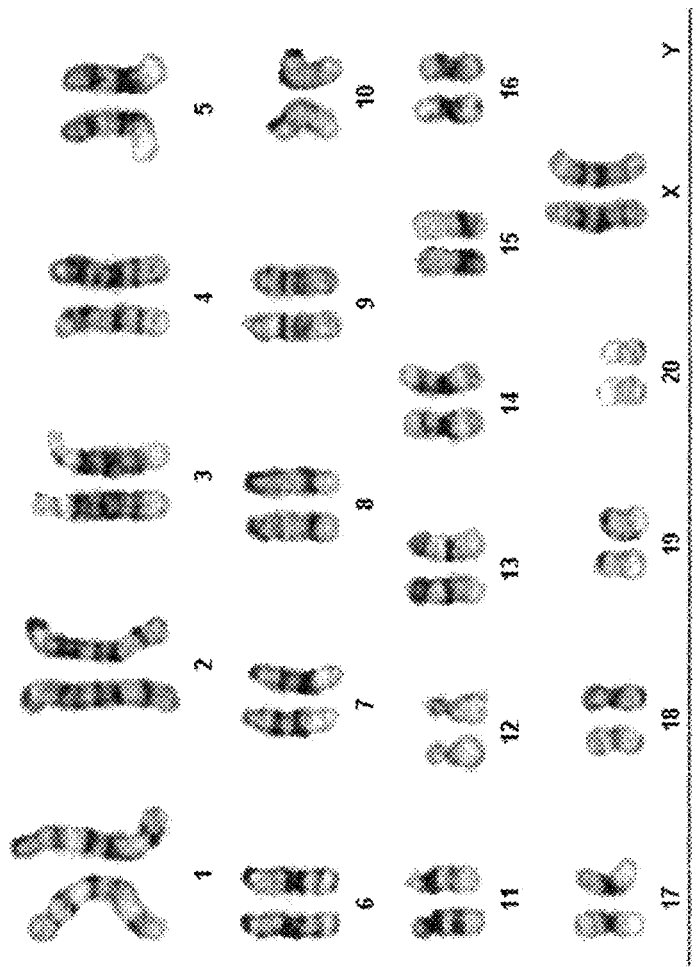
FIG. 11A-B provides a photograph showing the analysis of the chromosome number of the DA.C2 rat ES cell line.
Figure 11B:
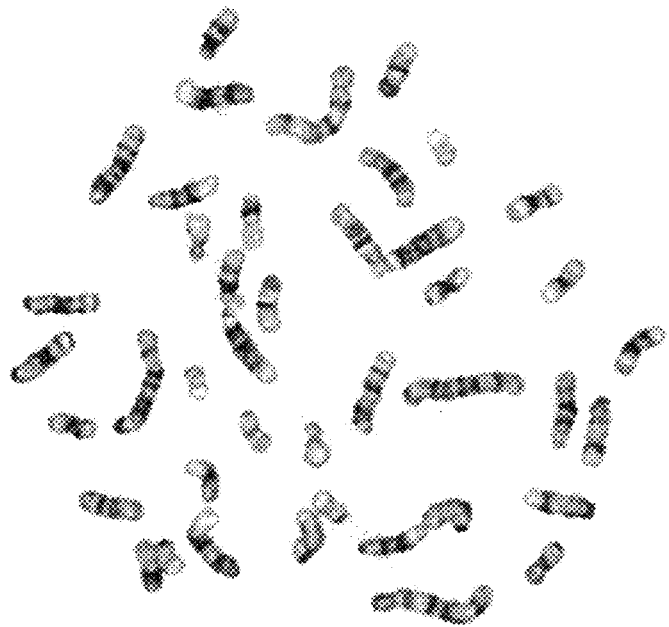

100% of analyzed cells had normal female XX rat karyotype. FIG. 11 provides a photograph showing the analysis of the chromosome number of the DA.C2 rat ES cell line.

TABLE 11

| Strain | Blastocysts plated | Lines established | Lines Karyotyped | Karyotypes |
| --- | --- | --- | --- | --- |
| BN × SD F1 | 41 | 8 (20%) | 5 | all lines were high % complex polyploid |
| ACI | 27 | 16 (60%) | 3 | G1: 90% 42 XY; others were 70-85% euploid |
| DA | 20 | 9 (45%) | 6 | 2B: 100% 42 XY; 2C: 100% 42 XX; others were 95-100% euploid |
| F344 | 4 | 1 (25%) | 0 | |
| Totals | 92 | 34 (37%) | | |

Example 5: Electroporation of Vector into Rat Embryonic Stem Cell

1. Passaged rat ES cells 24-48 hrs prior to electroporation.
2. Changed media to RVG2i+ROCKi (10 μM Y-27632) 24 hr. prior to electroporation
3. Changed media 30' prior to trypsinization.
4. Aliquoted DNA to be electroporated.
5. Allowed DNA to warm at RT for >10 min.
6. Heated DNA for 5' @ 62° C. Place DNA on ice.
7. Trypsinized cells:
  a. Collected floating colonies. Washed plate to collect as many floaters as possible.
  b. Pelleted colonies: 3' @ 750 rpm.
  c. Washed pellet 1× with 5-10 ml PBS and re-spin/pellet
  d. Aspirated supernatant; add 500λ trypsin, 0.05%+1% chicken serum.
    i. Did not pool more than 110 cm plate of colonies per tube. If there are too many colonies packed into the bottom of the tube during trypsinization they will clump and most of the cells will be lost.
  e. 4' @ 37°. Pipeted colonies several times to minimize clumping.
  f. Repeated steps 1-2×: 4' @ 37°.
  g. Stopped trypsin with 500λ RVG2i+10% FBS.
8. Pelleted cells: 5' @ 1200 rpm.
9. Resuspend cells in 10 ml PBS. Count two 20λ aliquots to determine total cell number.
10. Pelleted cells (5'/1200 rpm); calculate total cell number and total resuspension volume to achieve correct cell concentration (target #/75 μl EP buffer).
11. Resuspend in a minimal volume of EP buffer; measure total volume and adjust to target volume with EP buffer. Electroporation buffer is sold by Millipore. The catalog # is ES-003-D. See, Valenzuela et al. (2003) *Nature Biotechnology* 21:652-659, which is herein incorporated by reference.

12. Add 75λ cells to 50×DNA; transfer the 125λ cells/ DNA solution to one well of a BTX 48-well cuvette.
   a. Filled the empty wells in the same column with 125λ EP buffer.
13. Pulsed the cuvette once in the BTX electroporator:
   a. Settings: 400V; Ω; 100 μf (settings may vary)
14. Placed cuvette on ice for 15' to recover.
15. Removed cells into 5 ml RVG2i+10 μM ROCKi.
16. Added to 15 cm plate with 20 ml RVG2i+10 μM ROCKi. Plate has 2× neoR MEFs (or other MEFs depending on project). The neoR selectable marker is the neomycin phosphotransferase (neo) gene of Beck et al. (1982) Gene, 19:327-36 or in U.S. Pat. No. 7,205,148 or 6,596,541, each of which are herein incorporated by reference.
17. Incubated @ 37°. Begin selection 48 hrs later. ROCK inhibitor used was Y-27632.

Example 6: Selecting Targeted Genetic Modification in a Rat Embryonic Stem Cell

1. Passaged cells for 24-48 hrs prior to electroporation.
2. Changed media to RVG2i+ROCKi (10 μM Y-27632) 24 hr. prior to electroporation
3. Changed media 30' prior to trypsinization.
4. Aliquoted DNA to be electroporated.
5. Allowed DNA warm at RT for >10 min.
6. Heated DNA for 5' @ 62° C. Place DNA on ice.
7. Trypsinized cells:
   h. Collected floating colonies. Washed plate to collect as many floaters as possible.
   i. Pelleted colonies: 3' @ 750 rpm.
   j. Washed pellet 1× with 5-10 ml PBS and re-spin/pellet
   k. Aspirated supernatant; add 500λ trypsin, 0.05%+1% chicken serum.
      i. Did not pool more than 110 cm plate of colonies per tube. If there are too many colonies packed into the bottom of the tube during trypsinization they will clump and most of the cells will be lost.
   l. 4' @ 37°. Pipeted colonies several times to minimize clumping
   m. Repeated 1-2×: 4' @ 37°.
   n. Stopped trypsin with 500λ RVG2i+10% FBS.
8. Pelleted cells: 5' @ 1200 rpm.
9. Resuspended cells in 10 ml PBS. Count two 20λ aliquots to determine total cell number.
10. Pelleted cells (5'/1200 rpm); calculate total cell number and total resuspension volume to achieve correct cell concentration (target #175 μl EP buffer).
11. Resuspend in a minimal volume of EP buffer; measured total volume and adjusted to target volume with EP buffer.
12. Added 75λ cells to 50×DNA; transfer the 125λ cells/DNA solution to one well of a BTX 48-well cuvette.
   a. Filled the empty wells in the same column with 125λ EP buffer.
13. Pulsed the cuvette once in the BTX electroporator:
   a. Settings: 400V; 400V; Ω; 100 μF (settings may vary)
14. Placed cuvette on ice for 15' to recover.
15. Removed cells into 5 ml RVG2i+10 μM ROCKi.
16. Added to 15 cm plate with 20 ml RVG2i+10 μM ROCKi. Plate had 2× neoR MEFs (or other MEFs depending on project).
17. Incubated @ 37°. Began selection 48 hrs later.
18. G418 selection protocol was as follows:
   a. Day 2 ($2^{nd}$ day after EP): incubated cells in 2i media+G418, 75 μg/ml.
   b. Day 3: incubated cells in 2i media without G418
   c. Day 4: incubated cells in 2i media+G418, 75 μg/ml.
   d. Day 5: incubated cells in 2i media without G418
   e. Day 6: incubated cells in 2i media+G418, 75 μg/ml.
   f. Day 7: incubated cells in 2i media without G418
   g. Day 8: incubated cells in 2i media+G418, 75 μg/ml.
   h. Day 9: incubated cells in 2i media without G418
   i. Day 10: incubated cells in 2i media+G418, 75 μg/ml.
   j. Day 11: incubated cells in 2i media without G418
   k. Day 12: picked colonies to expand for screening. Each colony was dissociated in 0.05% trypsin+1% chicken serum for 10 minutes and then plated into 1 well of a 96-well feeder plate.
19. Expanded colonies for 3 days in 2i media.
20. Passaged clones 1:1 to new 96-well feeder plates.
21. Expanded clones for 3 days in 2i media.
22. For each clone, dissociated colonies in trypsin. Froze ⅔ of each clone and store at −80'; plated the remaining ⅓ onto laminin plates (96-well plates coated with 10 μg/ml laminin).
23. When the laminin plates were confluent, passed off to the screening lab for genotyping of the clones.

Example 7: Molecular Signature of the Rat Embryonic Stem Cells

The genes listed in Table 13 were expressed at levels 20-fold higher in rat ES cells than the corresponding genes in mouse ES cells. The genes listed in Table 12 were expressed at 20-fold lower in rat ES cells than the corresponding genes in mouse ES cells.

The microarray data in Tables 12 and 13 was generated as follows. Rat ES cells (ACI.G2 and DA.2B) and mouse ES cells (F1H4) were cultured in 2i media for 3 passages until confluent. F1H4 cells were cultured on gelatin-coated plates in the absence of feeders. F1H4 mouse ES cells were derived from 129S6/SvEvTac and C57BL/6NTac heterozygous embryos (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007), incorporated by reference herein in its entirety).

The following protocol was used for sample prep:
Materials included TRIzol Reagentp; RNA Lysis Buffer (Zymo Kit); and 1.5 mL Eppendorf tubes.

The 1.5 mL Eppendorf tubes were labeled with the Sample ID. Cells grown on a plate were rinsed in 37 C PBS. PBS was removed and 300 ul of Trizol was added. A scraper was used to break the cells in Trizol. The lysed cells were collected in Trizol in a 1.5 mL Eppendorf tube. For cells grown on suspension, the cells were rinsed in 37 C PBS. The cells were collected in a 1.5 mL tube, the cells were spun down, PBS was removed and 300 ul of Trizol was added. The cells were pipeted up and down to break the cells. Samples were sorted for FACS with $10^1$ to $10^5$ cells, the volume was concentrated to less than 100 uL. 4 volumes of RNA Lysis buffer was added and mix by pipetting. For sample, 320 uL RNA Lysis buffer was added to 80 uL sample. Samples were stored at −20° C.

RNA-Seq was used to measure the expression level of mouse and rat genes. Sequencing reads were mapped to mouse and rat reference genome by Tophat, and RPKM (fragments per kilobase of exon per million fragments mapped) were calculated for mouse and rat genes. Homology genes based on gene symbol were selected, and then used t-test to compare gene's expression level between mouse and rat.

miR-632 is in the top 10 highest expressed in rat ESCs but they were not expressed in mouse ES cells. There is therefore no comparative data for these genes. Based on the levels of expression compared to other genes and their known function in the embryonic development, the expression of miR-632 were used as a marker for rat ES cells.

TABLE 12

| The genes listed were expressed at levels 20-fold lower in rat ES cells than the corresponding genes in mouse ES cells. | | | | | |
|---|---|---|---|---|---|
| ID | Notes | Symbol | Entrez Gene Name | Location | Type(s) | Drug(s) |
| Abcb1b | | Abcb1b | ATP-binding cassette, sub-family B (MDR/TAP), member 1B | Plasma Membrane | transporter | |
| Acta2 | | ACTA2 | actin, alpha 2, smooth muscle, aorta | Cytoplasm | other | |
| Actg2 | | ACTG2 | actin, gamma 2, smooth muscle, enteric | Cytoplasm | other | |
| Aebp1 | | AEBP1 | AE binding protein 1 | Nucleus | peptidase | |
| Angptl2 | | ANGPTL2 | angiopoietin-like 2 | Extracellular Space | other | |
| Ankrd1 | | ANKRD1 | ankyrin repeat domain 1 (cardiac muscle) | Cytoplasm | transcription regulator | |
| Anxa1 | | ANXA1 | annexin A1 | Plasma Membrane | other | hydrocortisone |
| Anxa6 | | ANXA6 | annexin A6 | Plasma Membrane | other | |
| Anxa8 | | ANXA8L2 (includes others) | annexin A8-like 2 | Plasma Membrane | other | |
| Arhgef25 | | ARHGEF25 | Rho guanine nucleotide exchange factor (GEF) 25 | Cytoplasm | other | |
| Axl | | AXL | AXL receptor tyrosine kinase | Plasma Membrane | kinase | cabozantinib |
| Basp1 | | BASP1 | brain abundant, membrane attached signal protein 1 | Nucleus | transcription regulator | |
| Bgn | | BGN | biglycan | Extracellular Space | other | |
| Bst2 | | BST2 | bone marrow stromal cell antigen 2 | Plasma Membrane | other | |
| Btf3 | | BTF3 | basic transcription factor 3 | Nucleus | transcription regulator | |
| Btg2 | | BTG2 | BTG family, member 2 | Nucleus | transcription regulator | |
| Capsl | | CAPSL | calcyphosine-like | Other | other | |
| Cav1 | | CAV1 | caveolin 1, caveolae protein, 22 kDa | Plasma Membrane | transmembrane receptor | |
| Ccdc80 | | CCDC80 | coiled-coil domain containing 80 | Nucleus | other | |
| Ccnd2 | | CCND2 | cyclin D2 | Nucleus | other | |
| Cd248 | | CD248 | CD248 molecule, endosialin | Plasma Membrane | other | |
| Cd44 | | CD44 | CD44 molecule (Indian blood group) | Plasma Membrane | enzyme | |
| Cd97 | | CD97 | CD97 molecule | Plasma Membrane | G-protein coupled receptor | |
| Cdc42ep5 | | CDC42EP5 | CDC42 effector protein (Rho GTPase binding) 5 | Cytoplasm | other | |
| Cdh11 | | CDH11 | cadherin 11, type 2, OB-cadherin (osteoblast) | Plasma Membrane | other | |
| Cdkn2a | | CDKN2A | cyclin-dependent kinase inhibitor 2A | Nucleus | transcription regulator | |

TABLE 12-continued

The genes listed were expressed at levels 20-fold lower in rat
ES cells than the corresponding genes in mouse ES cells.

| ID | Notes | Symbol | Entrez Gene Name | Location | Type(s) | Drug(s) |
|---|---|---|---|---|---|---|
| Cdo1 | | CDO1 | cysteine dioxygenase type 1 | Cytoplasm | enzyme | |
| Clip3 | | CLIP3 | CAP-GLY domain containing linker protein 3 | Cytoplasm | other | |
| Cln5 | | CLN5 | ceroid-lipofuscinosis, neuronal 5 | Cytoplasm | other | |
| Cnn1 | | CNN1 | calponin 1, basic, smooth muscle | Cytoplasm | other | |
| Col1a1 | | COL1A1 | collagen, type I, alpha 1 | Extracellular Space | other | collagenase *clostridium histolyticum* |
| Col1a2 | | COL1A2 | collagen, type I, alpha 2 | Extracellular Space | other | collagenase *clostridium histolyticum* |
| Col3a1 | | COL3A1 | collagen, type III, alpha 1 | Extracellular Space | other | collagenase *clostridium histolyticum* |
| Col5a2 | | COL5A2 | collagen, type V, alpha 2 | Extracellular Space | other | collagenase *clostridium histolyticum* |
| Col6a2 | | COL6A2 | collagen, type VI, alpha 2 | Extracellular Space | other | collagenase *clostridium histolyticum* |
| Cryab | | CRYAB | crystallin, alpha B | Nucleus | other | |
| Csf1 | | CSF1 | colony stimulating factor 1 (macrophage) | Extracellular Space | cytokine | |
| Cth | | CTH | cystathionase (cystathionine gamma-lyase) | Cytoplasm | enzyme | |
| Cthrc1 | | CTHRC1 | collagen triple helix repeat containing 1 | Extracellular Space | other | |
| Ctsc | | CTSC | cathepsin C | Cytoplasm | peptidase | |
| Cyr61 | | CYR61 | cysteine-rich, angiogenic inducer, 61 | Extracellular Space | other | |
| Ddx58 | | DDX58 | DEAD (Asp-Glu-Ala-Asp) box polypeptide 58 | Cytoplasm | enzyme | |
| Dkk3 | | DKK3 | dickkopf WNT signaling pathway inhibitor 3 | Extracellular Space | cytokine | |
| Dmc1 | | DMC1 | DNA meiotic recombinase 1 | Nucleus | enzyme | |
| Dpysl3 | | DPYSL3 | dihydropyrimidinase-like 3 | Cytoplasm | enzyme | |
| Dse | | DSE | dermatan sulfate epimerase | Cytoplasm | enzyme | |
| Dusp1 | | DUSP1 | dual specificity phosphatase 1 | Nucleus | phosphatase | |
| Dusp27 | | DUSP27 | dual specificity phosphatase 27 (putative) | Other | phosphatase | |
| Dusp9 | | DUSP9 | dual specificity phosphatase 9 | Nucleus | phosphatase | |
| Ece2 | | ECE2 | endothelin converting enzyme 2 | Plasma Membrane | peptidase | |
| Ecm1 | | ECM1 | extracellular matrix protein 1 | Extracellular Space | transporter | |
| Egr1 | | EGR1 | early growth response 1 | Nucleus | transcription regulator | |
| Emp1 | | EMP1 | epithelial membrane protein 1 | Plasma Membrane | other | |
| Emp3 | | EMP3 | epithelial membrane protein 3 | Plasma Membrane | other | |
| Ephx2 | | EPHX2 | epoxide hydrolase 2, cytoplasmic | Cytoplasm | enzyme | |

TABLE 12-continued

The genes listed were expressed at levels 20-fold lower in rat
ES cells than the corresponding genes in mouse ES cells.

| ID | Notes | Symbol | Entrez Gene Name | Location | Type(s) | Drug(s) |
|---|---|---|---|---|---|---|
| F3 | | F3 | coagulation factor III (thromboplastin, tissue factor) | Plasma Membrane | transmembrane receptor | activated recombinant human factor VII |
| Fau | | FAU | Finkel-Biskis-Reilly murine sarcoma virus (FBR-MuSV) ubiquitously expressed | Cytoplasm | other | |
| Fbn1 | | FBN1 | fibrillin 1 | Extracellular Space | other | |
| Fbxo15 | | FBXO15 | F-box protein 15 | Other | transcription regulator | |
| Fhl2 | | FHL2 | four and a half LIM domains 2 | Nucleus | transcription regulator | |
| Flnc | | FLNC | filamin C, gamma | Cytoplasm | other | |
| Fos | | FOS | FBJ murine osteosarcoma viral oncogene homolog | Nucleus | transcription regulator | |
| Fundc2 | | FUNDC2 | FUN14 domain containing 2 | Cytoplasm | other | |
| Gjb3 | | GJB3 | gap junction protein, beta 3, 31 kDa | Plasma Membrane | transporter | |
| Gpa33 | | GPA33 | glycoprotein A33 (transmembrane) | Plasma Membrane | other | |
| Gpbp1l1 | | GPBP1L1 | GC-rich promoter binding protein 1-like 1 | Other | other | |
| Gpc3 | | GPC3 | glypican 3 | Plasma Membrane | other | |
| Grb10 | | GRB10 | growth factor receptor-bound protein 10 | Cytoplasm | other | |
| Gstm1 | | GSTM5 | glutathione S-transferase mu 5 | Cytoplasm | enzyme | |
| Hap1 | | HAP1 | huntingtin-associated protein 1 | Cytoplasm | other | |
| Hist1h2bc | | HIST2H2BE (includes others) | histone cluster 2, H2be | Nucleus | other | |
| Hmga2 | | HMGA2 | high mobility group AT-hook 2 | Nucleus | enzyme | |
| Hmgn3 | | Hmgn3 | high mobility group nucleosomal binding domain 3 | Nucleus | other | |
| Hormad1 | | HORMAD1 | HORMA domain containing 1 | Nucleus | other | |
| Hsd17b14 | | HSD17B14 | hydroxysteroid (17-beta) dehydrogenase 14 | Cytoplasm | enzyme | |
| Hspb1 | | HSPB1 | heat shock 27 kDa protein 1 | Cytoplasm | other | |
| Hspb8 | | HSPB8 | heat shock 22 kDa protein 8 | Cytoplasm | kinase | |
| Htra1 | | HTRA1 | HtrA serine peptidase 1 | Extracellular Space | peptidase | |
| Ifi204 | | Ifi204 (includes others) | interferon activated gene 204 | Nucleus | transcription regulator | |
| Ifi44 | | IFI44 | interferon-induced protein 44 | Cytoplasm | other | |
| Ifit1 | | IFIT1B | interferon-induced protein with tetratricopeptide repeats 1B | Cytoplasm | other | |
| Ifitm3 | | IFITM2 | interferon induced transmembrane protein 2 | Cytoplasm | other | |
| Igf2 | | IGF2 | insulin-like growth factor 2 (somatomedin A) | Extracellular Space | growth factor | |

TABLE 12-continued

The genes listed were expressed at levels 20-fold lower in rat
ES cells than the corresponding genes in mouse ES cells.

| ID | Notes | Symbol | Entrez Gene Name | Location | Type(s) | Drug(s) |
|---|---|---|---|---|---|---|
| Igfbp7 | | IGFBP7 | insulin-like growth factor binding protein 7 | Extracellular Space | transporter | |
| Il1rl1 | | IL1RL1 | interleukin 1 receptor-like 1 | Plasma Membrane | transmembrane receptor | |
| Inhba | | INHBA | inhibin, beta A | Extracellular Space | growth factor | |
| Inhbb | | INHBB | inhibin, beta B | Extracellular Space | growth factor | |
| Irf7 | | IRF7 | interferon regulatory factor 7 | Nucleus | transcription regulator | |
| Isg15 | | ISG15 | ISG15 ubiquitin-like modifier | Extracellular Space | other | |
| Itga5 | | ITGA5 | integrin, alpha 5 (fibronectin receptor, alpha polypeptide) | Plasma Membrane | transmembrane receptor | |
| Jun | | JUN | jun proto-oncogene | Nucleus | transcription regulator | |
| Junb | | JUNB | jun B proto-oncogene | Nucleus | transcription regulator | |
| Lgals3bp | | LGALS3BP | lectin, galactoside-binding, soluble, 3 binding protein | Plasma Membrane | transmembrane receptor | |
| Lgals9 | | LGALS9 | lectin, galactoside-binding, soluble, 9 | Extracellular Space | other | |
| Lmna | | LMNA | lamin A/C | Nucleus | other | |
| Lox | | LOX | lysyl oxidase | Extracellular Space | enzyme | |
| Loxl2 | | LOXL2 | lysyl oxidase-like 2 | Extracellular Space | enzyme | |
| Loxl3 | | LOXL3 | lysyl oxidase-like 3 | Extracellular Space | enzyme | |
| Lrp1 | | LRP1 | low density lipoprotein receptor-related protein 1 | Plasma Membrane | transmembrane receptor | |
| Mageb16 | | MAGEB16 | melanoma antigen family B, 16 | Other | other | |
| Mcam | | MCAM | melanoma cell adhesion molecule | Plasma Membrane | other | |
| Mgp | | MGP | matrix Gla protein | Extracellular Space | other | |
| Mmp2 | | MMP2 | matrix metallopeptidase 2 (gelatinase A, 72 kDa gelatinase, 72 kDa type IV collagenase) | Extracellular Space | peptidase | marimastat |
| Mxra8 | | MXRA8 | matrix-remodelling associated 8 | Other | other | |
| Myl9 | | MYL9 | myosin, light chain 9, regulatory | Cytoplasm | other | |
| Mylpf | | MYLPF | myosin light chain, phosphorylatable, fast skeletal muscle | Cytoplasm | other | |
| Nab2 | | NAB2 | NGFI-A binding protein 2 (EGR1 binding protein 2) | Nucleus | transcription regulator | |
| Ndufb4 | | NDUFB4 | NADH dehydrogenase (ubiquinone) 1 beta subcomplex, 4, 15 kDa | Cytoplasm | transporter | |
| Npm1 | | NPM1 | nucleophosmin (nucleolar phosphoprotein B23, numatrin) | Nucleus | transcription regulator | |
| Nr0b1 | | NR0B1 | nuclear receptor subfamily 0, group B, member 1 | Nucleus | ligand-dependent nuclear receptor | |

TABLE 12-continued

The genes listed were expressed at levels 20-fold lower in rat
ES cells than the corresponding genes in mouse ES cells.

| ID | Notes | Symbol | Entrez Gene Name | Location | Type(s) | Drug(s) |
|---|---|---|---|---|---|---|
| Nr4a1 | | NR4A1 | nuclear receptor subfamily 4, group A, member 1 | Nucleus | ligand-dependent nuclear receptor | |
| Nrp2 | | NRP2 | neuropilin 2 | Plasma Membrane | kinase | |
| Oas1a | | OAS1 | 2'-5'-oligoadenylate synthetase 1, 40/46 kDa | Cytoplasm | enzyme | |
| Oasl2 | | Oasl2 | 2'-5' oligoadenylate synthetase-like 2 | Other | enzyme | |
| P4ha2 | | P4HA2 | prolyl 4-hydroxylase, alpha polypeptide II | Cytoplasm | enzyme | |
| Parp3 | | PARP3 | poly (ADP-ribose) polymerase family, member 3 | Nucleus | enzyme | |
| Pcolce | | PCOLCE | procollagen C-endopeptidase enhancer | Extracellular Space | other | |
| Pcyt1b | | PCYT1B | phosphate cytidylyltransferase 1, choline, beta | Cytoplasm | enzyme | |
| Pdgfc | | PDGFC | platelet derived growth factor C | Extracellular Space | growth factor | |
| Phlda1 | | PHLDA1 | pleckstrin homology-like domain, family A, member 1 | Cytoplasm | other | |
| Phlda2 | | PHLDA2 | pleckstrin homology-like domain, family A, member 2 | Cytoplasm | other | |
| Pla2g1b | | PLA2G1B | phospholipase A2, group IB (pancreas) | Extracellular Space | enzyme | niflumic acid |
| Pla2g4a | | PLA2G4A | phospholipase A2, group IVA (cytosolic, calcium-dependent) | Cytoplasm | enzyme | quinacrine |
| Porcn | | PORCN | porcupine homolog (*Drosophila*) | Cytoplasm | other | |
| Postn | | POSTN | periostin, osteoblast specific factor | Extracellular Space | other | |
| Prrx1 | | PRRX1 | paired related homeobox 1 | Nucleus | transcription regulator | |
| Prss23 | | PRSS23 | protease, serine, 23 | Extracellular Space | peptidase | |
| Psmb8 | | PSMB8 | proteasome (prosome, macropain) subunit, beta type, 8 | Cytoplasm | peptidase | |
| Ptgs2 | | PTGS2 | prostaglandin-endoperoxide synthase 2 (prostaglandin G/H synthase and cyclooxygenase) | Cytoplasm | enzyme | acetaminophen/pentazocine, acetaminophen/clemastine/pseudoephedrine, aspirin/butalbital/caffeine, acetaminophen/caffeine/dihydrocodeine, aspirin/hydrocodone, aspirin/oxycodone, acetaminophen/aspirin/caffeine, aspirin/pravastatin, acetaminophen/dexbrompheniramine/pseudoephedrine, |

TABLE 12-continued

The genes listed were expressed at levels 20-fold lower in rat ES cells than the corresponding genes in mouse ES cells.

| ID | Notes | Symbol | Entrez Gene Name | Location | Type(s) | Drug(s) |
|---|---|---|---|---|---|---|
| | | | | | | aspirin/meprobamate, aspirin/caffeine/ propoxyphene, aspirin/butalbital/ caffeine/codeine, aspirin/caffeine/ dihydrocodeine, chlorpheniramine/ ibuprofen/ pseudoephedrine, licofelone, menatetrenone, icosapent, suprofen, lornoxicam, tiaprofenic acid, lumiracoxib, tenoxicam, naproxen/ sumatriptan, ibuprofen/ phenylephrine, acetaminophen/ aspirin/codeine, naproxen/ esomeprazole, famotidine/ ibuprofen, ibuprofen/ phenylephrine/ chlorpheniramine, diclofenac/ misoprostol, acetaminophen/ butalbital/caffeine, hydrocodone/ ibuprofen, acetaminophen/ hydrocodone, acetaminophen/ tramadol, acetaminophen/ codeine, acetaminophen/ oxycodone, acetaminophen/ propoxyphene, niflumic acid, nitroaspirin, ketoprofen, diclofenac, etoricoxib, naproxen, meclofenamic acid, pomalidomide, meloxicam, celecoxib, dipyrone, nimesulide, acetaminophen, mefenamic acid, diflunisal, ibuprofen, GW406381X, phenylbutazone, indomethacin, sulfasalazine, piroxicam, valdecoxib, aspirin, carprofen, zomepirac, rofecoxib, aspirin/ methocarbamol, |

TABLE 12-continued

The genes listed were expressed at levels 20-fold lower in rat ES cells than the corresponding genes in mouse ES cells.

| ID | Notes | Symbol | Entrez Gene Name | Location | Type(s) | Drug(s) |
|---|---|---|---|---|---|---|
| | | | | | | aspirin/caffeine/ orphenadrine, aspirin/ carisoprodol, aspirin/ carisoprodol/ codeine, acetaminophen/ butalbital, balsalazide, aspirin/ dipyridamole, acetaminophen/ butalbital/caffeine/ codeine, racemic flurbiprofen, phenacetin, sulindac, nabumetone, etodolac, tolmetin, ketorolac, oxaprozin, mesalamine, salsalate, fenoprofen, salicylic acid, acetaminophen/ chlorpheniramine/ hydrocodone/ phenylephrine/ caffeine, bromfenac |
| Ptn | | PTN | pleiotrophin | Extracellular Space | growth factor | |
| Ptrf | | PTRF | polymerase I and transcript release factor | Nucleus | transcription regulator | |
| Rarg | | RARG | retinoic acid receptor, gamma | Nucleus | ligand-dependent nuclear receptor | etretinate, adapalene, isotretinoin, tazarotene, acitretin, tretinoin, alitretinoin, fenretinide |
| Rgs16 | | RGS16 | regulator of G-protein signaling 16 | Cytoplasm | other | |
| Rn45s | | Rn45s | 45S pre-ribosomal RNA | Other | other | |
| Rpl10a | | RPL10A | ribosomal protein L10a | Other | other | |
| Rpl31 | | RPL31 | ribosomal protein L31 | Other | other | |
| Rpl37a | | RPL37A | ribosomal protein L37a | Cytoplasm | other | |
| Rps10 | | RPS10-NUDT3 | RPS10-NUDT3 readthrough | Cytoplasm | other | |
| Rps14 | | RPS14 | ribosomal protein S14 | Cytoplasm | translation regulator | |
| Rps20 | | Rps20 | ribosomal protein S20 | Cytoplasm | other | |
| Rps26 | | RPS26 | ribosomal protein S26 | Cytoplasm | other | |
| Rps9 | | RPS9 | ribosomal protein S9 | Cytoplasm | translation regulator | |
| S100a4 | | S100A4 | S100 calcium binding protein A4 | Cytoplasm | other | |
| S100a6 | | S100A6 | S100 calcium binding protein A6 | Cytoplasm | transporter | |
| Schip1 | | SCHIP1 | schwannomin interacting protein 1 | Cytoplasm | other | |
| Sdc2 | | SDC2 | syndecan 2 | Plasma Membrane | other | |

TABLE 12-continued

The genes listed were expressed at levels 20-fold lower in rat
ES cells than the corresponding genes in mouse ES cells.

| ID | Notes | Symbol | Entrez Gene Name | Location | Type(s) | Drug(s) |
|---|---|---|---|---|---|---|
| Serpine1 | | SERPINE1 | serpin peptidase inhibitor, clade E (nexin, plasminogen activator inhibitor type 1), member 1 | Extracellular Space | other | drotrecogin alfa |
| Serpine2 | | SERPINE2 | serpin peptidase inhibitor, clade E (nexin, plasminogen activator inhibitor type 1), member 2 | Extracellular Space | other | |
| Serpinf1 | | SERPINF1 | serpin peptidase inhibitor, clade F (alpha-2 antiplasmin, pigment epithelium derived factor), member 1 | Extracellular Space | other | |
| Sh3gl2 | | SH3GL2 | SH3-domain GRB2-like 2 | Plasma Membrane | enzyme | |
| Slc19a2 | | SLC19A2 | solute carrier family 19 (thiamine transporter), member 2 | Plasma Membrane | transporter | |
| Slc25a5 | | SLC25A5 | solute carrier family 25 (mitochondrial carrier; adenine nucleotide translocator), member 5 | Cytoplasm | transporter | clodronic acid |
| Slc29a1 | | SLC29A1 | solute carrier family 29 (equilibrative nucleoside transporter), member 1 | Plasma Membrane | transporter | |
| Slc35f2 | | SLC35F2 | solute carrier family 35, member F2 | Other | other | |
| Snrpn | | SNRPN | small nuclear ribonucleoprotein polypeptide N | Nucleus | other | |
| Snx22 | | SNX22 | sorting nexin 22 | Other | transporter | |
| Sparc | | SPARC | secreted protein, acidic, cysteine-rich (osteonectin) | Extracellular Space | other | |
| Spp1 | | SPP1 | secreted phosphoprotein 1 | Extracellular Space | cytokine | |
| Sult4a1 | | SULT4A1 | sulfotransferase family 4A, member 1 | Cytoplasm | enzyme | |
| Tagln | | TAGLN | transgelin | Cytoplasm | other | |
| Tcea3 | | TCEA3 | transcription elongation factor A (SII), 3 | Nucleus | transcription regulator | |
| Tgfb3 | | TGFB3 | transforming growth factor, beta 3 | Extracellular Space | growth factor | |
| Thbs1 | | THBS1 | thrombospondin 1 | Extracellular Space | other | |
| Thbs2 | | THBS2 | thrombospondin 2 | Extracellular Space | other | |
| Tm4sf1 | | TM4SF1 | transmembrane 4 L six family member 1 | Plasma Membrane | other | |
| Tmbim1 | | TMBIM1 | transmembrane BAX inhibitor motif containing 1 | Cytoplasm | other | |
| Tmem176b | | TMEM176B | transmembrane protein 176B | Other | other | |
| Tnc | | TNC | tenascin C | Extracellular Space | other | |

TABLE 12-continued

The genes listed were expressed at levels 20-fold lower in rat ES cells than the corresponding genes in mouse ES cells.

| ID | Notes | Symbol | Entrez Gene Name | Location | Type(s) | Drug(s) |
|---|---|---|---|---|---|---|
| Tpd52l1 | | TPD52L1 | tumor protein D52-like 1 | Cytoplasm | other | |
| Tpm2 | | TPM2 | tropomyosin 2 (beta) | Cytoplasm | other | |
| Usp18 | | USP18 | ubiquitin specific peptidase 18 | Cytoplasm | peptidase | |
| Vim | | VIM | vimentin | Cytoplasm | other | |
| Wfdc2 | | WFDC2 | WAP four-disulfide core domain 2 | Extracellular Space | other | |
| Wisp2 | | WISP2 | WNT1 inducible signaling pathway protein 2 | Extracellular Space | growth factor | |
| Ybx1 | | YBX1 | Y box binding protein 1 | Nucleus | transcription regulator | |

TABLE 13

The genes listed were expressed at levels 20-fold higher in rat ES cells than the corresponding genes in mouse ES cells.

| ID | Notes | Symbol | Entrez Gene Name | Location | Type(s) | Drug(s) |
|---|---|---|---|---|---|---|
| Ajap1 | | Ajap1 | adherens junction associated protein 1 | Other | other | |
| Amd1 | | AMD1 | adenosylmethionine decarboxylase 1 | Cytoplasm | enzyme | |
| Ankrd2 | | ANKRD2 | ankyrin repeat domain 2 (stretch responsive muscle) | Nucleus | transcription regulator | |
| Arhgef9 | | ARHGEF9 | Cdc42 guanine nucleotide exchange factor (GEF) 9 | Cytoplasm | other | |
| Atp5h | | Atp5h | ATP synthase, H+ transporting, mitochondrial F0 complex, subunit d | Cytoplasm | enzyme | |
| Btg3 | | BTG3 | BTG family, member 3 | Nucleus | other | |
| Car6 | | CA6 | carbonic anhydrase VI | Extracellular Space | enzyme | methazolamide, hydrochlorothiazide, acetazolamide, trichloromethiazide, chlorothiazide, chlorthalidone, benzthiazide, sulfacetamide, topiramate |
| Camk4 | | CAMK4 | calcium/calmodulin-dependent protein kinase IV | Nucleus | kinase | |
| Capn12 | | CAPN12 | calpain 12 | Other | peptidase | |
| Cct6b | | CCT6B | chaperonin containing TCP1, subunit 6B (zeta 2) | Cytoplasm | transporter | |
| Cdx2 | | CDX2 | caudal type homeobox 2 | Nucleus | transcription regulator | |
| Cldn5 | | CLDN5 | claudin 5 | Plasma Membrane | other | |
| Clec3a | | CLEC3A | C-type lectin domain family 3, member A | Other | other | |
| Clic6 | | CLIC6 | chloride intracellular channel 6 | Plasma Membrane | ion channel | |
| Dhrsx | | DHRSX | dehydrogenase/reductase (SDR family) X-linked | Other | enzyme | |
| Dpysl2 | | DPYSL2 | dihydropyrimidinase-like 2 | Cytoplasm | enzyme | |
| Dusp26 | | DUSP26 | dual specificity phosphatase 26 (putative) | Cytoplasm | enzyme | |

TABLE 13-continued

The genes listed were expressed at levels 20-fold higher in rat ES cells than the corresponding genes in mouse ES cells.

| ID | Notes | Symbol | Entrez Gene Name | Location | Type(s) | Drug(s) |
|---|---|---|---|---|---|---|
| Eci3 | | Eci3 | enoyl-Coenzyme A delta isomerase 3 | Other | enzyme | |
| Eef2k | | EEF2K | eukaryotic elongation factor-2 kinase | Cytoplasm | kinase | |
| Efna1 | | EFNA1 | ephrin-A1 | Plasma Membrane | other | |
| Epha4 | | EPHA4 | EPH receptor A4 | Plasma Membrane | kinase | |
| Fank1 | | FANK1 | fibronectin type III and ankyrin repeat domains 1 | Nucleus | transcription regulator | |
| Fhit | | FHIT | fragile histidine triad | Cytoplasm | enzyme | |
| Filip1 | | FILIP1 | filamin A interacting protein 1 | Cytoplasm | other | |
| Fmod | | FMOD | fibromodulin | Extracellular Space | other | |
| Foxe1 | | FOXE1 | forkhead box E1 (thyroid transcription factor 2) | Nucleus | transcription regulator | |
| Fry | | FRY | furry homolog (*Drosophila*) | Extracellular Space | other | |
| Gjb5 | | GJB5 | gap junction protein, beta 5, 31.1 kDa | Plasma Membrane | transporter | |
| Gpx2 | | GPX2 | glutathione peroxidase 2 (gastrointestinal) | Cytoplasm | enzyme | |
| Grxcr2 | | GRXCR2 | glutaredoxin, cysteine rich 2 | Other | other | |
| Hecw2 | | HECW2 | HECT, C2 and WW domain containing E3 ubiquitin protein ligase 2 | Extracellular Space | enzyme | |
| Hey2 | | HEY2 | hairy/enhancer-of-split related with YRPW motif 2 | Nucleus | transcription regulator | |
| Icos | | Icos | inducible T-cell co-stimulator | Plasma Membrane | other | |
| Ifitm1 | | IFITM1 | interferon induced transmembrane protein 1 | Plasma Membrane | transmembrane receptor | |
| Il1f8 | | Interleukin 36 beta | | | | |
| Il28ra | | Interleukin 28 receptor, alpha | | | | |
| Igfbpl1 | | IGFBPL1 | insulin-like growth factor binding protein-like 1 | Other | other | |
| Ipcef1 | | IPCEF1 | interaction protein for cytohesin exchange factors 1 | Cytoplasm | enzyme | |
| Lctl | | Lctl | lactase-like | Cytoplasm | other | |
| Ldhd | | LDHD | lactate dehydrogenase D | Cytoplasm | enzyme | |
| Lef1 | | LEF1 | lymphoid enhancer-binding factor 1 | Nucleus | transcription regulator | |
| Lefty1 | | LEFTY1 | left-right determination factor 1 | Extracellular Space | growth factor | |
| Lifr | | LIFR | leukemia inhibitory factor receptor alpha | Plasma Membrane | transmembrane receptor | |
| Lpar2 | | LPAR2 | lysophosphatidic acid receptor 2 | Plasma Membrane | G-protein coupled receptor | |
| Mog | | MOG | myelin oligodendrocyte glycoprotein | Extracellular Space | other | |
| Morn5 | | MORN5 | MORN repeat containing 5 | Other | other | |
| Pigz | | NCBP2 | nuclear cap binding protein subunit 2, 20 kDa | Nucleus | other | |

TABLE 13-continued

The genes listed were expressed at levels 20-fold higher in rat ES cells than the corresponding genes in mouse ES cells.

| ID | Notes | Symbol | Entrez Gene Name | Location | Type(s) | Drug(s) |
|---|---|---|---|---|---|---|
| Nptxr | | NPTXR | neuronal pentraxin receptor | Plasma Membrane | transmembrane receptor | |
| Ntm | | NTM | neurotrimin | Plasma Membrane | other | |
| Nutf2 | | NUTF2 | nuclear transport factor 2 | Nucleus | transporter | |
| Ocln | | OCLN | occludin | Plasma Membrane | enzyme | |
| Olr1 | | OLR1 | oxidized low density lipoprotein (lectin-like) receptor 1 | Plasma Membrane | transmembrane receptor | |
| Pabpc4 | | PABPC4 | poly(A) binding protein, cytoplasmic 4 (inducible form) | Cytoplasm | translation regulator | |
| Pde11a | | PDE11A | phosphodiesterase 11A | Cytoplasm | enzyme | dyphylline, nitroglycerin, aminophylline, dipyridamole, tolbutamide, tadalafil, theophylline, pentoxifylline |
| Pdyn | | PDYN | prodynorphin | Extracellular Space | transporter | |
| Per3 | | PER3 | period circadian clock 3 | Nucleus | other | |
| Pllp | | PLLP | plasmolipin | Plasma Membrane | transporter | |
| Ppp1r14c | | PPP1R14C | protein phosphatase 1, regulatory (inhibitor) subunit 14C | Cytoplasm | other | |
| Pramel6 | | Pramel6 | preferentially expressed antigen in melanoma like 6 | Other | other | |
| Ptpn18 | | PTPN18 | protein tyrosine phosphatase, non-receptor type 18 (brain-derived) | Nucleus | phosphatase | |
| Pycr1 | | PYCR1 | pyrroline-5-carboxylate reductase 1 | Cytoplasm | enzyme | |
| Rab26 | | RAB26 | RAB26, member RAS oncogene family | Plasma Membrane | enzyme | |
| Ramp2 | | RAMP2 | receptor (G protein-coupled) activity modifying protein 2 | Plasma Membrane | transporter | pramlintide |
| Rbm24 | | RBM24 | RNA binding motif protein 24 | Other | other | |
| Rhag | | RHAG | Rh-associated glycoprotein | Plasma Membrane | peptidase | |
| Rpl3 | | RPL3 | ribosomal protein L3 | Cytoplasm | other | homoharringtonine |
| Sall3 | | SALL3 | sal-like 3 (*Drosophila*) | Nucleus | other | |
| Satb1 | | SATB1 | SATB homeobox 1 | Nucleus | transcription regulator | |
| Scg2 | | SCG2 | secretogranin II | Extracellular Space | cytokine | |
| Slc15a1 | | SLC15A1 | solute carrier family 15 (oligopeptide transporter), member 1 | Plasma Membrane | transporter | |
| Slc1a1 | | SLC1A1 | solute carrier family 1 (neuronal/epithelial high affinity glutamate transporter, system Xag), member 1 | Plasma Membrane | transporter | riluzole |

TABLE 13-continued

The genes listed were expressed at levels 20-fold higher in rat ES cells than the corresponding genes in mouse ES cells.

| ID | Notes | Symbol | Entrez Gene Name | Location | Type(s) | Drug(s) |
|---|---|---|---|---|---|---|
| Slc24a5 | | Slc24a5 | solute carrier family 24 (sodium/potassium/calcium exchanger), member 5 | Other | other | |
| Slc37a2 | | SLC37A2 | solute carrier family 37 (glucose-6-phosphate transporter), member 2 | Other | transporter | |
| 40424 | | SNTB1 | syntrophin, beta 1 (dystrophin-associated protein A1, 59 kDa, basic component 1) | Plasma Membrane | other | |
| St6galnac3 | | ST6GALNAC3 | ST6 (alpha-N-acetyl-neuraminyl-2,3-beta-galactosyl-1,3)-N-acetylgalactosaminide alpha-2,6-sialyltransferase 3 | Cytoplasm | enzyme | |
| Tex12 | | TEX12 | testis expressed 12 | Nucleus | other | |
| Tex15 | | TEX15 | testis expressed 15 | Extracellular Space | other | |
| Tfap2a | | TFAP2A | transcription factor AP-2 alpha (activating enhancer binding protein 2 alpha) | Nucleus | transcription regulator | |
| Tmc1 | | TMC1 | transmembrane channel-like 1 | Plasma Membrane | other | |
| Tmem130 | | TMEM130 | transmembrane protein 130 | Other | other | |
| Tmem30b | | TMEM30B | transmembrane protein 30B | Other | other | |
| Tomm20 | | TOMM20 | translocase of outer mitochondrial membrane 20 homolog (yeast) | Cytoplasm | transporter | |
| Tox3 | | TOX3 | TOX high mobility group box family member 3 | Other | other | |
| Ttc25 | | TTC25 | tetratricopeptide repeat domain 25 | Cytoplasm | other | |
| Tymp | | TYMP | thymidine phosphorylase | Extracellular Space | growth factor | |
| Ubb | | Ubb | ubiquitin B | Cytoplasm | other | |
| Vamp7 | | VAMP7 | vesicle-associated membrane protein 7 | Cytoplasm | transporter | |
| Wfdc12 | | Wfdc12 | WAP four-disulfide core domain 12 | Extracellular Space | other | |
| Wfdc15a | | Wfdc15a | WAP four-disulfide core domain 15A | Other | other | |
| Wfdc6a | | Wfdc6a | WAP four-disulfide core domain 6A | Other | other | |

TABLE 14

A subset of genes from Table 13 which are expressed at levels 20-fold higher in rat ES cells than the corresponding genes in mouse ES cells.

| ID | Entrez Gene Name |
|---|---|
| Ajap1 | Adherens Junctions Associate Protein 1 |
| Cldn5 | Claudin 5 |
| Arhgef9 | Cdc42 guanine nucleotide exchange facter 9 |
| Camk4 | Calcium/calmodulin-dependent protein kinase IV |
| Efna1 | ephrin-A1 |
| Epha4 | EPH receptor A4 |
| Gjb5 | gap junction protein beta 5 |
| Igfbpl1 | Insulin-like growth factor binding protein-like 1 |
| Il1f8 | Interleukin 36 beta |
| Il28ra | Interleukin 28 receptor, alpha |
| Lefty1 | left-right determination factor 1 |
| Lifr | Leukemia inhibitory factor receptor alpha |
| Lpar2 | Lysophosphatidic acid receptor 2 |
| Ntm | Neuronal pentraxin receptor |
| Ptpn18 | Protein tyrosine phosphatase non-receptor type 18 |
| Cdx2 | Caudal type homeobox 2 |
| Fank1 | Fibronectin type III and ankyrin repeat domains 1 |
| Foxe1 | Forkhead box E1 (thyroid transcription factor 2) |
| Hey2 | Hairy/enhancer-of-split related with YRPW motif 2 |
| Lef1 | Lymphoid enhancer-binding factor 1 |
| Sall3 | Sal-like 3 (Drosophila) |
| Satb1 | SATB homeobox 1 |

An additional molecular signature employing the pluripotency markers/genes for the rat ES cells has also been developed. Table 15 provides a gene list and their expression ranks from the RNA profiling data. mRNA was isolated from rat ES cells and the expression level of various pluripotency markers were compared relative to each other. The "pluripotency genes" which are listed are genes that other groups have used (mostly in mouse, but also in rat) as markers of ES cells. Mesoderm endoderm and neural are similarly defined. By "rank" is refers to the expression in our experiment: the higher the rank (1 is highest) the higher the expression. For example, Oct4's rank of 13 means that, of all the genes assayed, it was expressed higher than all but 12 genes. Background in this experiment was any expression value below 30; 6107 genes had expression values of 30 or higher.

TABLE 15

Rat ES cell molecular signature employing the pluripotency, mesodermal, endodermal, neural and trophectoderm markers/genes.

| Pluripotency | Pluripotency Rank | Mesodermal | Mesodermal Rank | Endodermal | Endodermal Rank | Neural | Neural Rank | Trophectoderm | Trophectoderm Rank |
|---|---|---|---|---|---|---|---|---|---|
| c-Myc | 8248 | Brachyury | 7542 | Gata6 | 11195 | Nestin | 7761 | Cdx2 | 739 |
| Dnmt3L | 127 | Flk1 | Not tested | Sox17 | 11418 | Pax6 | 13570 | | |
| Dppa2 | Not tested | Nodal | 3050 | Hhex1 | 4571 | Sox2 | 681 | | |
| Dppa5 | Not tested | Bmp4 | 3072 | Nodal | 3050 | | | | |
| Ecat1 | 9714 | Bmpr2 | 6382 | Ext1 | 6091 | | | | |
| Eras | 2541 | | | Sox7 | 10284 | | | | |
| Err-beta | 1368 | | | | | | | | |
| Fbxo15 | 1369 | | | | | | | | |
| Fgf4 | 3440 | | | | | | | | |
| Fthl17 | Not tested | | | | | | | | |
| Gdf3 | 2771 | | | Rank > 6107 = bkg expression | | | | | |
| Klf4 | 836 | | | | | | | | |
| Lef1 | 1313 | | | | | | | | |
| LIF receptor | 724 | | | | | | | | |
| Lin28 | 828 | | | | | | | | |
| Nanog | 774 | | | | | | | | |
| Oct4 | 13 | | | | | | | | |
| Rexo1 | 6119 | | | | | | | | |
| Sox15 | 4524 | | | | | | | | |
| Sox2 | 681 | | | | | | | | |
| SSEA1 | Not tested | | | | | | | | |
| SSEA4 | Not tested | | | | | | | | |
| Stella | Not tested | | | | | | | | |
| Tcl1 | Not tested | | | | | | | | |
| Utf1 | 1501 | | | | | | | | |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Unless otherwise apparent from the context of any embodiment, aspect, step or feature of the invention can be used in combination with any other. Reference to a range includes any integers within the range, any subrange within the range. Reference to multiple ranges includes composites of such ranges.

That which is claimed:

1. A method of making a genetically modified rat whose genome comprises a targeted genetic modification that is transmitted through the germline, comprising:
(a) providing a rat ES cell line comprising a population of rat ES cells obtained by culturing isolated rat ES cells on a feeder cell layer that is not modified to express leukemia inhibitory factor (LIF) with a medium comprising N2 supplement, B27 supplement, about 50 U/mL to about 150 U/mL LIF, and a combination of inhibitors consisting of MEK inhibitor PD0325901 and GSK3 inhibitor CHIR99021, wherein the population of rat ES cells:
lacks expression of c-Myc;
forms spherical, free-floating colonies in culture;
is diploid; and
is germline competent;
(b) obtaining a rat ES cell clone comprising the targeted genetic modification, wherein the obtaining consists of:
(i) modifying the population of rat ES cells to comprise the targeted genetic modification; and
(ii) culturing the rat ES cells from step (b)(i) under the conditions set forth in step (a) and identifying in a single cloning step a rat ES cell clone comprising the targeted genetic modification and capable of transmitting the targeted genetic modification through the germline;
(c) introducing the rat ES cell clone into a rat host embryo, wherein the rat ES cell clone is from a different rat strain than the rat host embryo;
(d) gestating the rat host embryo comprising the rat ES cell clone in a surrogate mother, wherein the surrogate mother produces an F0 progeny genetically modified rat comprising the targeted genetic modification; and (e) breeding the F0 progeny genetically modified rat with another rat to produce an F1 progeny genetically modified rat comprising the targeted genetic modification, wherein the targeted genetic modification is transmitted through the germline.

2. The method of claim 1, wherein the providing step (a) comprises:
(i) culturing in vitro a first feeder cell layer that is not modified to express leukemia inhibitory factor (LIF) and a morula or a blastocyst stage rat embryo,
wherein the zona pellucida of the morula or blastocyst-stage rat embryo has been removed, and
wherein the culture conditions maintain pluripotency of a rat ES cell and comprise a medium comprising N2 supplement, B27 supplement, about 50 U/mL to about 150 U/mL LIF, and a combination of inhibitors consisting of MEK inhibitor PD0325901 and GSK3 inhibitor CHIR99021, wherein said culturing produces an outgrowth of undifferentiated rat ES cells; and
(ii) transferring the outgrowth from (i) to an in vitro culture well comprising a second feeder cell layer that is not modified to express LIF; and
(iii) culturing the outgrowth from (ii) under conditions comprising the medium comprising N2 supplement, B27 supplement, about 50 U/mL to about 150 U/mL LIF, and a combination of inhibitors consisting of MEK inhibitor PD0325901 and GSK3 inhibitor CHIR99021, thereby establishing a pluripotent rat ES cell line.

3. The method of claim 2, wherein the morula or blastocyst stage rat embryo is from a superovulated rat.

4. The method of claim 1, wherein the rat ES cell line is derived from an ACI rat or a Dark Agouti (DA) rat.

5. The method of claim 1, wherein the rat ES cell line is a male (XY) rat ES cell line.

6. The method of claim 1, wherein the rat ES cell line is a female (XX) rat ES cell line.

7. The method of claim 1, wherein the modifying step (b)(i) comprises one or more rounds of electroporation.

8. The method of claim 1, wherein the targeted genetic modification comprises an insertion, a deletion, a knockout, a knockin, a point mutation, or a combination thereof.

9. The method of claim 8, wherein the targeted genetic modification comprises an insertion of a heterologous polynucleotide into the genome of the rat ES cells.

10. The method of claim 1, wherein the modifying step (b)(i) comprises modifying the population of rat ES cells to comprise two or more targeted modifications, wherein the modified rat ES cells can transmit the two or more targeted genetic modifications through the germline.

11. The method of claim 1, wherein the targeted genetic modification is generated via a homologous recombination event.

12. The method of claim 11, wherein the targeted genetic modification is generated by employing a targeting vector comprising upstream and downstream homology arms flanking an insert polynucleotide, wherein the homology arms correspond to genomic regions within a targeted genomic locus.

13. The method of claim 12, wherein the modifying step (b)(i) comprises:
(i) introducing into the population of rat ES cells a heterologous polynucleotide comprising a selection marker, wherein the selection marker is operably linked to a promoter active in the rat ES cells, and wherein the selection marker is present in the targeting vector; and
(ii) culturing in vitro the rat ES cells produced by step (a) in alternating first and second culture media, wherein the first culture medium comprises an effective amount of a selection agent for a first time period and the second culture medium does not comprise the selection agent, wherein the in vitro culture conditions are sufficient to maintain pluripotency, thereby selecting modified rat ES cells having the heterologous polynucleotide stably integrated into the genome.

14. The method of claim 13, wherein the first and second culture media are alternated every 24 hours.

15. The method of claim 13, wherein the selection marker imparts resistance to an antibiotic.

16. The method of claim 13, wherein the selection marker comprises one or more of neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-tk).

17. The method of claim 13, wherein the selection marker has one or more of the following characteristics:
(a) the selection marker comprises a non-attenuated selection marker gene; and
(b) the selection marker has an increased activity compared to a wild type selection marker.

18. The method of claim 13, wherein the modified rat ES cells comprise multiple copies of the selection marker stably incorporated into the genome.

19. The method of claim 1, wherein the targeted genetic modification is generated using a nuclease agent that generates a single or double strand break at a targeted genomic locus.

20. The method of claim 19, wherein the nuclease agent is a transcription activator-like effector nuclease (TALEN), a zinc-finger nuclease (ZFN), a meganuclease, or a CRISPR/Cas system.

21. The method of claim 1, wherein the LIF is a mouse LIF or has at least 91% sequence identity to SEQ ID NO: 1.

22. The method of claim 1, wherein the concentration of LIF in the medium is between about 75 U/mL to about 125 U/mL.

23. The method of claim 22, wherein the concentration of LIF in the medium is between about 90 U/mL to about 110 U/mL.

24. The method of claim 23, wherein the concentration of LIF in the medium is about 100 U/mL.

25. The method of claim 24, wherein the concentration of the MEK inhibitor is about 1 µM, and the concentration of the GSK3 inhibitor is about 3 µM.

26. The method of claim 1, wherein the concentration of the MEK inhibitor is 0.8 µM to about 1.2 µM, and the concentration of the GSK3 inhibitor is about 2.5 µM to about 3 µM or 3 µM to about 3.5 µM.

27. The method of claim 26, wherein the concentration of the MEK inhibitor is about 1 µM, and the concentration of the GSK3 inhibitor is about 3 µM.

28. The method of claim 1, wherein the feeder cell layer comprises a monolayer of mitotically inactivated mouse embryonic fibroblasts (MEFs).

29. The method of claim 1, wherein the feeder cell layer comprises mitotically inactivated mouse embryonic fibroblasts, and the medium is a 2i medium comprising DMEM/F12 basal medium, Neurobasal medium, N2 supplement, B27 supplement, LIF, and a combination of inhibitors consisting of MEK inhibitor PD0325901 and GSK3 inhibitor CHIR99021.

30. The method of claim 29, wherein the concentration of the LIF is 100 U/mL, the concentration of the MEK inhibitor is about 1 μM, and the concentration of the GSK3 inhibitor is about 3 μM.

31. The method of claim 1, wherein step (e) comprises breeding a male F0 rat identified in step (d) with a wild type female rat to produce an F1 progeny that is heterozygous for the targeted genetic modification.

32. The method of claim 31, further comprising:
(f) breeding a male rat of the F1 progeny with a female rat of the F1 progeny to obtain an F2 progeny that is homozygous for the targeted genetic modification.

33. The method of claim 31, wherein at least 3% of the F1 progeny are derived from the rat ES cell clone identified in step (b)(ii).

34. The method of claim 33, wherein at least 10% of the F1 progeny are derived from the rat ES cell clone identified in step (b)(ii).

35. The method of claim 34, wherein at least 60% of the F1 progeny are derived from the rat ES cell clone identified in step (b)(ii).

36. The method of claim 1, wherein the medium further comprises DMEM/F12 basal medium and Neurobasal medium.

37. The method of claim 1, wherein the rat ES cells have one or more of the following characteristics:
(a) the rat ES cells express at least one pluripotency marker selected from Dnmt3L, Eras, Err-beta, Fbxo15, Fgf4, Gdf3, Klf4, Lef1, LIF receptor, Lin28, Nanog, Oct4, Sox15, Sox2, and Utf1;
(b) the rat ES cells do not express one or more pluripotency markers selected from Ecat1 and Rexo1;
(c) the rat ES cells do not express one or more mesodermal markers selected from Brachyury and Bmpr2;
(d) the rat ES cells do not express one or more endodermal markers selected from Gata6, Sox17, and Sox7;
(e) the rat ES cells do not express one or more neural markers selected from Nestin and Pax6;
(f) the rat ES cells expresses one or more pluripotency markers selected from Oct-4, Sox2, and alkaline phosphatase; and
(g) the rat ES cells express of one or more rat ESC-specific genes selected from Adherens Junctions Associated Protein 1 (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbp11), Interleukin 36 beta (Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), and miR-632.

\* \* \* \* \*

UNITED STATES PATENT AND TRADEMARK OFFICE
CERTIFICATE OF CORRECTION

PATENT NO. : 10,329,582 B2
APPLICATION NO. : 15/242025
DATED : June 25, 2019
INVENTOR(S) : Jeffrey D. Lee et al.

Page 1 of 1

It is certified that error appears in the above-identified patent and that said Letters Patent is hereby corrected as shown below:

In the Claims

In Claim 1, Column 84, Lines 1-12, should be moved to after the SEQUENCE LISTING and before Column 84, Line 57

Signed and Sealed this
Twenty-ninth Day of September, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 203
<212> TYPE: PRT
<213> ORGANISM: Mus musculus

<400> SEQUENCE: 1

Met Lys Val Leu Ala Ala Gly Ile Val Pro Leu Leu Leu Leu Val Leu
1               5                   10                  15

His Trp Lys His Gly Ala Gly Ser Pro Leu Pro Ile Thr Pro Val Asn
            20                  25                  30

Ala Thr Cys Ala Ile Arg His Pro Cys His Gly Asn Leu Met Asn Gln
        35                  40                  45

Ile Lys Asn Gln Leu Ala Gln Leu Asn Gly Ser Ala Asn Ala Leu Phe
    50                  55                  60

Ile Ser Tyr Tyr Thr Ala Gln Gly Glu Pro Phe Pro Asn Asn Val Glu
65                  70                  75                  80

Lys Leu Cys Ala Pro Asn Met Thr Asp Phe Pro Ser Phe His Gly Asn
                85                  90                  95

Gly Thr Glu Lys Thr Lys Leu Val Glu Leu Tyr Arg Met Val Ala Tyr
            100                 105                 110

Leu Ser Ala Ser Leu Thr Asn Ile Thr Arg Asp Gln Lys Val Leu Asn
        115                 120                 125

Pro Thr Ala Val Ser Leu Gln Val Lys Leu Asn Ala Thr Ile Asp Val
    130                 135                 140

Met Arg Gly Leu Leu Ser Asn Val Leu Cys Arg Leu Cys Asn Lys Tyr
145                 150                 155                 160

Arg Val Gly His Val Asp Val Pro Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
        195                 200
```